(12) United States Patent
Guler et al.

(10) Patent No.: US 10,849,974 B2
(45) Date of Patent: Dec. 1, 2020

(54) COMPOSITIONS AND THEIR USE FOR CONTROLLING THE NERVOUS SYSTEM IN VIVO

(71) Applicant: University of Virginia Patent Foundation, Charlottesville, VA (US)

(72) Inventors: Ali Deniz Guler, Charlottesville, VA (US); Michael Alex Wheeler, Cape May Court House, NJ (US)

(73) Assignee: University of Virginia Patent Foundation, Charlottesville, VA (US)

(*) Notice: Subject to any disclaimer, the term of this patent is extended or adjusted under 35 U.S.C. 154(b) by 213 days.

(21) Appl. No.: 15/770,141

(22) PCT Filed: Oct. 21, 2016

(86) PCT No.: PCT/US2016/058267
§ 371 (c)(1),
(2) Date: Apr. 20, 2018

(87) PCT Pub. No.: WO2017/070573
PCT Pub. Date: Apr. 27, 2017

(65) Prior Publication Data
US 2019/0111135 A1 Apr. 18, 2019

Related U.S. Application Data

(60) Provisional application No. 62/244,264, filed on Oct. 21, 2015.

(51) Int. Cl.
*A61K 41/00* (2020.01)
*C07K 14/705* (2006.01)
(Continued)

(52) U.S. Cl.
CPC ........ *A61K 41/0052* (2013.01); *A61K 9/0009* (2013.01); *A61K 9/5068* (2013.01);
(Continued)

(58) Field of Classification Search
CPC ........ A61P 25/08; A61P 25/00; A61K 9/5068; A61K 38/1709; A61K 38/1767;
(Continued)

(56) References Cited

U.S. PATENT DOCUMENTS

2004/0115132 A1* 6/2004 Young .................... A61K 31/70
424/9.34

FOREIGN PATENT DOCUMENTS

WO  WO-2017070573 A1  4/2017

OTHER PUBLICATIONS

Tosha et al. Ferritin Protein Nanocage Ion Channels: Gating by N-Terminal Extensions. Apr. 13, 2012. Jour of Biol Chem. vol. 287, No. 16, pp. 13016-13025. (Year: 2012).*

(Continued)

*Primary Examiner* — Christine H Matthews
*Assistant Examiner* — Joshua Daryl D Lannu
(74) *Attorney, Agent, or Firm* — Schwegman Lundberg & Woessner, P.A.

(57) ABSTRACT

Optogenetic and chemogenetic actuators are critical for deconstructing the neural correlates of behavior. However, these tools have several drawbacks, including invasive modes of stimulation or slow on/off kinetics. These disadvantages have been overcome by synthesizing a magnetically sensitive actuator, Magneto, comprised of the cation channel, TRPV4, fused to the paramagnetic protein, ferritin. Magneto permits non-invasive magnetic control over neuronal activity by showing remote stimulation of cells using in vitro calcium imaging assays, electrophysiological recordings in brain slices, in vivo electrophysiological recordings in freely moving mice, and behavioral outputs in zebrafish and mice. As proof of concept, the first magnetogenetic control of the nervous system was demonstrated by using Magneto to delineate a causal role of striatal dopamine (Continued)

receptor 1 neurons in mediating reward behavior in mice. Together, our results present Magneto as a novel actuator capable of remotely controlling circuits associated with complex animal behaviors.

19 Claims, 30 Drawing Sheets

(51) Int. Cl.
      *C07K 14/47*      (2006.01)
      *A61P 25/08*     (2006.01)
      *A61P 25/00*     (2006.01)
      *A61N 2/00*      (2006.01)
      *A61K 9/00*      (2006.01)
      *A61K 38/17*     (2006.01)
      *A61K 9/50*      (2006.01)
      *C07K 14/72*     (2006.01)
      *B82Y 5/00*      (2011.01)

(52) U.S. Cl.
CPC ...... *A61K 38/1709* (2013.01); *A61K 38/1767* (2013.01); *A61K 41/0028* (2013.01); *A61N 2/006* (2013.01); *A61P 25/00* (2018.01); *A61P 25/08* (2018.01); *C07K 14/47* (2013.01); *C07K 14/705* (2013.01); *C07K 14/723* (2013.01); *B82Y 5/00* (2013.01); *C07K 2319/00* (2013.01); *C07K 2319/01* (2013.01)

(58) Field of Classification Search
CPC .............. A61K 9/0009; A61K 41/0028; A61K 41/0052; A61N 2/006; C07K 14/723; C07K 14/705; C07K 14/47; C07K 2319/00; C07K 2319/01; B82Y 5/00
See application file for complete search history.

(56) References Cited

OTHER PUBLICATIONS

"International Application Serial No. PCT/US2016/058267, International Search Report dated Feb. 15, 2017", 5 pgs.

"International Application Serial No. PCT/US2016/058267, Written Opinion dated Feb. 15, 2017", 7 pgs.

Ali D, Guler, et al., "Transient activation of specific neurons in mice by selective expression of the capsaicin receptor", Nature Communications,. XP055338208, United Kingdom ISSN: 2041-1723, D0I: 10.1038/ncomnsI749, (Mar. 20, 2012).

Raag D, Airan, et al., "Temporally precise in vivo control of intracellular signalling", Nature, Nature Publishing Group, United Kingdom, XP002631861, ISSN: 0028-0836, DOI: 10.1038/NATURE07926, (Apr. 23, 2009), 1025-1029.

Stanley, S A, et al., "Remote regulation of glucose homeostasis in mice using genetically encoded nanoparticles", Nature Medicine, Nature Publishing Group, GB, vol. 21, No. 1, XP002744800, ISSN: 1546-170X, DOI: 10.1038/NM.3730, (Jan. 1, 2015), 92-98.

\* cited by examiner

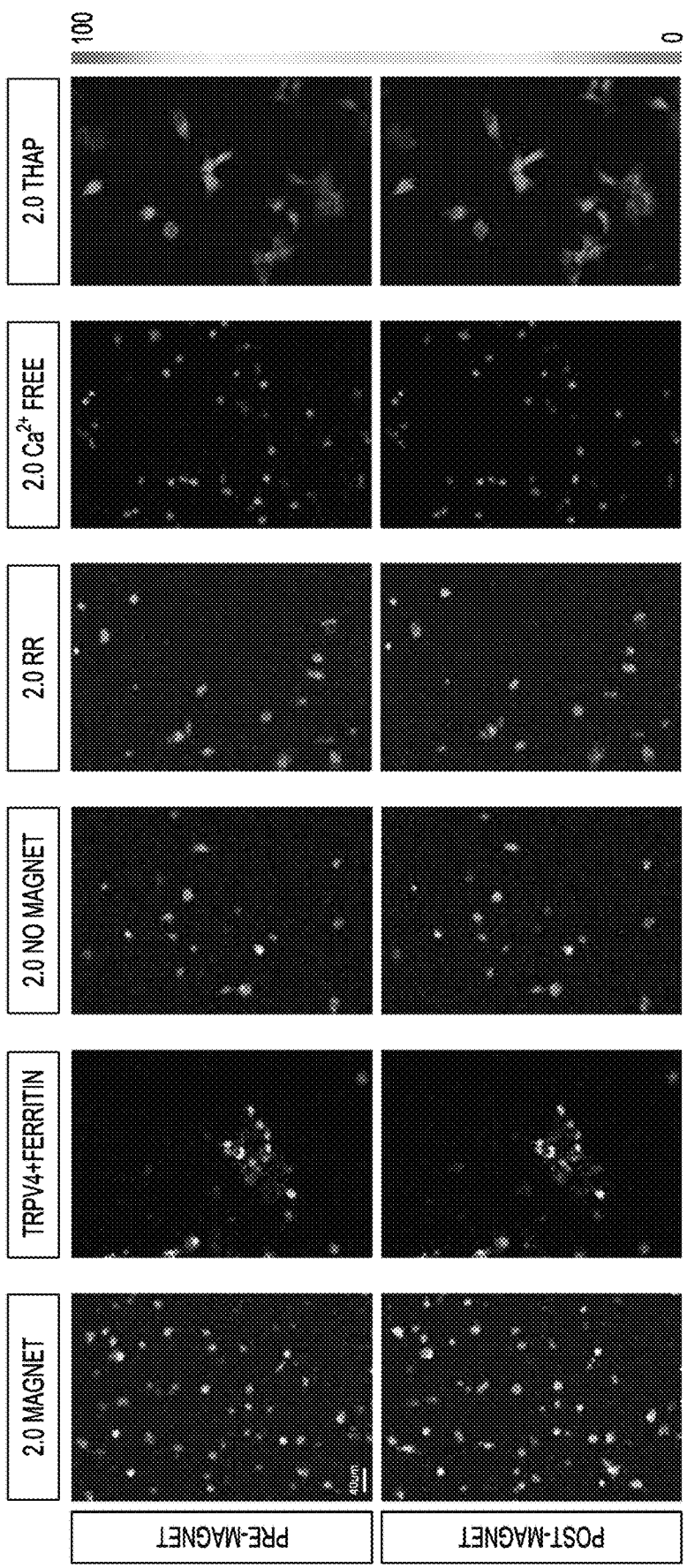

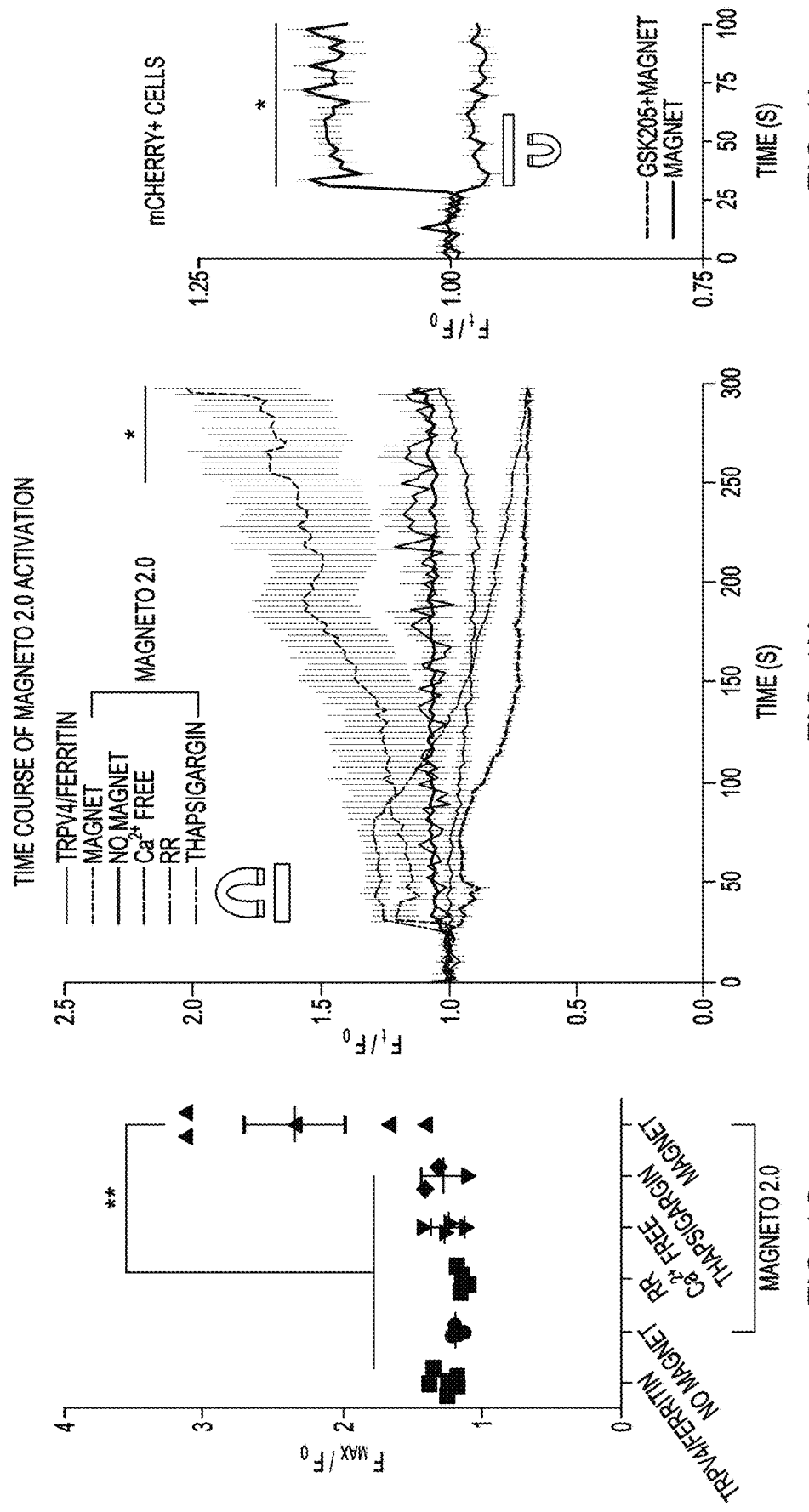

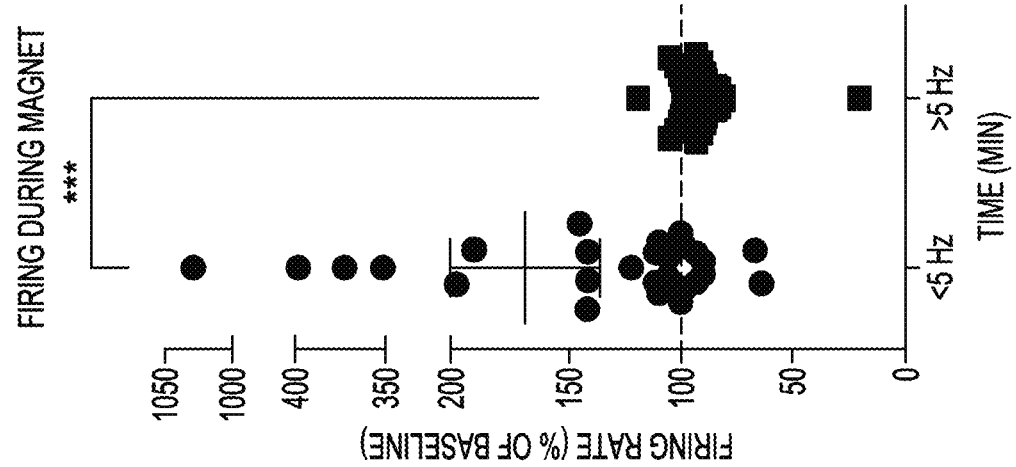
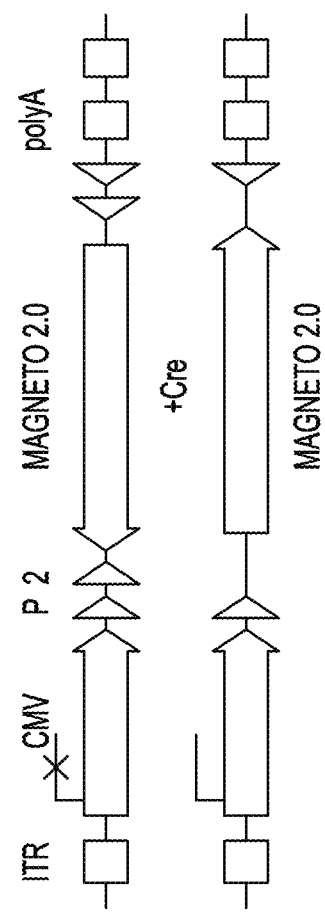
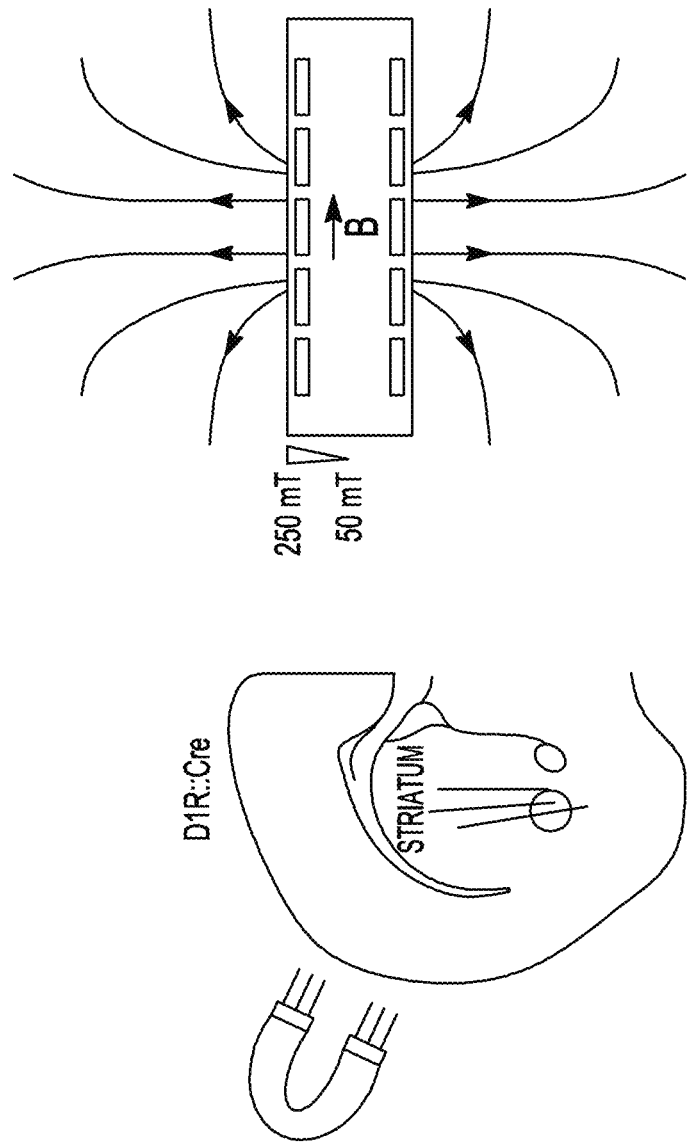
FIG. 3A
FIG. 3B
FIG. 3C
FIG. 3D

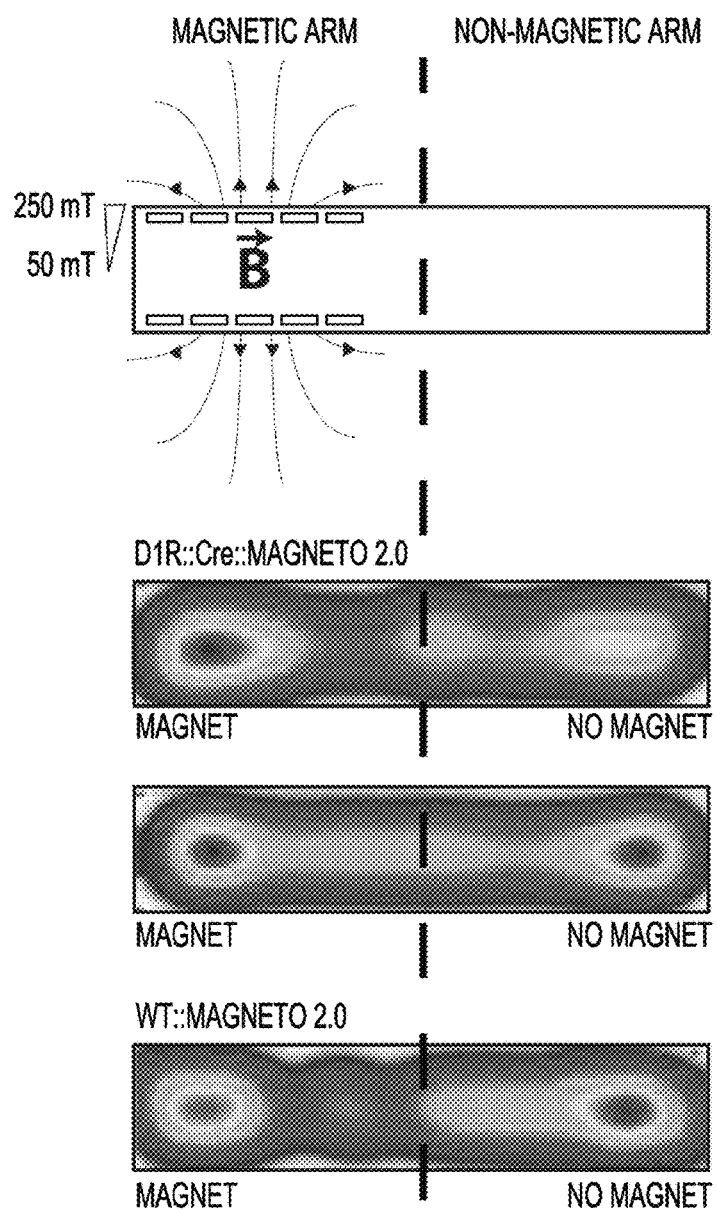
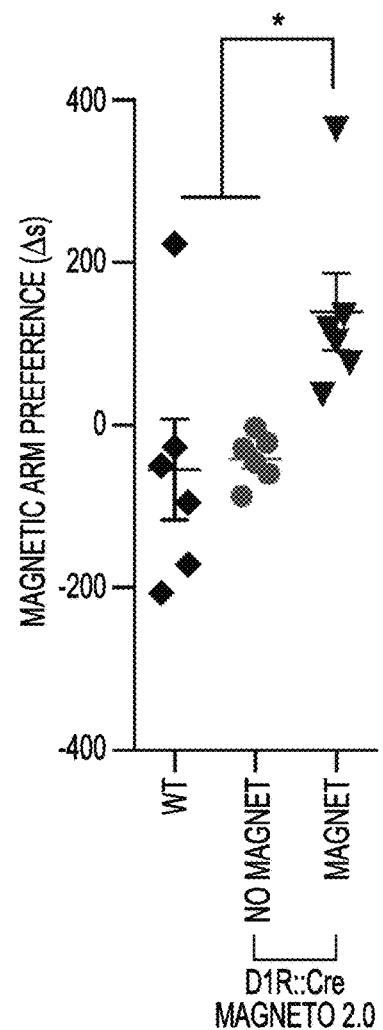
FIG. 4A
FIG. 4B

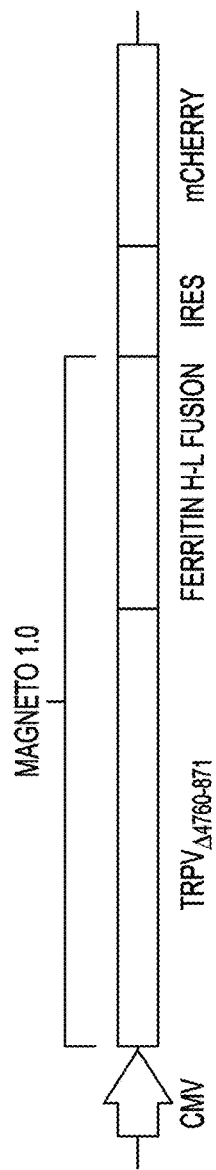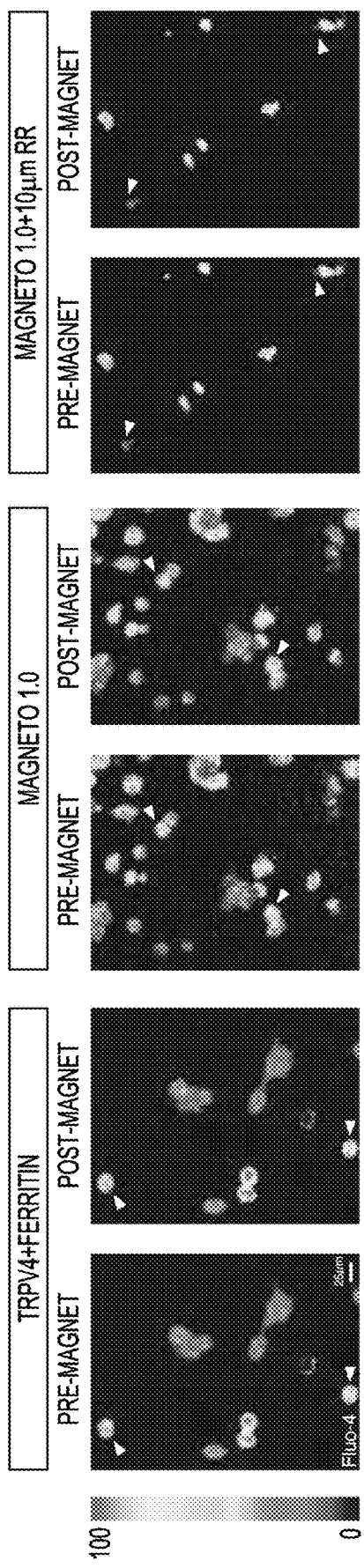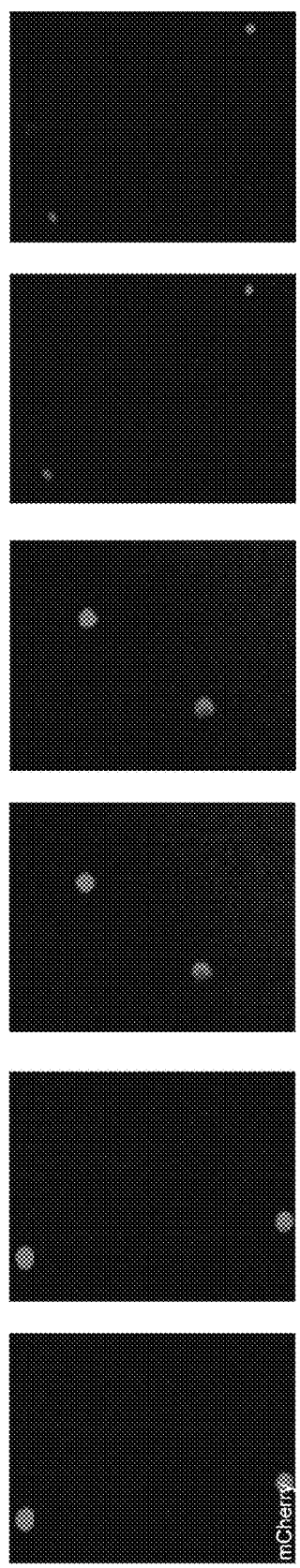
FIG. 7A
FIG. 7B  FIG. 7C  FIG. 7D  FIG. 7E  FIG. 7F  FIG. 7G

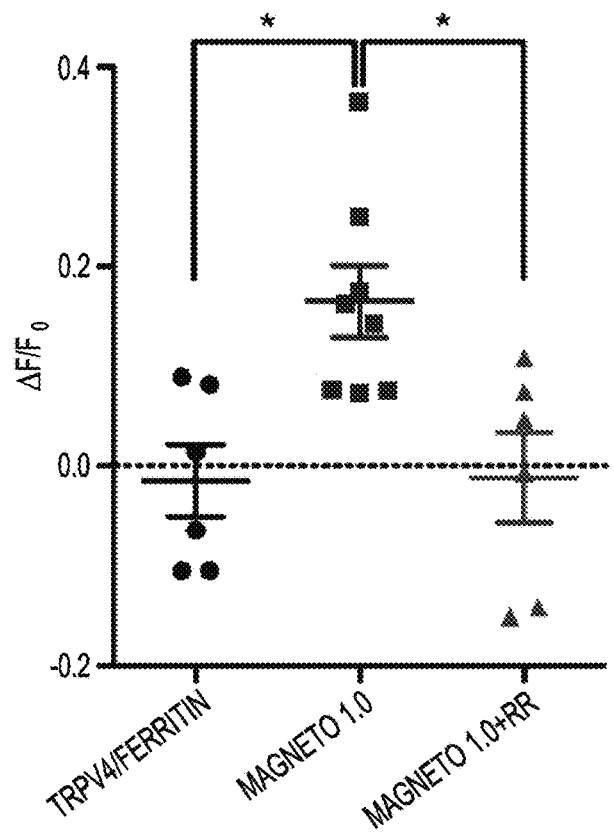
FIG. 7H
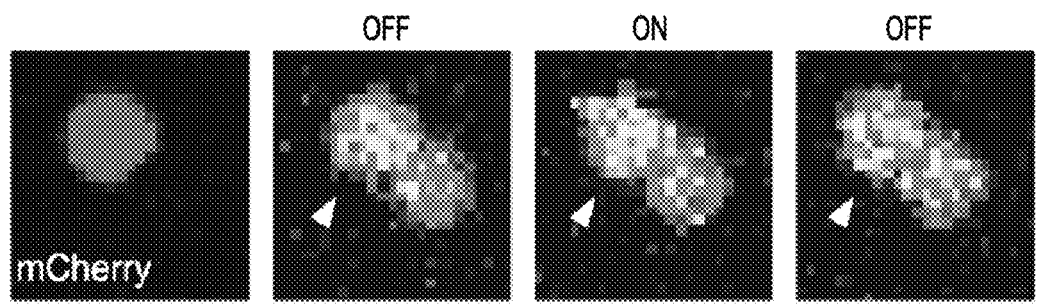
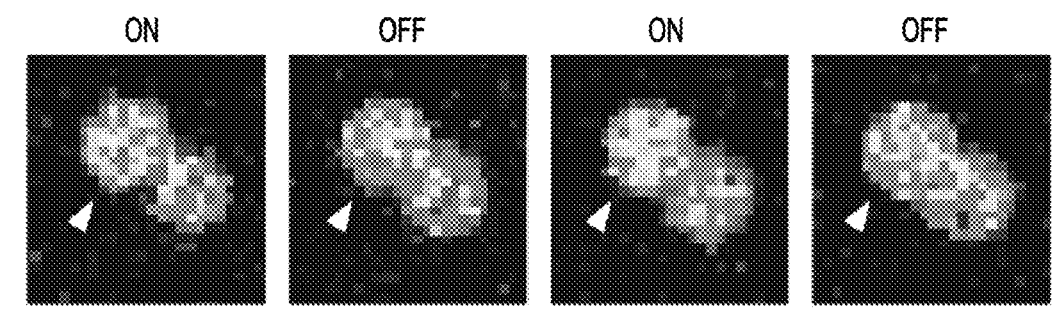
FIG. 7I

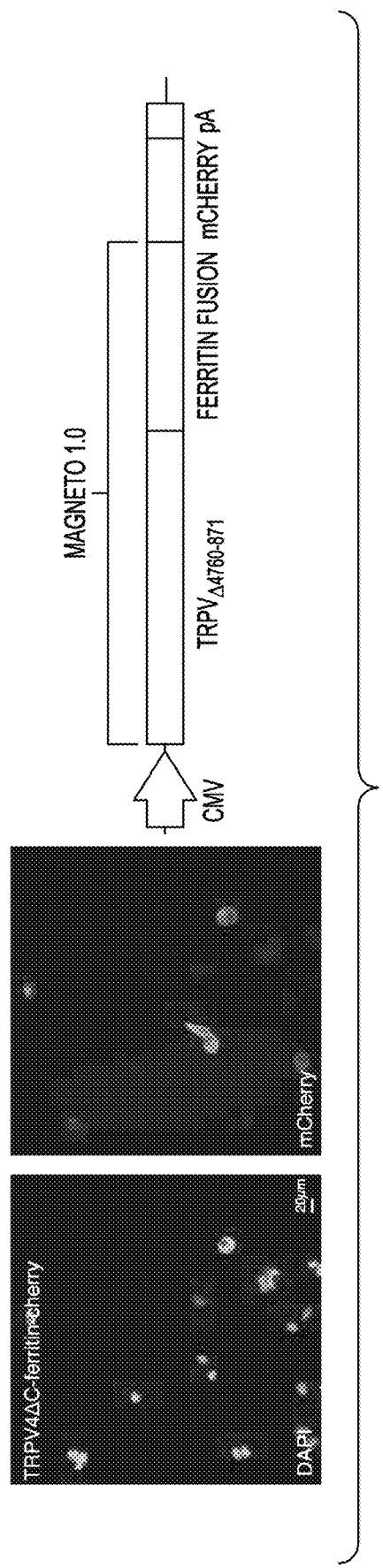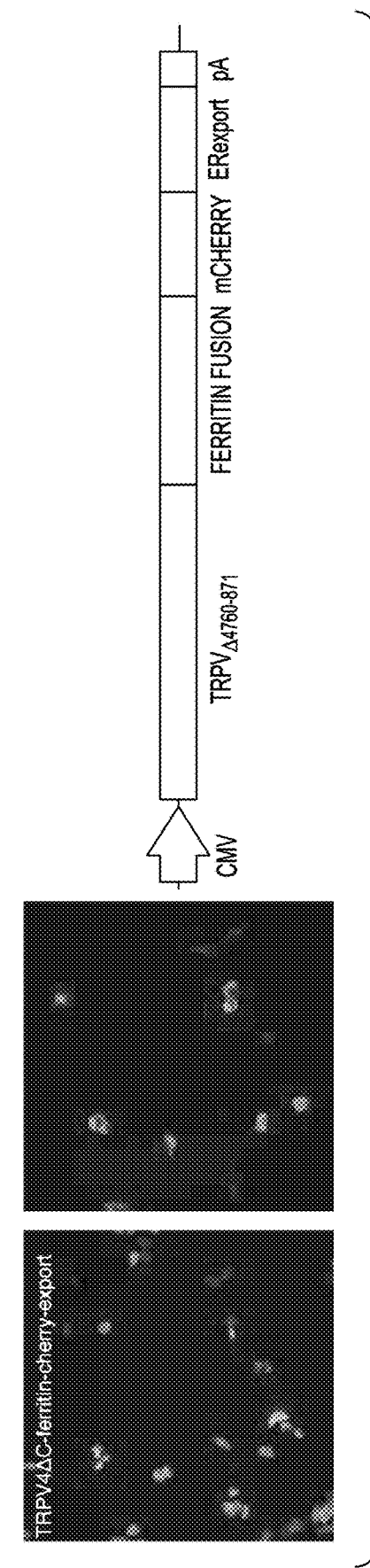
FIG. 8A
FIG. 8B

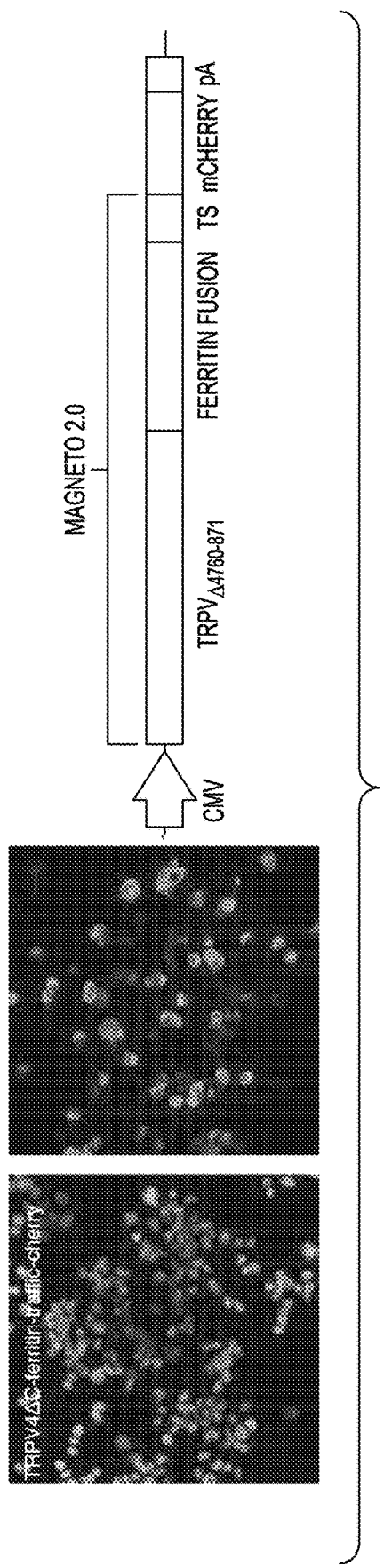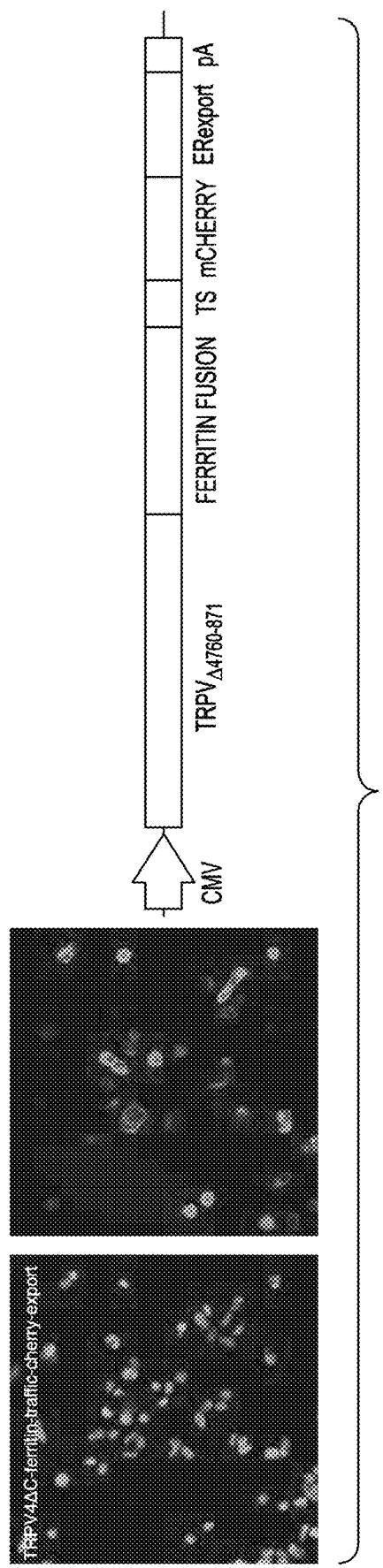

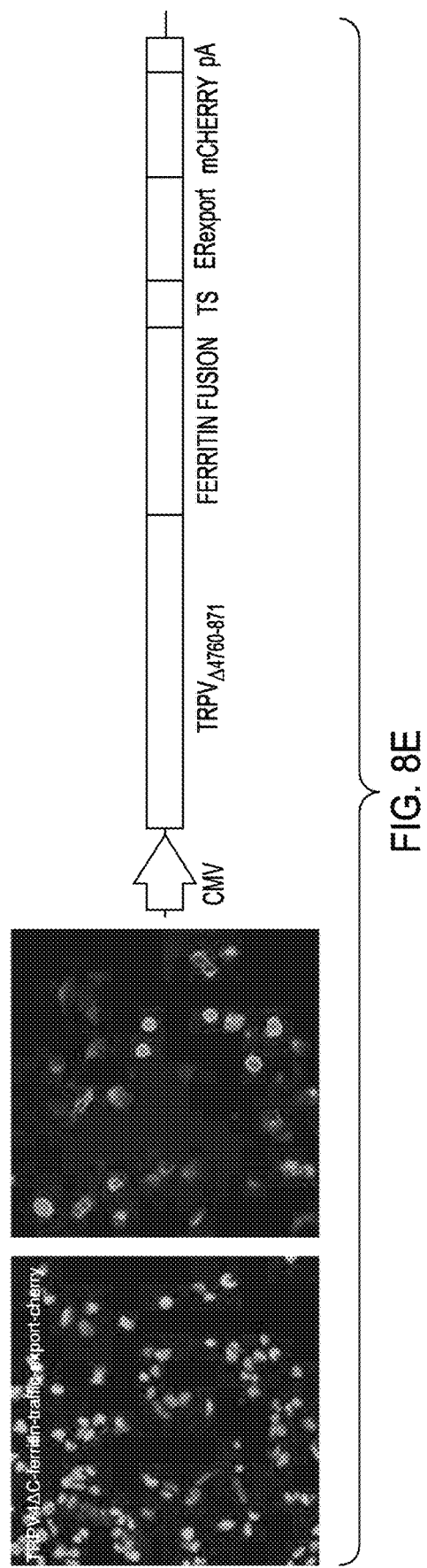

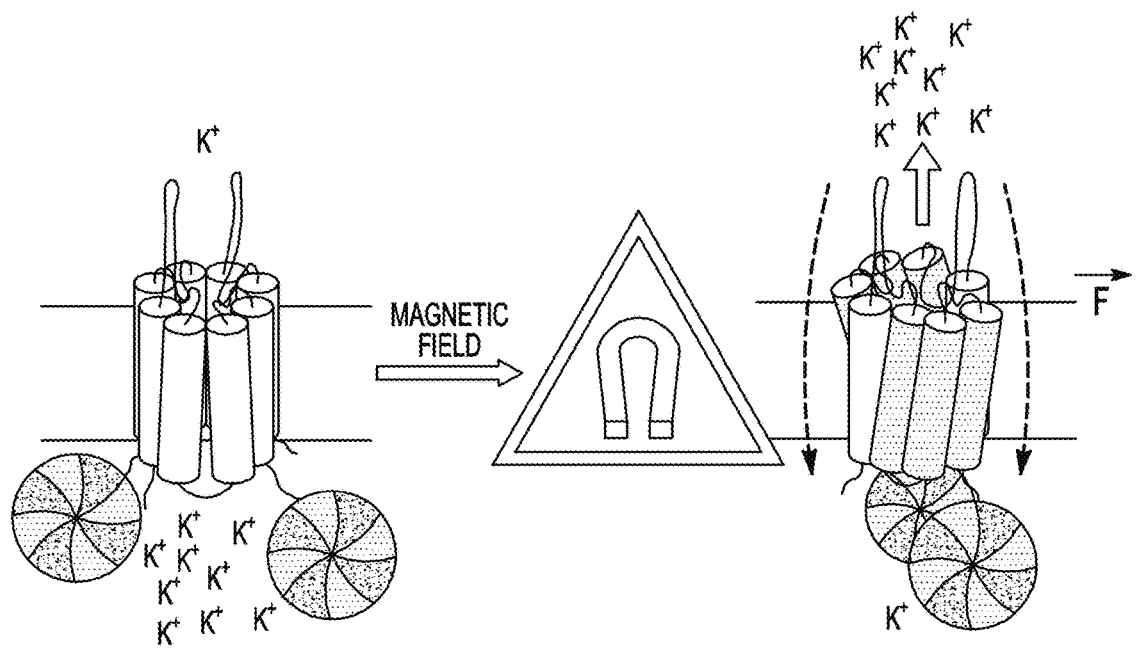
FIG. 16
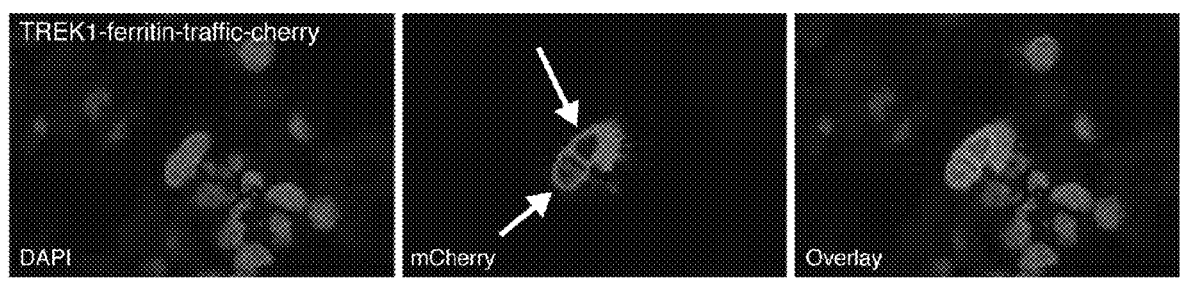
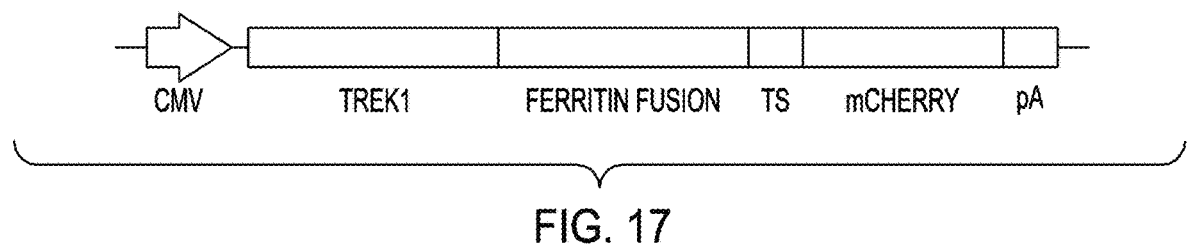
FIG. 17

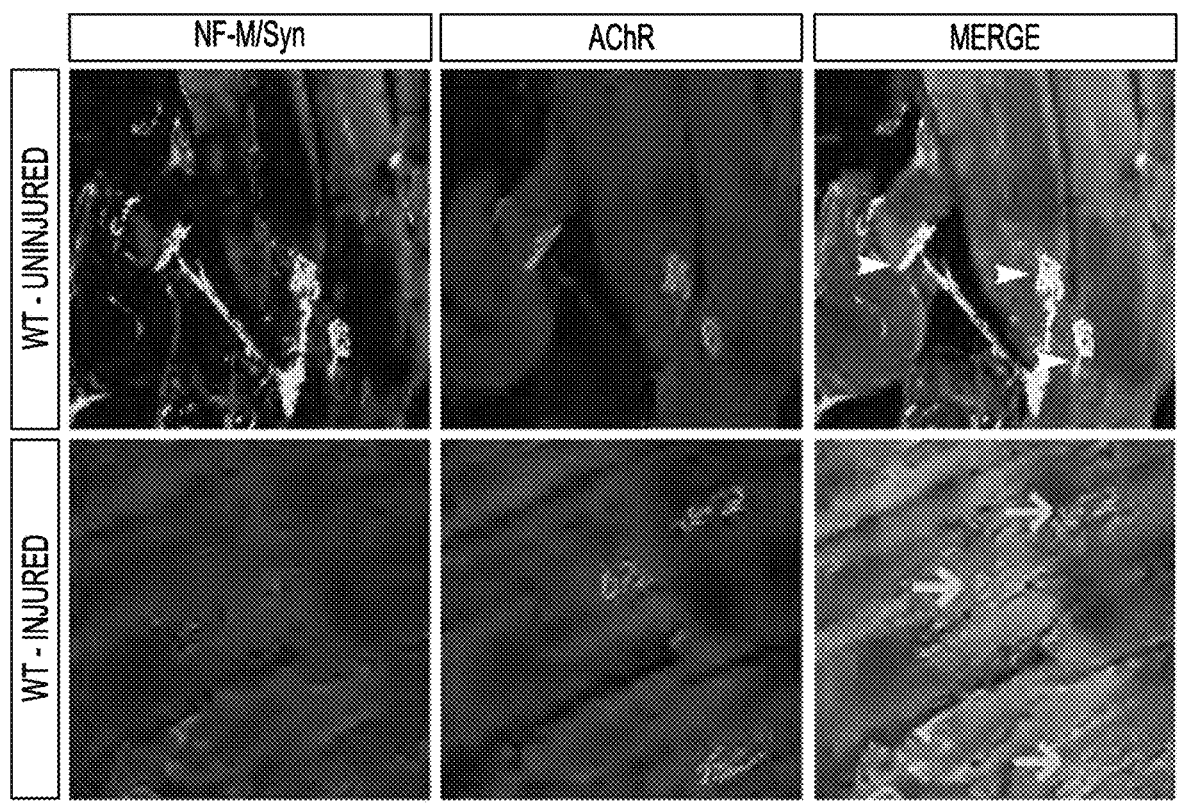
FIG. 21A
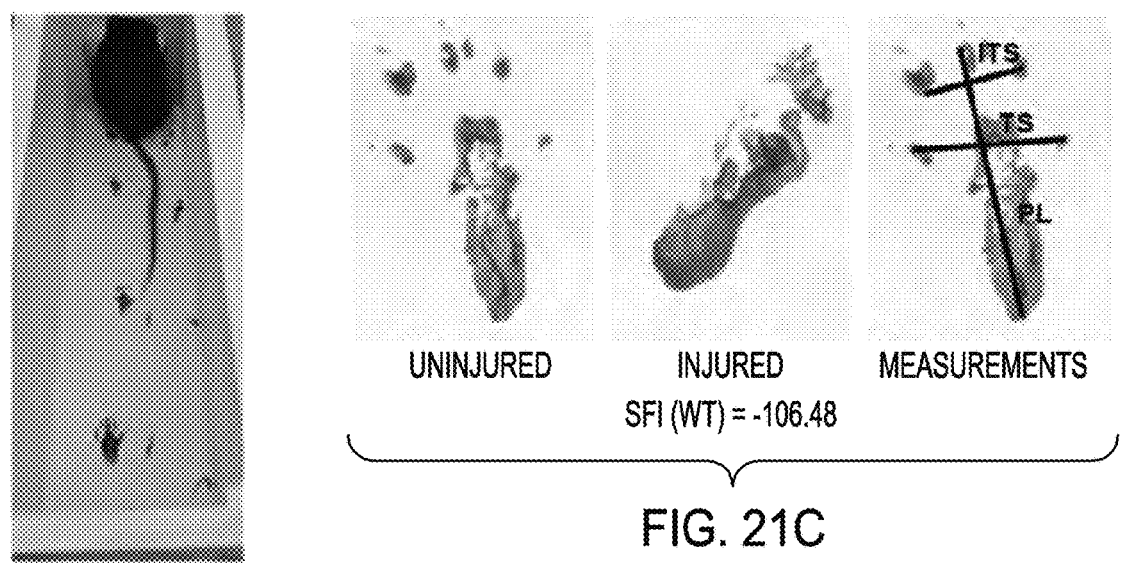
FIG. 21B
UNINJURED    INJURED    MEASUREMENTS
SFI (WT) = -106.48
FIG. 21C

COMPOSITIONS AND THEIR USE FOR CONTROLLING THE NERVOUS SYSTEM IN VIVO

CLAIM OF PRIORITY

This application is a U.S. National Stage Filing under 35 U.S.C. 371 from International Application No. PCT/US2016/058267, filed on Oct. 21, 2016, and published as WO 2017/070573, which application claims the benefit of priority of U.S. Provisional Patent Application No. 62/244,264, filed 21 Oct. 2015, the benefit of priority of which is claimed hereby, and which applications are incorporated by reference herein in their entireties.

BACKGROUND

Opto- and chemogenetic actuators have revealed properties of neural networks in normal and pathological states (1-6). While both opto- and chemogenetics remotely control neuronal stimulation, optical strategies are limited spatially because of poor light penetration into dense tissues and chemogenetic strategies suffer from slow pharmacokinetics that prevent real time cellular activation. Therefore, there remains a need for next generation actuators that are non-invasive and can respond at physiological time scales (7). To this end, several recent studies have reported engineered ion channels sensitive to a combination of radiowaves and magnetothermal heating (8-12). While these reagents represent an advance, they are multicomponent systems with possible off-target heating effects. One study has employed non-thermal magnetic control in somatic tissue for control of blood glucose (11), but a fully encoded magnetogenetic system has yet to be applied to the nervous system.

There is a long felt need in the art for compositions and methods useful for controlling behavior and for regulating deep centers of the brain. The present invention satisfies these needs.

SUMMARY OF THE INVENTION

The present application discloses compositions and methods useful for controlling behavior in animals. In one embodiment, compositions and methods are provided to control behavior magnetically. In one aspect, the nervous system is controlled. In one aspect, striatal neurons are controlled.

Disclosed herein are multiple fusion proteins that are useful for magnetogenetic control of neuronal activity and behavioral activity.

One embodiment provides a composition comprising a nucleic acid coding for a fusion protein, wherein the fusion protein comprises a channel component or a G-protein coupled receptor (GPCR) and a ferritin component. Another embodiment provides a composition comprising a fusion protein, wherein the fusion protein comprises a channel component a G-protein coupled receptor (GPCR) and a ferritin component. In one embodiment, the fusion protein is a single-component magnetogenetic actuator/a genetically encoded actuator. In one embodiment, the channel is transient receptor potential vanilloid 4 (TRPV4) or a potassium (K) channel. In another embodiment, the potassium (K) channel is TREK-1. In one embodiment, the ferritin component comprises at least two subunits of ferritin. In one embodiment, the fusion protein further comprises a membrane trafficking signal (TS). In another embodiment, the membrane trafficking signal (TS) is located on the C-terminus of the ferritin component. In one embodiment, the fusion protein further comprises an endoplasmic reticulum (ER) export signal. In one embodiment, the fusion protein is magnetically sensitive/responds to a magnet.

One embodiment provides a composition comprising a vector encoding the fusion protein described herein. In one embodiment, the vector is a bacterial vector, a viral vector or a mammalian vector. In one embodiment the viral vector is an adeno-associated virus (AAV). In one embodiment, the vector comprises a promoter, for example, a cell specific promoter. In one embodiment, the promoter is a cytomegalovirus (CMV) promoter.

One embodiment provides a recombinant host cell comprising the nucleic acid, fusion protein or vector described herein.

In one embodiment, the compositions described herein further comprise a pharmaceutically acceptable carrier and/or an additional therapeutic agent.

One embodiment provides a method to manipulate cellular activity comprising contacting a cell with a composition described herein and exposing the cell to a magnet/magnetic field. In one embodiment the contacting is in vitro. In another embodiment the contacting is in vivo. In one embodiment the cellular activity is associated with membrane protein activity. In another embodiment the cellular activity is associated with ion channel activity, such as K+ signaling. In one embodiment the cell is neural/nerve cell. In another embodiment the nerve cell is a striatal neuron. In one embodiment the magnetic field causes an increase or decrease/inhibition in neural firing.

One embodiment provides a method to treat a neural injury or disease comprising administering to a subject in need thereof a composition described herein and exposing said subject to a magnet/magnetic field. In one embodiment the composition transduces neural cells. In one embodiment the neural injury or disease is schizophrenia, autism, Parkinson's disease (PD) Huntington's disease (HD), epilepsy, Amyotrophic lateral sclerosis (ALS), catalepsy, bipolar disorder, attention deficit/hyperactivity disorder (ADHD), locked-in syndrome, migraine, multiple sclerosis (MS), physical or infectious neuron/brain trauma (e.g., accident, surgery, viral, meningitis), neuron degeneration, stroke, basal ganglia disease, dyskinesia, tremor, restless legs, cerebral palsy, coma, concussion, dementia, ataxia, locked-in syndrome (LiS), narcolepsy, Prader-Willi Syndrome, sleep disorders, Asperger Syndrome, pain, Creutzfeldt-Jakob Disease, cumulative trauma disorders, Cushing's Syndrome, diabetic neuropathy, diffuse sclerosis, seizures, and/or spinal cord injury.

One embodiment provides a method to treat or repair nerve damage comprising administering to a subject in need thereof a composition described herein and exposing said subject to a magnet/magnetic field.

One embodiment provides a method to control nerve cells firing comprising administering to a subject in need thereof a composition described herein and exposing said subject to a magnet/magnetic field.

One embodiment provides a method to control behavior in a subject comprising administering to said subject a composition described herein and exposing said subject to a magnet/magnetic field. In one embodiment the behavior is reward behavior, open filed behavior and/or movement.

One embodiment provides a method to control dopamine receptors in a subject comprising administering to said subject a composition described herein and exposing said subject to a magnet/magnetic field. In one embodiment the receptor is D1R. In one embodiment the striatal cells are being controlled.

In one embodiment, the present application discloses a fusion protein that is a single-component magnetogenetic actuator, wherein the fusion protein comprises a cation channel component and a ferritin component. In one aspect, the cation channel component is transient receptor potential vanilloid 4 (TRPV4). In one aspect, the fusion protein comprises two subunits of ferritin.

Optionally, a fusion protein of the invention may also comprise a membrane trafficking signal. Optionally, a fusion protein of the invention may also comprise an ER export signal.

In one embodiment, the present application discloses compositions and methods useful for transforming ion channels into magnetic field detectors.

In one embodiment, the present application discloses compositions and methods useful for studying and identifying neural circuits.

In one embodiment, the fusion protein of the invention is magnetically sensitive.

In one embodiment, the fusion protein of the invention is a genetically encoded actuator. In one aspect, the fusion protein can be used to manipulate cellular activity in vitro. In one aspect, the fusion protein can be used to manipulate cellular activity in vivo. In one aspect, the cellular activity is associated with membrane protein activity. In one aspect, the cellular activity is associated with ion channel activity.

In one embodiment, the present invention provides a vector encoding a fusion protein of the invention. In one aspect, the vector is an AAV. Various promoters can be used. In one aspect, the promoter is a CMV promoter.

A fusion protein of the invention is capable of activating a large nucleus deep within the brain. In one aspect, striatal neurons can be transduced using a viral vector encoding a fusion protein of the invention.

In one aspect, a protein of the invention is Magneto2.0.

In one aspect, a fusion protein of the invention comprises a membrane trafficking signal. In one aspect, the fusion protein comprises an ER export signal. In one aspect, the fusion protein of the invention comprises both a membrane trafficking signal and an ER export signal.

In one embodiment, an expression vector comprising a nucleic acid sequence encoding a fusion protein of the invention can be administered to a subject. In one aspect, the vector is an AAV. In one aspect, the expression vector can be used to transduce neurons in the brain of the subject. Following administration, the transduced cells of the subject can be exposed to magnetic stimulation. In one aspect, a nucleus deep within the brain is transduced. In one aspect, the fusion protein is Magneto2.0.

In one embodiment, Magneto2.0 is capable of controlling neural firing in response to magnetic fields. In one aspect, the control is in a deep brain region.

Other fusion proteins of the invention can be similarly transduced as proteins or as expression vectors encoding the proteins.

The present application further discloses compositions and methods for preparing and testing additional fusion proteins useful for controlling neural firing in response to magnetic fields. In one aspect, the compositions and methods are also useful for preparing and testing fusion proteins to be transduced into other tissue and cell types in the body. In one aspect, a fusion protein can be prepared and administered such that it controls behavior upon being exposed to a magnetic field.

The present invention provides compositions and methods for controlling dopamine receptors. In one aspect, the receptor is D1R. In one aspect, the methods allow for controlling striatal cells.

In one embodiment, the compositions and methods of the invention are useful for remotely controlling complex mammalian behaviors mediated by deep brain nuclei.

In one embodiment, the present invention provides a magnetogenetic inhibitory actuator. In one aspect, the actuator comprises an ion channel protein tethered to a paramagnetic protein. In one aspect, the ion channel is a potassium (K) channel. In one aspect, the paramagnetic protein is ferritin. In one aspect, the method is useful for generating a magnetically sensitive ion channel. In one aspect, the invention provides a TREK1-ferritin fusion protein. In one aspect, an actuator fusion protein of the invention further comprises a membrane trafficking signal (TS). In one aspect, the TS is on the ferritin fusion gene C-terminus. In one aspect, the TREK1-ferritin-TS fusion protein is called Professor X (ProfX).

In one aspect, an expression vector comprising a nucleic acid sequence encoding ProfX can be administered to a subject or contacted with a cell. In one aspect, ProfX localizes to the plasma membrane. In one aspect, when exposed to a magnetic field ProfX hyperpolarizes the cells. In one aspect, K signaling can be controlled.

An ion channel fusion protein of the invention responds to magnetic fields.

In one aspect, the actuator fusion protein of the invention is inhibitory upon being subjected to a magnetic field. In one aspect, it can inhibit neuronal activity in cells expression the actuator.

The actuator fusion protein can be encoded by a sequence in an expression vector. In one aspect, the vector is AAV.

Various types of behavior can be controlled by the methods of the invention, including, but not limited to, reward behavior, open field behavior, and/or movement.

The present invention further provides a vector comprising an isolated nucleic acid comprising a nucleic acid sequence encoding a fusion protein of the invention and optionally a promoter. In one aspect, the vector is selected from the group consisting of a bacterial vector, a viral vector, and a mammalian vector. In one aspect, the invention provides for administering the nucleic acid to a subject or to a cell. The invention further provides a recombinant host cell comprising an isolated nucleic acid of the invention and a recombinant host cell comprising a vector the invention.

The present invention provides a fusion protein encoded by an isolated nucleic acid of the invention.

The present invention further provides compositions and methods for making fusion peptides of the invention and for making isolated nucleic acids comprising sequences encoding the peptides.

The present invention further provides a pharmaceutical composition comprising a fusion protein of the invention or an expression vector encoding a fusion protein of the invention. The composition optionally comprises a pharmaceutically acceptable carrier. The composition may also optionally comprise an additional therapeutic agent.

The present invention further provides compositions and methods for treating diseases and disorders.

Various aspects and embodiments of the invention are described in further detail below.

BRIEF DESCRIPTION OF THE DRAWINGS

FIGS. 1A-I: Remote control of cellular signaling using Magneto2.0. (a-f) In vitro calcium imaging micrographs of Fluo-4-loaded HEK293 cells before and after 3 pulses of 40-50 mT, 0.1 Hz, 90% duty cycle magnetic stimulation. (g) Quantification of calcium fluorescence fold change in response to the given condition. All experiments treated with magnetic fields except "no magnet" condition. Shown are n=3-5 coverslips per condition, n=114-396 total cells analyzed per condition, n>30 cells analyzed per coverslip. One-way ANOVA, Bonferronipost-test, ($F_{4,16}$=7.268, p=0.0016). (h) Average temporal kinetics of all cells analyzed within a single coverslip per condition. Horizontal bar/horseshoe indicates magnetic field application. (i) Kinetics of calcium fluorescence fold change within mCherry+ cells in response to magnet in the presence or absence of the TRPV4 inhibitor, GSK205. n=3 coverslips per condition. Data represent all mCherry+ cells analyzed (n=87 GSK205-treated, n=57 untreated). Two-way ANOVA, Bonferroni post-test. Data shown as mean±SEM. $p<0.01$

FIGS. 3A-G: Magnetogenetic control of the mammalian nervous system in vivo. (a) Schematic of viral vector. ITR: inverted terminal repeats; CMV: cytomegalovirus promoter; P: loxP site; 2: lox2272 site. (b) Representation of magnetic stimulation and recording of D1R-expressing cells in the striatum of D1R::Cre mice. Solid lines indicate electrode placement, n=3 mice; dashed circle indicates approximate injection area. (c) Cartoon of magnetized testing chamber, rare earth magnets (gray bars) are embedded in the walls, "B" represents magnetic field; strength shown as gradient. (d) Quantification of average firing rate during magnetic field exposure in freely behaving mice, unpaired two-tailed t-test, ($t_{96}$=3.461, p=0.0008). (e) Proportion of cells firing >5% over baseline during magnet exposure. (f) Standard score (z-score) over time for MSNs in (e) that fired >5% (red, n=17) vs. <5% (black, n=13). Two-way ANOVA ($F_{1,3360}$=47.67, $p<0.0001$). (g) Proportion of cells firing >5% over baseline post-magnet exposure. n=30<5 Hz neurons, n=69>5 Hz neurons from 3 mice. Data are shown as mean±SEM, ***$p<0.001$.

FIGS. 4A-B: Activation of striatal D1R+ neurons control reward behavior. (a) Cartoon of magnetized RTPP assay. (b-c) Representative heat maps of arm preference for each condition shown as time spent in a particular arm; mid-point of one mouse shown per map, (d) Difference in time spent in magnetic arm versus non-magnetic arm for WT and D1R::Cre mice transduced with AAV::Magneto2.0. "No magnet" refers to nonmagnetized RTPP chamber, "magnet" refers to magnetized chamber, WT mice were only tested in the magnetized chamber. One-way ANOVA, Bonferroni post-test, ($F_{2,15}$=5.611, p=0.0152). Data are shown as mean±SEM. *$p<0.05$.

FIGS. 7A-I: In vitro calcium imaging using Magneto1.0. (a) Mammalian expression vector for Magneto1.0. (b-g) Representative images of HEK293 cells used for in vitro magnetostimulation Fluo-4 calcium imaging. (h) Quantification of relative calcium fluorescence in response to magnetic stimulation of mCherry+ cells, n=437-540 cells per condition. (i) Representative images of temporal association between calcium fluorescence and magnetic field pulses in an individual Magneto1.0-expressing cell (arrow), Field was pulsed for alternating 10 second periods of on/off Data are shown as mean±SEM, statistics determined by one-way ANOVA, Bonferroni post-test, ($F_{2,17}$=7.509, p=0.0046). *$p<0.05$.

FIGS. 8A-E: Optimization of Magneto1.0 by improving cellular trafficking. (a-c) HEK293 cells transfected with mCherry-fused variants of Magneto1.0 with combinations of various inwardly rectifying K+ channel 2.1 (Kir2.1) trafficking signals. (a) Magneto1.0-mCherry shows diffuse cellular localization, poor membrane expression, and poor transfection efficiency. (b) Addition of ER export signal from Kir2.1 to C-terminus of Magneto1.0-mCherry partially improves Magneto expression. (c) Addition of Kir2.1 membrane trafficking signal (TS) significantly improves membrane expression of Magneto. (d) Dual addition of membrane trafficking and ER export signals improves expression relative to Magneto1.0 but not relative to a single membrane trafficking signal. (e) Tandem Kir2.1 membrane trafficking/ER export signals on ferritin C-terminus improves expression but not relative to (c). n=2 coverslips and >100 cells per trafficking modification examined.

Magneto1.0 fish. Statistics determined by Chi-squared analysis, (Chi$^2_3$=36.51, p<0.0001). (d) Quantification of coiling rate in WT (uninjected) and β-actin::Magneto1.0 expressing zebrafish. Replicates (number of individual fish) shown in columns. Statistics determined by one-way ANOVA, Bonferroni post-test, ($_{F3,64}$=3.89, p=0.0129). ***p<0.001, *p<0.05. Data are shown as mean±SEM.

Figure 12A:
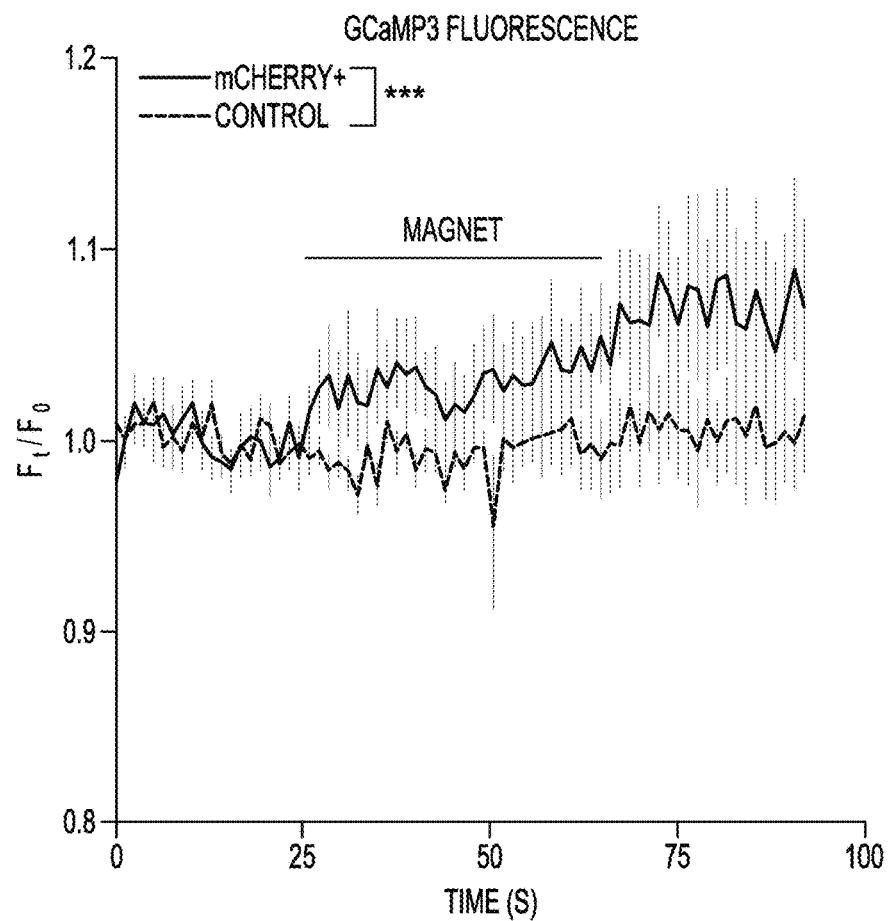
Figure 12B:
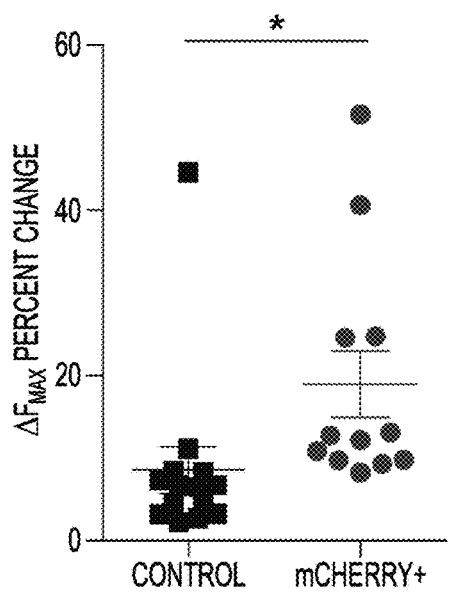

FIGS. 12A-B: GCaMP3 calcium imaging in live zebrafish. (a) Quantification of GCaMP3 fluorescence in Rohon-Beard sensory neurons. (b) Maximal calcium fluorescence change of mCherry+ and mCherry− cells in response to magnetic field stimulation.

Figure 13A:
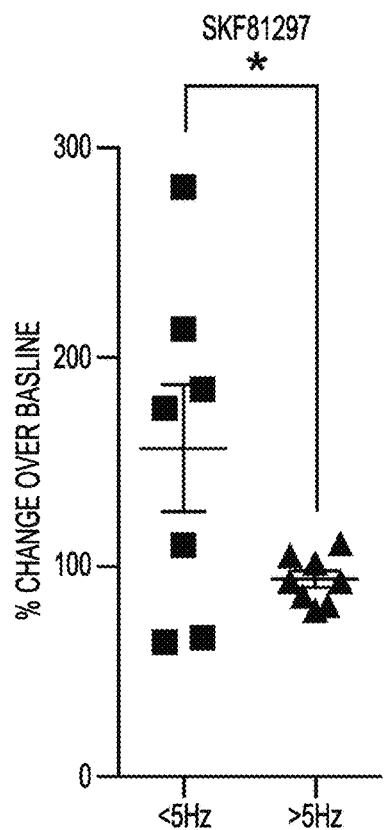
Figure 13B:
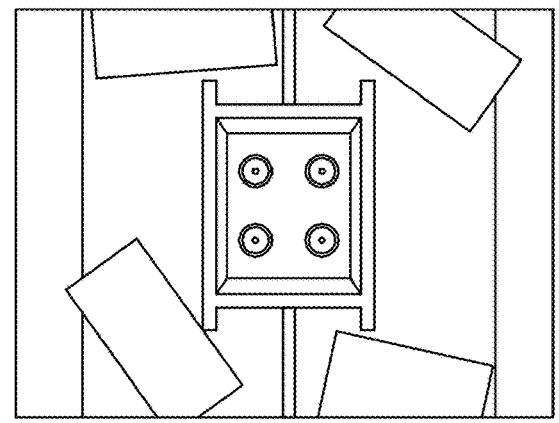
Figure 13C:
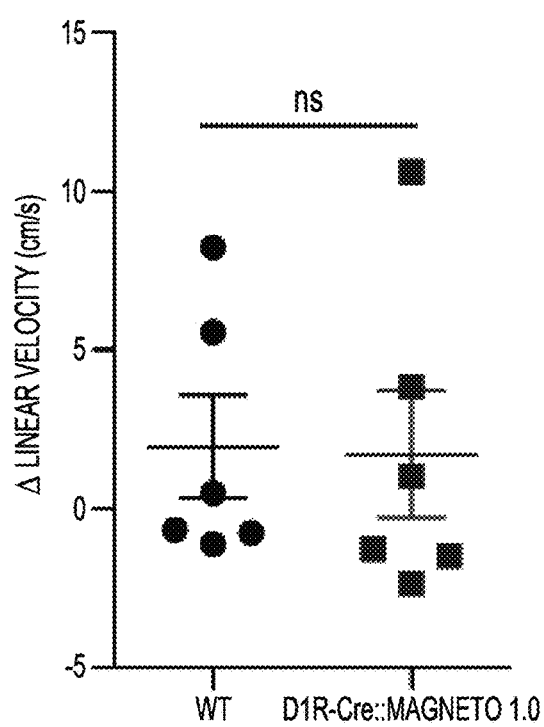

FIGS. 13A-C: Mouse behavioral controls. (a) Quantification of the change in firing rate relative to baseline for low-frequency and high-frequency firing neurons in the striatum in response to the D1R agonist SKF81297, n=7-8 neurons examined per condition from one D1R::Cre mouse transduced with CMV::DIO-Magneto2.0, unpaired two-tailed t-test, ($t_{1,3}$=2.192, p=0.0472). (b) Picture of magnetic open field behavioral chamber. (c) Quantification of change in linear velocity before and during magnetic stimulation for both groups, unpaired two-tailed t-test, ($t_{10}$=0.08856, p=0.9312). *p<0.05, ns: not significant.

FIGS. 14A-H: ProfX controls K+ signaling in vitro (a-f) In vitro micrographs depicting fluorescence of the K+-binding dye APG-2 in ProfX-transfected HEK293 cells before and after magnetic stimulation. (g) Quantification of K+ fluorescence fold change in response to magnetic stimulation. Bottom three minimum values were averaged and divided by baseline fluorescence. Replicates in graph are averaged among coverslips with >20 cells analyzed per coverslip. (h) Time course of K+ fluorescence in response to magnetic stimulation. Colors indicate same conditions in (g). *p<0.05. Data shown are mean±SEM.

FIGS. 15A-E: Magnetogenetic inhibition of zebrafish behavior in vivo (a) Schematic depicting the behavioral paradigm and transgenesis vector used to test zebrafish behavior. Fish mosaically expressing ProfX were placed in a bath of 250 μM allyl isothiocyanate (AITC), and were either treated or untreated with magnetic fields. (b-c) Quantification of the mobility characteristics of zebrafish expressing ProfX pan-neuronally either with or without magnetic field application. (d-e) Quantification of the movement characteristics of zebrafish expressing ProfX in motoneurons shown as (d) pairwise within magnetic field treated group and (e) change in movement between magnetic field treated and untreated groups.

FIG. 16: Schematic of ProfX structure and function Schematic depicting the ProfX construct structure, which is composed of the stretch-sensing K+ channel TREK-1 and the paramagnetic iron storage protein, ferritin. Upon exposure to magnetic fields, ProfX is stretched and hyperpolarizes the cell.

FIG. 17: ProfX localizes to the plasma membrane in mammalian cells. Immunofluorescence indicating the subcellular localization of ProfX in transfected HEK293 cells. Arrows indicate plasma membrane localization. Below: mammalian expression construct containing ProfX (TREK1-ferritin fusion gene) consisting of a C-terminal plasma membrane trafficking signal and mCherry tag fused to ferritin.

Figure 18A:
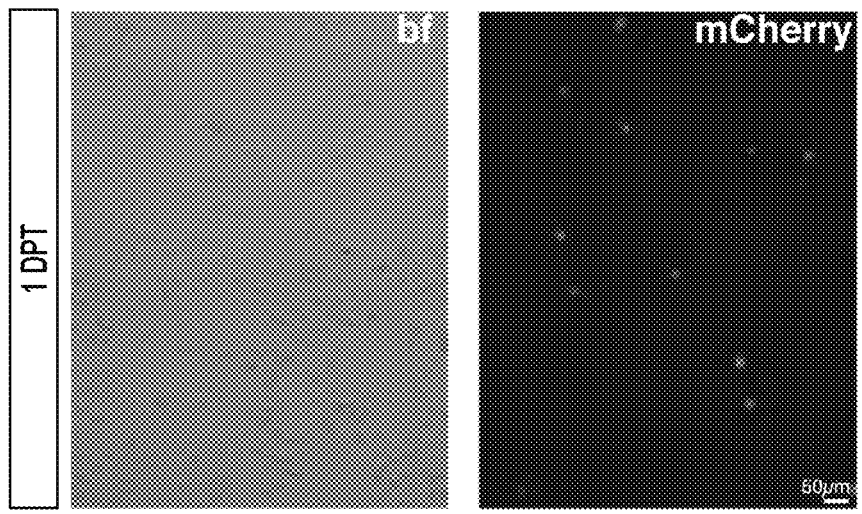
Figure 18B:
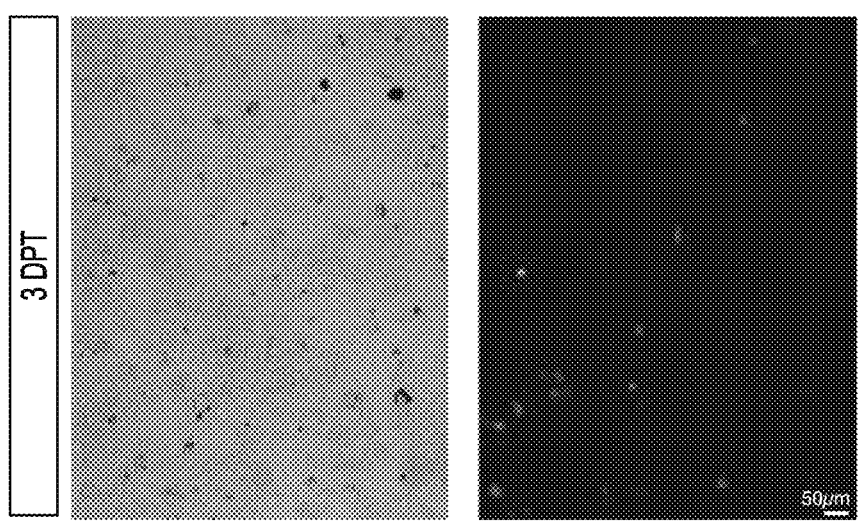
Figure 18C:
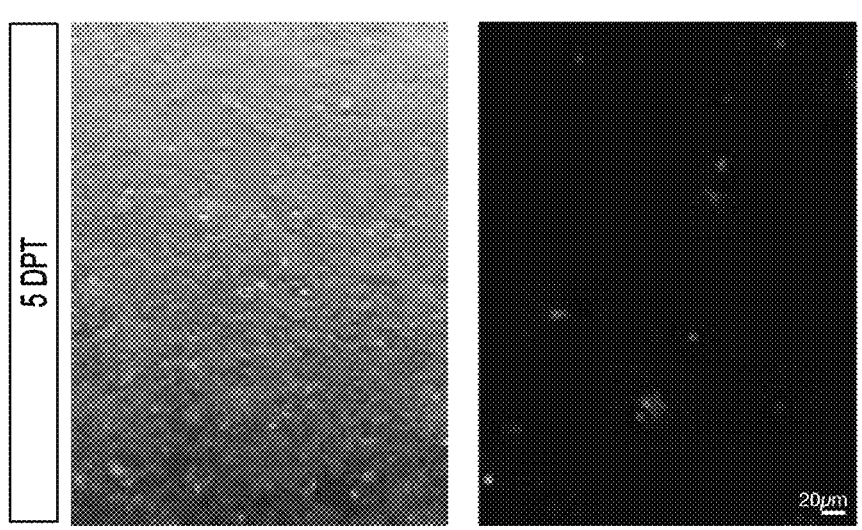

FIGS. 18A-C: Tolerance of ProfX in mammalian cells (a-c) Analysis of ProfX stability over time in transfected HEK293 cells. Shown are 1, 3, and 5 days post-transfection (DPT) using cells transfected with ProfX-p2A-mCherry.

Figure 19A:
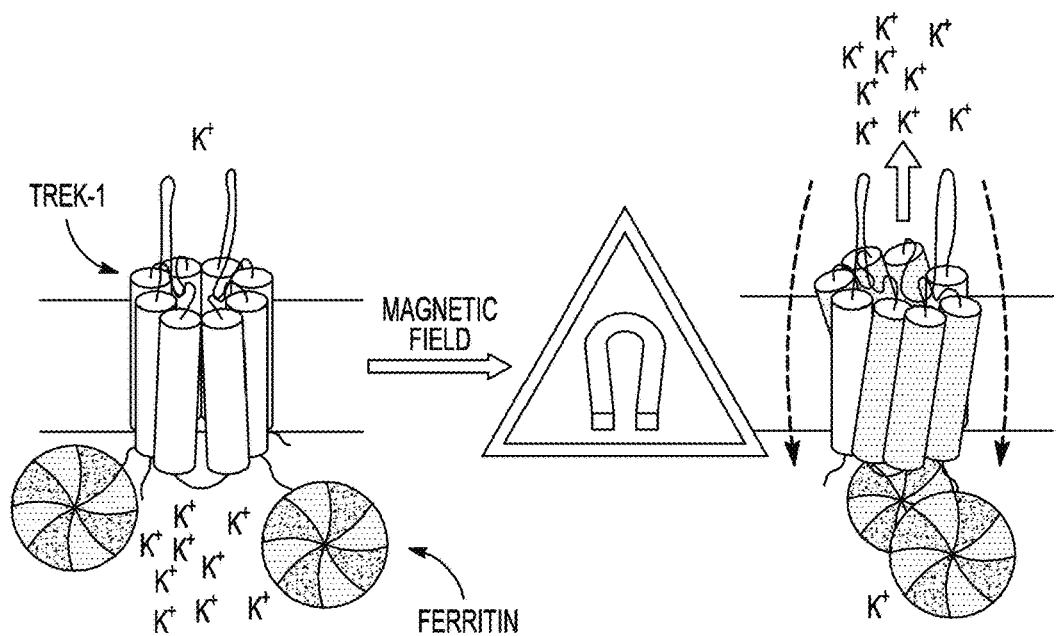
Figure 19B:
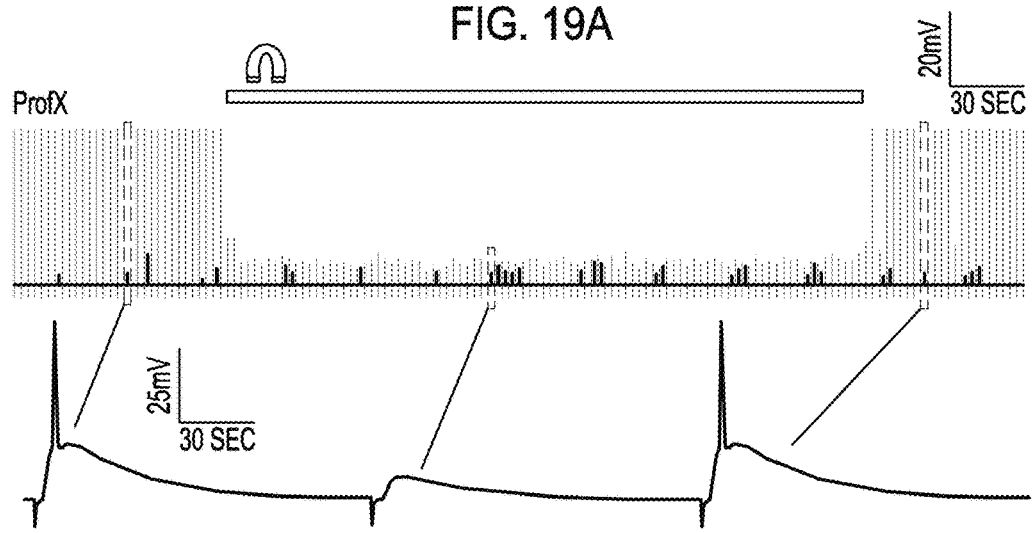
Figure 19C:
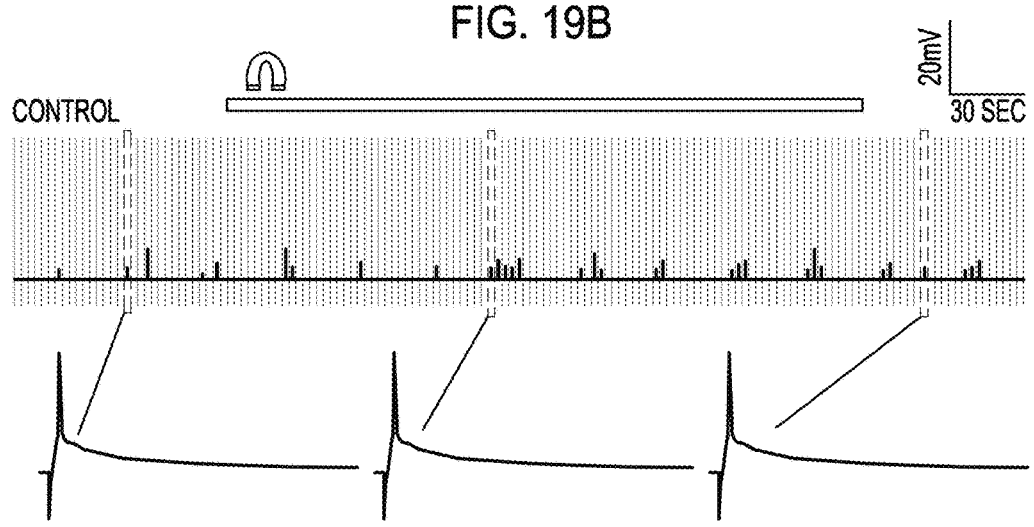

FIGS. 19A-C Schematic of TREK-1-ferritin fusion (ProfX), a potassium channel controlled by magnetic fields.

b-c. Magnetic field application blocks action potentials in CA1 neurons expressing ProfX (b), but not control neurons (c).

Figure 20A:
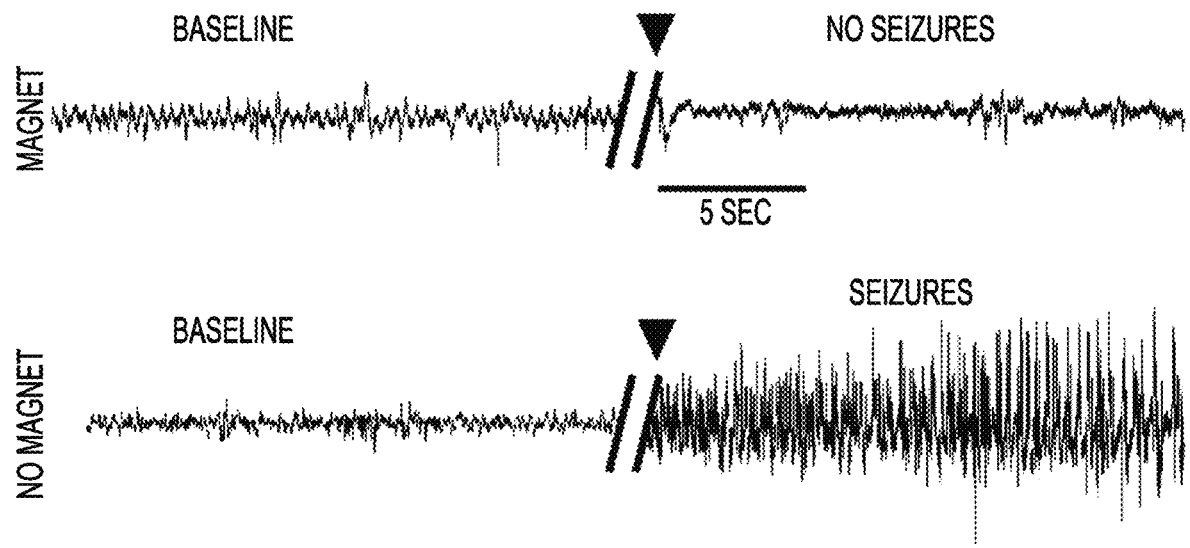
Figure 20B:
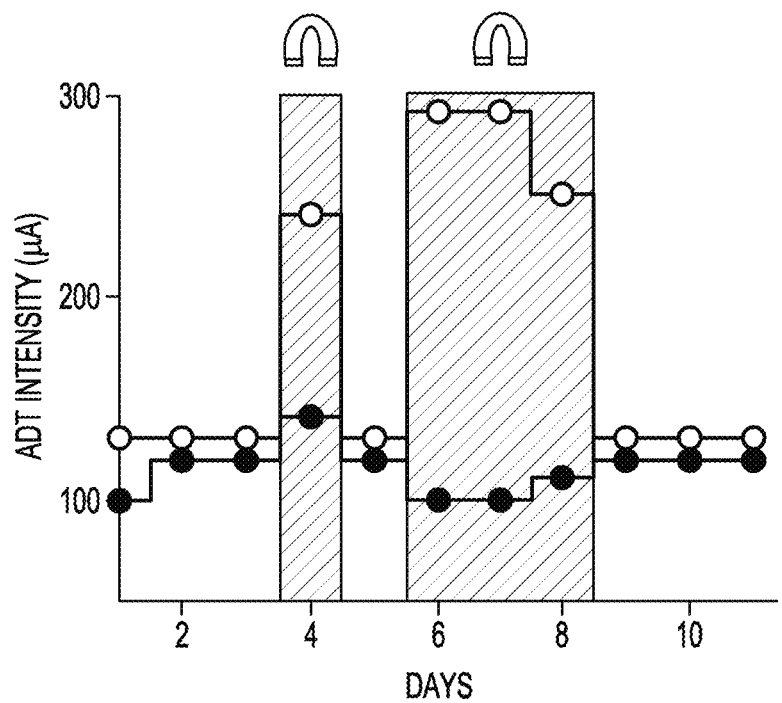

FIGS. 20A-B a. EEG (electroencephalogram) recordings from electrically induced (arrowheads) seizures of a mouse expressing ProfX in the hippocampal neurons is inhibited by magnetic field application (top panel). In the absence of a magnetic field, ictal episodes are observed in this mouse upon identical electrical stimulation (bottom panel). b. The intensity of electrical current that induces a seizure is increased during magnetic stimulation (grey boxed days) in ProfX expressing mouse (red), but not in control GFP expressing mouse (black). Note the removal of the magnetic field reverses the seizure threshold intensity to basal levels in ProfX expressing mouse.

FIGS. 21A-E Functional recovery. A Neuro Muscular Junction (NMJ) staining in Tibialis Anterior (TA) muscles. Red, AChR (postsynapse/muscle), Green, NF-M, Synaptophysin (presynapse) for WT before and 3 days after sciatic nerve transection. White arrowheads show fill occupancy and blue arrows show no occupancy. B. A mouse in walking track apparatus. C. Foot prints of a wild type mouse before and 3 days after sciatic nerve transection. Measurements include PL=Print Length, TS=Toe Spread, ITS=Intermediary Toe Spread. SFI is calculated according to SFI=−38.3[(EPL-NPL)/NPL]+109.5 [(ETS-NTS/NTS]+13.3[(EITS-NITS)/NITS]−8.9. N=Normal, E=Experimental. D. Hargreaves radiant heat test. E. Von Frey test measuring reflexive thermal pain threshold (D) and mechanical acuity (E) for wild type animals. Data representing mean±SEM.

Figure 22A:
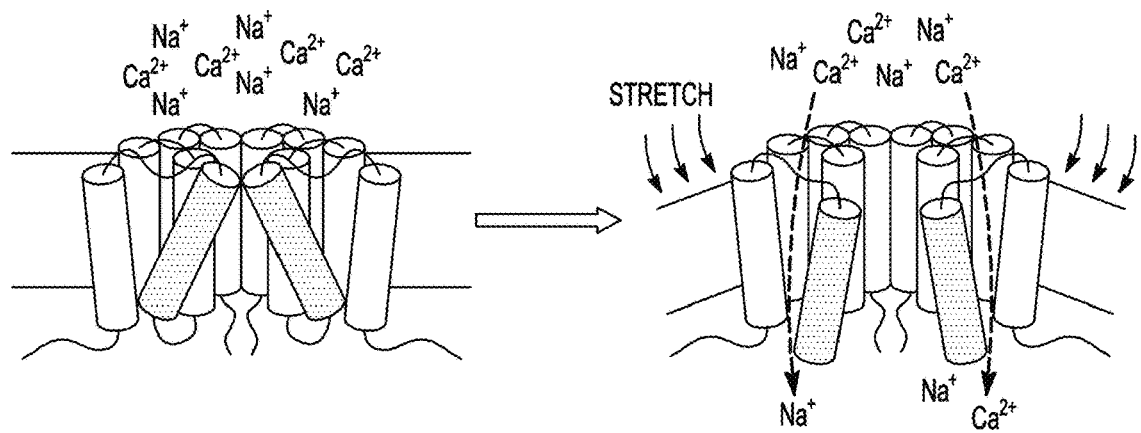
Figure 22B:
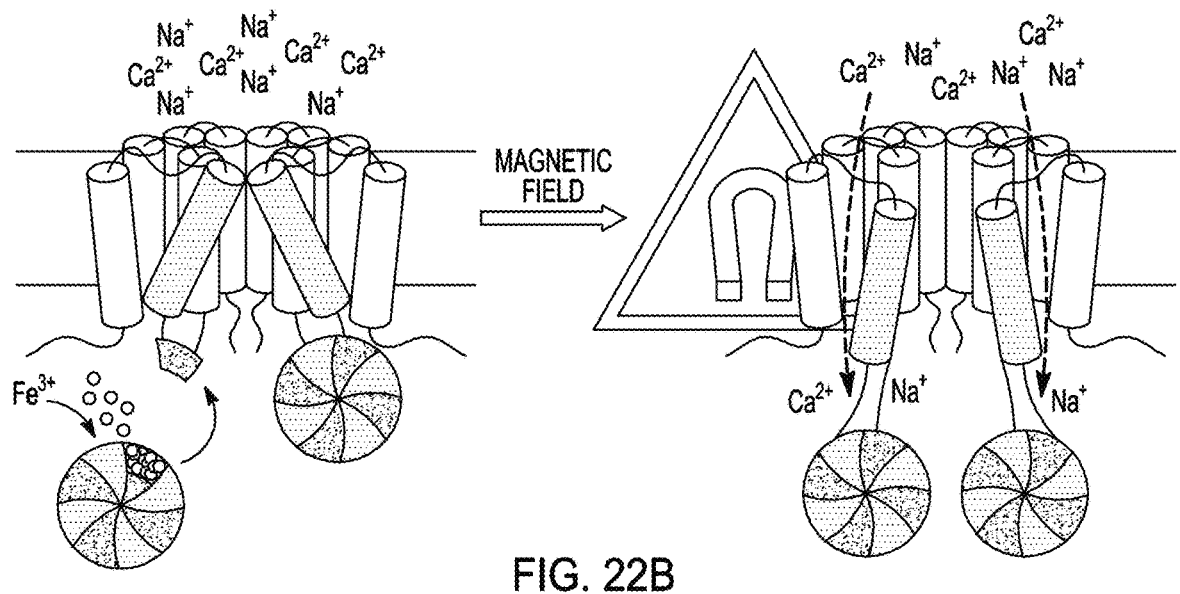

FIGS. 22A-B depicts a channel normally activated by stretch (top) is coupled to a paramagnetic domain which can be manipulated by a magnetic field (bottom). Design utilizes TRPV4 channel (two of four subunits shown in grey/blue) and ferritin, a globular iron storing protein (orange sphere). A heavy- and light chain fusion unit of ferritin will be introduced to the ion channel at locations previously found to be critical for gating. In conjunction with endogenous ferritin subunits, this mechanically-gated channel will become magnetically gated.

Figure 23:
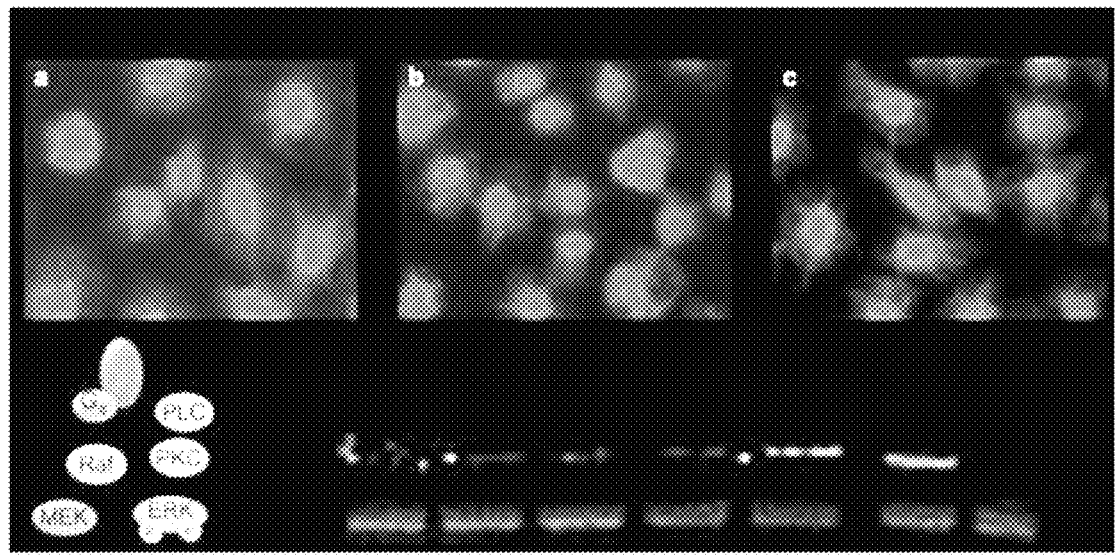

FIG. 23 Immunocytochemistry for FLAG-tag in Chinese hamster ovarian (CHO) cells stably expressing a. $G_q$-coupled Quicksilver b. $G_s$-coupled Storm c. $G_i$-coupled Iceman. d. Schematic depicting $G_q$-coupled signaling cascade and phosphorylation of ERK. e. Immunoblot for phosphorylated ERK (p-ERK) and ERK in cells expressing $G_q$-coupled Quicksilver exposed to 10 minutes of varying magnetic field strengths (millitesla; mT) for 10 minutes. Positive control, cells treated with AT1R ligand angiotensin II for 10 minutes. Negative control, untrasfected cells subjected to the magnet.

DETAILED DESCRIPTION

Abbreviations and Acronyms
AAV—adeno-associated virus
CIB—calcium imaging buffer
CICR—calcium-induced calcium release
cmcl2—cardiac myosin light chain 2
CMV—cytomegalovirus
CPP—conditioned place preference
D1R—dopamine receptor 1
DIO—double-floxed inverse open reading frame
DPT—days post transfection
GFP—green fluorescent protein
HEK—human embryonic kidney IRES—internal ribosomal entry site
ITR—inverted terminal repeat
pA—polyadenylation
RR—Ruthenium Red
RTPP—real time place preference
TRPV4—transient receptor potential vanilloid 4
TS—traffic signaling
WPRE—3' woodchuck hepatitis virus posttranscriptional response element
WT—wild type Definitions In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The terms "additional therapeutically active compound" or "additional therapeutic agent," as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As use herein, the terms "administration of" and or "administering" a compound should be understood to mean providing a compound of the invention or a prodrug of a compound of the invention to a subject in need of treatment.

The term "adult" as used herein, is meant to refer to any non-embryonic or non-juvenile subject. For example the term "adult adipose tissue stem cell," refers to an adipose stem cell, other than that obtained from an embryo or juvenile subject.

Cells or tissue are "affected" by an injury, disease or disorder if the cells or tissue have an altered phenotype relative to the same cells or tissue in a subject not afflicted with the injury, disease, condition, or disorder.

As used herein, an "agonist" is a composition of matter that, when administered to a mammal such as a human, enhances or extends a biological activity of interest. Such effect may be direct or indirect.

A disease, condition, or disorder is "alleviated" if the severity of a symptom of the disease or disorder, the frequency with which such a symptom is experienced by a patient, or both, are reduced.

As used herein, "alleviating an injury, disease or disorder symptom," means reducing the frequency or severity of the symptom.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The term "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

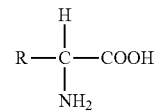

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

An "antagonist" is a composition of matter that when administered to a mammal such as a human, inhibits or impedes a biological activity attributable to the level or presence of an endogenous compound in the mammal. Such effect may be direct or indirect.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

An "antibody heavy chain," as used herein, refers to the larger of the two types of polypeptide chains present in all antibody molecules.

An "antibody light chain," as used herein, refers to the smaller of the two types of polypeptide chains present in all antibody molecules.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates.

A ligand or a receptor (e.g., an antibody) "specifically binds to" or "is specifically immunoreactive with" a compound when the ligand or receptor functions in a binding reaction which is determinative of the presence of the compound in a sample of heterogeneous compounds. Thus, under designated assay (e.g., immunoassay) conditions, the ligand or receptor binds preferentially to a particular compound and does not bind in a significant amount to other compounds present in the sample. For example, a polynucleotide specifically binds under hybridization conditions to a compound polynucleotide comprising a complementary sequence; an antibody specifically binds under immunoassay conditions to an antigen bearing an epitope against which the antibody was raised. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988, Antibodies, A Laboratory Manual, Cold Spring Harbor Publications, New York) for a description of immunoassay formats and conditions that can be used to determine specific immunoreactivity.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the invention include, but are not limited to, phosphorothioate oligonucleotides and other modifications of oligonucleotides.

The term "associated with ischemia" as used herein means that an injury, disease, or disorder that is being treated or which is being prevented either develops as a result of ischemia or ischemia develops as a result of the injury disease or disorder, i.e., the two are closely linked.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

"Binding partner," as used herein, refers to a molecule capable of binding to another molecule.

The term "biocompatible", as used herein, refers to a material that does not elicit a substantial detrimental response in the host.

As used herein, the term "biologically active fragments" or "bioactive fragment" of the polypeptides encompasses natural or synthetic portions of the full-length protein that are capable of specific binding to their natural ligand or of performing the function of the protein.

The term "biological sample," as used herein, refers to samples obtained from a living organism, including skin, hair, tissue, blood, plasma, cells, sweat, and urine.

As used herein, the term "biologically active fragments" or "bioactive fragment" of the polypeptides encompasses natural or synthetic portions of the full-length protein that are capable of specific binding to their natural ligand or of performing the function of the protein.

A "biomarker" is a specific biochemical in the body which has a particular molecular feature that makes it useful for measuring the progress of disease or the effects of treatment, or for measuring a process of interest.

As used herein, the term "carrier molecule" refers to any molecule that is chemically conjugated to the antigen of interest that enables an immune response resulting in antibodies specific to the native antigen.

As used herein "channel component" or "channel protein" refers to a channel that can be open to both environments at the same time (extracellular and intracellular), allowing the solutes it transports to diffuse without interruption. When a channel is opened, millions of ions can pass through the membrane per second. Channels include, but are not limited to, α-helical protein channels such as voltage-gated ion channel (VIC), ligand-gated ion channels (LGICs), electrochemical potential-driven transporters (porters (uniporters, symporters, antiporters) including glucose transporter, monoamine transporters (including: dopamine transporter (DAT), norepinephrine transporter (NET), serotonin transporter (SERT), vesicular monoamine transporters (VMAT)), Adenine nucleotide translocator (ANT), Nonribosomally synthesized porters, such as the nigericin (Nigericin) Family and the ionomycin (Ionomycin) Family and Ion-gradient-driven energizers. Channels also include, primary active transporters including P—P-bond-hydrolysis-driven transporters such as ATP-binding cassette transporter (ABC transporter; such as MDR, CFTR), V-type ATPase ("V" related to vacuolar); P-type ATPase; ("P" related to phosphorylation), such as : Na+/K+-ATPase, Plasma membrane Ca2+ ATPase; and Proton pump' F-type ATPase; ("F" related to factor), including: mitochondrial ATP synthase, chloroplast ATP synthasel; Decarboxylation-driven transporters; Methyltransfer-driven transporters; Oxidoreduction-driven transporters; and Light absorption-driven transporters, such as rhodopsin. This also includes ion channels, such as voltage gated ion channels and ligand gated ion channels, as well as calcium activated potassium channels and two pore domain potassium channel (TWIK, TREK, TASK, THIK, TALK).

As used herein, the term "chemically conjugated," or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates or carboxylic acids, on the antigen and the carrier molecule. Chemical conjugation also includes non-covalent linkage between the antigen and the carrier molecule.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

The term "competitive sequence" refers to a peptide or a modification, fragment, derivative, or homolog thereof that competes with another peptide for its cognate binding site.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. As used herein, the terms "complementary" or "complementarity" are used in reference to polynucleotides (i.e., a sequence of nucleotides) related by the base-pairing rules. For example, for the sequence "A-G-T," is complementary to the sequence "T-C-A."

Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "complex", as used herein in reference to proteins, refers to binding or interaction of two or more proteins. Complex formation or interaction can include such things as binding, changes in tertiary structure, and modification of one protein by another, such as phosphorylation.

A "compound," as used herein, refers to any type of substance or agent that is commonly considered a drug, or a candidate for use as a drug, as well as combinations and mixtures of the above.

As used herein, the term "conservative amino acid substitution" is defined herein as an amino acid exchange within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys V. Large, aromatic residues:
Phe, Tyr, Trp A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined or treated.

"Cytokine," as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, chemokines, protein or peptide hormones, and transforming growth factors. A number of other cytokines are known to those of skill in the art. The sources, characteristics, targets and effector activities of these cytokines have been described.

The term "delivery vehicle" refers to any kind of device or material which can be used to deliver compounds in vivo or can be added to a composition comprising compounds administered to a plant or animal. This includes, but is not limited to, implantable devices, aggregates of cells, matrix materials, gels, nucleic acids, etc.

As used herein, a "derivative" of a compound, when referring to a chemical compound, is one that may be produced from another compound of similar structure in one or more steps, as in replacement of H by an alkyl, acyl, or amino group.

A "derivative protein or peptide," as used herein, includes any protein or peptide, which in its entirety, or in part, comprises a substantially similar amino acid sequence to fusion peptide of the invention.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

As used herein, the term "diagnosis" refers to detecting a disease or disorder or a risk or propensity for development of a disease or disorder, for the types of diseases or disorders encompassed by the invention. In any method of diagnosis there exist false positives and false negatives. Any one method of diagnosis does not provide 100% accuracy.

A "disease" is a state of health of an animal wherein the subject cannot maintain homeostasis, and wherein if the disease is not ameliorated then the subject's health continues to deteriorate. In contrast, a "disorder" in an subject is a state of health in which the animal is able to maintain homeostasis, but in which the subject's state of health is less favorable than it would be in the absence of the disorder. Left untreated, a disorder does not necessarily cause a further decrease in the subject's state of health.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains. As used herein, the term "effector domain" refers to a domain capable of directly interacting with an effector molecule, chemical, or structure in the cytoplasm which is capable of regulating a biochemical pathway.

The term "downstream" when used in reference to a direction along a nucleotide sequence means the 5' to 3' direction. Similarly, the term "upstream" means the 3' to 5' direction.

As used herein, an "effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

An "enhancer" is a DNA regulatory element that can increase the efficiency of transcription, regardless of the distance or orientation of the enhancer relative to the start site of transcription.

As used herein, an "essentially pure" preparation of a particular protein or peptide is a preparation wherein at least about 95%, and including at least about 99%, by weight, of the protein or peptide in the preparation is the particular protein or peptide.

As used in the specification and the appended claims, the terms "for example," "for instance," "such as," "including" and the like are meant to introduce examples that further clarify more general subject matter. Unless otherwise specified, these examples are provided only as an aid for understanding the invention, and are not meant to be limiting in any fashion.

The terms "formula" and "structure" are used interchangeably herein.

As used herein the term "expression" when used in reference to a gene or protein, without further modification, is intended to encompass transcription of a gene and/or translation of the transcript into a protein.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, the term "fragment," as applied to a protein or peptide, can ordinarily be at least about 2-15 amino acids in length, at least about 15-25 amino acids, at least about 25-50 amino acids in length, at least about 50-75 amino acids in length, at least about 75-100 amino acids in length, and greater than 100 amino acids in length, depending on the particular protein or peptide being referred to.

As used herein, the term "fragment" as applied to a nucleic acid, may ordinarily be at least about 20 nucleotides in length, typically, at least about 50 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 350, even more preferably, at least about 350 nucleotides to about 500 nucleotides, yet even more preferably, at least about 500 to about 600, even more preferably, at least about 600 nucleotides to about 620 nucleotides, yet even more preferably, at least about 620 to about 650, and most preferably, the nucleic acid fragment will be greater than about 650 nucleotides in length.

As used herein, a "functional" molecule is a molecule in a form in which it exhibits a property or activity by which it is characterized. A functional enzyme, for example, is one that exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

As used herein, the term "induction of apoptosis" means a process by which a cell is affected in such a way that it begins the process of programmed cell death, which is characterized by the fragmentation of the cell into membrane-bound particles that are subsequently eliminated by the process of phagocytosis.

The term "inhibit," as used herein, refers to the ability of a compound, agent, or method to reduce or impede a described function, level, activity, rate, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block."

The term "inhibit a protein," as used herein, refers to any method or technique which inhibits protein synthesis, levels, activity, or function, as well as methods of inhibiting the induction or stimulation of synthesis, levels, activity, or function of the protein of interest. The term also refers to any metabolic or regulatory pathway which can regulate the synthesis, levels, activity, or function of the protein of interest. The term includes binding with other molecules and complex formation. Therefore, the term "protein inhibitor" refers to any agent or compound, the application of which results in the inhibition of protein function or protein pathway function. However, the term does not imply that each and every one of these functions must be inhibited at the same time.

As used herein "injecting or applying" includes administration of a compound of the invention by any number of routes and means including, but not limited to, topical, oral, buccal, intravenous, intramuscular, intra-arterial, intramedullary, intrathecal, intraventricular, transdermal, subcutaneous, intraperitoneal, intranasal, enteral, topical, sublingual, vaginal, ophthalmic, pulmonary, or rectal means.

The term "injected once with a 5-daily dose", as used herein, means that an induction therapy was initiated wherein mice were injected with 1 µg protein once a day for five consecutive days and then followed over time as indicated.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

The term "ischemia" as used herein refers to a local anemia due to mechanical obstruction of the blood supply, which gives rise to inadequate circulation of the blood to an organ, tissue, or region of an organ or tissue.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

A "ligand" is a compound that specifically binds to a target receptor.

A "receptor" is a compound that specifically binds to a ligand.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions.

"Malexpression" of a gene means expression of a gene in a cell of a patient afflicted with a disease or disorder, wherein the level of expression (including non-expression), the portion of the gene expressed, or the timing of the expression of the gene with regard to the cell cycle, differs from expression of the same gene in a cell of a patient not afflicted with the disease or disorder. It is understood that malexpression may cause or contribute to the disease or disorder, be a symptom of the disease or disorder, or both.

The term "material" refers to any compound, molecule, substance, or group or combination thereof that forms any type of structure or group of structures during or after electro-processing. Materials include natural materials, synthetic materials, or combinations thereof. Naturally occurring organic materials include any substances naturally found in the body of plants or other organisms, regardless of whether those materials have or can be produced or altered synthetically. Synthetic materials include any materials prepared through any method of artificial synthesis, processing, or manufacture. Preferably, the materials are biologically compatible materials.

The term "measuring the level of expression" or "determining the level of expression" as used herein refers to any measure or assay which can be used to correlate the results of the assay with the level of expression of a gene or protein of interest. Such assays include measuring the level of mRNA, protein levels, etc., and can be performed by assays such as northern and western blot analyses, binding assays, immunoblots, etc. The level of expression can include rates of expression and can be measured in terms of the actual amount of an mRNA or protein present. Such assays are coupled with processes or systems to store and process information and to help quantify levels, signals, etc. and to digitize the information for use in comparing levels.

The term "modulate", as used herein, refers to changing the level of an activity, function, or process. The term "modulate" encompasses both inhibiting and stimulating an activity, function, or process.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "nucleic acid construct," as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "Oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"Operably linked" refers to a juxtaposition wherein the components are configured so as to perform their usual function. Thus, control sequences or promoters operably linked to a coding sequence are capable of effecting the expression of the coding sequence. By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "peptide" typically refers to short polypeptides.

The term "per application" as used herein refers to administration of a compositions, drug, or compound to a subject.

"Permeation enhancement" and "permeation enhancers" as used herein relate to the process and added materials which bring about an increase in the permeability of skin to a poorly skin permeating pharmacologically active agent, i.e., so as to increase the rate at which the drug permeates through the skin and enters the bloodstream. "Permeation enhancer" is used interchangeably with "penetration enhancer".

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan. As used herein, "pharmaceutical compositions" include formulations for human and veterinary use.

As used herein, the term "pharmaceutically-acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Plurality" means at least two.

A "polynucleotide" means a single strand or parallel and anti-parallel strands of a nucleic acid. Thus, a polynucleotide may be either a single-stranded or a double-stranded nucleic acid.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" means a non-naturally occurring peptide or polypeptide. Synthetic peptides or polypeptides can be synthesized, for example, using an automated polypeptide synthesizer. Various solid phase peptide synthesis methods are known to those of skill in the art.

By "presensitization" is meant pre-administration of at least one innate immune system stimulator prior to challenge with a pathogenic agent. This is sometimes referred to as induction of tolerance.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

The term "prevent," as used herein, means to stop something from happening, or taking advance measures against something possible or probable from happening. In the context of medicine, "prevention" generally refers to action taken to decrease the chance of getting a disease or condition.

A "prophylactic" treatment is a treatment administered to a subject who does not exhibit signs of a disease or injury or exhibits only early signs of the disease or injury for the purpose of decreasing the risk of developing pathology associated with the disease or injury.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure. In particular, purified sperm cell DNA refers to DNA that does not produce significant detectable levels of non-sperm cell DNA upon PCR amplification of the purified sperm cell DNA and subsequent analysis of that amplified DNA. A "significant detectable level" is an amount of contaminate that would be visible in the presented data and would need to be addressed/explained during analysis of the forensic evidence.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates. The terms "protein pathway" and "protein regulatory pathway" are used interchangeably herein.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

The term "regulate" refers to either stimulating or inhibiting a function or activity of interest.

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

As used herein, the term "secondary antibody" refers to an antibody that binds to the constant region of another antibody (the primary antibody).

By the term "signal sequence" is meant a polynucleotide sequence which encodes a peptide that directs the path a polypeptide takes within a cell, i.e., it directs the cellular processing of a polypeptide in a cell, including, but not limited to, eventual secretion of a polypeptide from a cell. A signal sequence is a sequence of amino acids which are typically, but not exclusively, found at the amino terminus of a polypeptide which targets the synthesis of the polypeptide to the endoplasmic reticulum. In some instances, the signal peptide is proteolytically removed from the polypeptide and is thus absent from the mature protein.

By "small interfering RNAs (siRNAs)" is meant, inter alia, an isolated dsRNA molecule comprised of both a sense and an anti-sense strand. In one aspect, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

As used herein, the term "solid support" relates to a solvent insoluble substrate that is capable of forming linkages (preferably covalent bonds) with various compounds. The support can be either biological in nature, such as, without limitation, a cell or bacteriophage particle, or synthetic, such as, without limitation, an acrylamide derivative, agarose, cellulose, nylon, silica, or magnetized particles.

By the term "specifically binds to", as used herein, is meant when a compound or ligand functions in a binding reaction or assay conditions which is determinative of the presence of the compound in a sample of heterogeneous compounds.

The term "standard," as used herein, refers to something used for comparison. For example, a standard can be a known standard agent or compound which is administered or added to a control sample and used for comparing results when measuring said compound in a test sample. In one aspect, the standard compound is added or prepared at an amount or concentration that is equivalent to a normal value for that compound in a normal subject. Standard can also refer to an "internal standard," such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "subject" of analysis, diagnosis, or treatment is an animal. Such animals include mammals, preferably a human.

As used herein, a "subject in need thereof" is a patient, animal, mammal, or human, who will benefit from the method of this invention.

As used herein, a "substantially homologous amino acid sequence" includes those amino acid sequences which have at least about 95% homology, preferably at least about 96% homology, more preferably at least about 97% homology, even more preferably at least about 98% homology, and most preferably at least about 99% homology to an amino acid sequence of a reference sequence. Amino acid sequences similarity or identity can be computed using, for example, the BLASTP and TBLASTN programs which employ the BLAST (basic local alignment search tool) algorithm. The default setting used for these programs are suitable for identifying substantially similar amino acid sequences for purposes of the present invention.

"Substantially homologous nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. Preferably, the substantially similar nucleic acid sequence encodes the peptide encoded by the reference nucleic acid sequence. The percentage of identity between the substantially similar nucleic acid sequence and the reference nucleic acid sequence is at least about 50%, 65%, 75%, 85%, 95%, 96%, 97%, 98%, 99% or more. Substantial similarity of nucleic acid sequences can be determined by comparing the sequence identity of two sequences, for example by physical/chemical methods (i.e., hybridization) or by sequence alignment via computer algorithm. Suitable nucleic acid hybridization conditions to determine if a nucleotide sequence is substantially similar to a reference nucleotide sequence are: 7% sodium dodecyl sulfate SDS, 0.5 M $NaPO_4$, 1 mM EDTA at 50° C. with washing in 2× standard saline citrate (SSC), 0.1% SDS at 50° C.; preferably in 7% (SDS), 0.5 M $NaPO_4$, 1 mM EDTA at 50° C. with washing in 1×SSC, 0.1% SDS at 50° C.; preferably 7% SDS, 0.5 M $NaPO_4$, 1 mM EDTA at 50° C. with washing in 0.5×SSC, 0.1% SDS at 50° C.; and more preferably in 7% SDS, 0.5 M $NaPO_4$, 1 mM EDTA at 50° C. with washing in 0.1×SSC, 0.1% SDS at 65° C. Suitable computer algorithms to determine substantial similarity between two nucleic acid sequences include, GCS program package (Devereux et al., 1984 Nucl. Acids Res. 12:387), and the BLASTN or FASTA programs (Altschul et al., 1990 Proc. Natl. Acad. Sci. USA. 1990 87:14:5509-13; Altschul et al., J. Mol. Biol. 1990 215:3:403-10; Altschul et al., 1997 Nucleic Acids Res. 25:3389-3402). The default settings provided with these programs are suitable for determining substantial similarity of nucleic acid sequences for purposes of the present invention.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

"Tissue" means (1) a group of similar cells united to perform a specific function; (2) a part of an organism consisting of an aggregate of cells having a similar structure and function; or (3) a grouping of cells that are similarly characterized by their structure and function, such as muscle or nerve tissue.

The term "transfection" is used interchangeably with the terms "gene transfer", "transformation," and "transduction", and means the intracellular introduction of a polynucleotide. "Transfection efficiency" refers to the relative amount of the transgene taken up by the cells subjected to transfection. In practice, transfection efficiency is estimated by the amount of the reporter gene product expressed following the transfection procedure.

The term "transgene" is used interchangeably with "inserted gene," or "expressed gene" and, where appropriate, "gene". "Transgene" refers to a polynucleotide that, when introduced into a cell, is capable of being transcribed under appropriate conditions so as to confer a beneficial property to the cell such as, for example, expression of a therapeutically useful protein. It is an exogenous nucleic acid sequence comprising a nucleic acid which encodes a promoter/regulatory sequence operably linked to nucleic acid which encodes an amino acid sequence, which exogenous nucleic acid is encoded by a transgenic mammal.

As used herein, a "transgenic cell" is any cell that comprises a nucleic acid sequence that has been introduced into the cell in a manner that allows expression of a gene encoded by the introduced nucleic acid sequence.

As used herein, the term "transgenic mammal" means a mammal, the germ cells of which comprise an exogenous nucleic acid.

The term to "treat," as used herein, means reducing the frequency with which symptoms are experienced by a patient or subject or administering an agent or compound to reduce the frequency with which symptoms are experienced.

As used herein, the term "treating" may include prophylaxis of the specific injury, disease, disorder, or condition, or alleviation of the symptoms associated with a specific injury, disease, disorder, or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease and should be interpreted based on the context of the use.

"Treating" is used interchangeably with "treatment" herein.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

Embodiments

In one aspect, a fusion protein construct of the invention or an expression vector of the invention can be administered by a route selected from, including, but not limited to, intravenously, intrathecally, locally (including in the tissue of interest, such as muscle or brain), intramuscularly, topically, orally, intra-arterially, parenterally, etc. Administration can be more than once. Based on the teachings herein, one of ordinary skill in the art can determine how often to administer the compound, the dose to be used, and what combination of other agents it can be administered with such as therapeutic agents and/or other drugs or compounds such as antimicrobial agents, anti-inflammatory agents, etc. Also, one of ordinary skill in the art can also determine if all compounds should be administered simultaneously or not.

Numerical ranges recited herein by endpoints include all numbers and fractions subsumed within that range (e.g., 1 to 5 includes 1, 1.5, 2, 2.75, 3, 3.90, 4, and 5). It is also to be understood that all numbers and fractions thereof are presumed to be modified by the term "about."

In one embodiment, a unit dose of fusion protein construct or proteins can be administered. Other therapeutic agents of the invention can also be administered as unit doses. Kits can be provided with unit doses in a container or syringe or amounts that one of ordinary skill in the art can administer based on a dose per weight, etc.

The invention further includes isolated nucleic acids comprising sequences encoding proteins or peptides of the invention. The present invention further includes a fusion protein wherein the order of the peptides is reversed.

Over the past decade, AAV vectors have emerged as a promising gene delivery system for human gene therapy. Recombinant AAV vectors transduce a wide variety of tissues in vivo and provide for long-term gene expression without provoking significant immune responses. To date, over 100 AAV serotypes have been reported. The natural tissue tropism of the various AAV serotypes can be exploited to favor gene delivery to one organ over another. This tropism is based on the viral capsids recognizing specific viral receptors expressed on specific cell types, thus allowing a degree of cell specific targeting within a given organ. Cell-specific expression may be further aided by the use of tissue-specific promoters conferring gene expression restricted to a specific cell type. This is desirable for gene therapy applications targeting organ specific diseases, as this will help avoid any possible harmful side effects due to gene expression in off target organs.

One of ordinary skill in the art will appreciate that depending on factors such as the age, sex, health, of the subject or the particular injury or disease being prevented or treated that the recombinant AAV vector can be administered in varying quantities, at different times, and various means. In one aspect, a recombinant AAV vector of the invention can be administered systemically, intravenously, by intracoronary infusion, locally, topically, or by direct injection. The method comprises administering to a subject a pharmaceutical composition comprising an effective amount of a recombinant adeno-associated viral (AAV) vector comprising a regulatory element. The regulatory element comprises at least one promoter element and optionally at least one enhancer element. An enhancer and promoter are operably linked. The recombinant AAV vector also may optionally comprise at least one gene operably linked to a promoter element. The AAV may comprise the entire AAV genome, or a homolog or fragment thereof, such as the capsid of the particular AAV. However, it should be noted that the entire AAV genome may not be useful in some situations because of a need to make the vector replication-deficient and/or to insert genes of interest such as therapeutic genes.

The regulatory elements and the gene of interest may also be substituted with active fragments, modifications, or homologs thereof.

In one embodiment, a subject is pretreated with an effective amount of neuraminidase or other desialylation agent to increase desialylation of cell surface N-linked glycans. In one aspect, the pretreatment enhances AAV binding to its cognate receptor. In one aspect, the neuraminidase or other desialylation agent is applied systemically or locally.

The present invention further provides a kit for administering a pharmaceutical composition comprising an AAV vector of the invention or for using an AAV vector of the invention, and an instructional material for the use thereof.

Also included are peptides and polypeptides that have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring or non-standard synthetic amino acids. The peptides of the invention are not limited to products of any of the specific exemplary processes listed herein.

The invention includes the use of beta-alanine (also referred to as β-alanine, β-Ala, bA, and βA), having the structure:

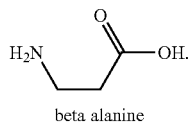

beta alanine

The peptides of the present invention may be readily prepared by standard, well-established techniques, such as solid-phase peptide synthesis (SPPS) as described by Stewart et al. in Solid Phase Peptide Synthesis, 2nd Edition, 1984, Pierce Chemical Company, Rockford, Ill.; and as described by Bodanszky and Bodanszky in The Practice of Peptide Synthesis, 1984, Springer-Verlag, N.Y. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method which utilized tert-butyloxycarbonyl as the α-amino protecting group, and the FMOC method which utilizes 9-fluorenylmethyloxcarbonyl to protect the α-amino of the amino acid residues, both methods of which are well known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl-blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high-resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide is purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as C4-, C8- or C18-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

It will be appreciated, of course, that the peptides or antibodies, derivatives, or fragments thereof may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Amino Acid Substitutions

In certain embodiments, the disclosed methods and compositions may involve preparing peptides with one or more substituted amino acid residues.

In various embodiments, the structural, physical and/or therapeutic characteristics of peptide sequences may be optimized by replacing one or more amino acid residues.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

The skilled artisan will be aware that, in general, amino acid substitutions in a peptide typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, one can make the following isosteric and/or conservative amino acid changes in the parent polypeptide sequence with the expectation that the resulting polypeptides would have a similar or improved profile of the properties described above:

Substitution of alkyl-substituted hydrophobic amino acids: including alanine, leucine, isoleucine, valine, norleucine, S-2-aminobutyric acid, S-cyclohexylalanine or other simple alpha-amino acids substituted by an aliphatic side chain from C1-10 carbons including branched, cyclic and straight chain alkyl, alkenyl or alkynyl substitutions.

Substitution of aromatic-substituted hydrophobic amino acids: including phenylalanine, tryptophan, tyrosine, biphenylalanine, 1-naphthylalanine, 2-naphthylalanine, 2-benzothienylalanine, 3-benzothienylalanine, histidine, amino, alkylamino, dialkylamino, aza, halogenated (fluoro, chloro, bromo, or iodo) or alkoxy-substituted forms of the previous listed aromatic amino acids, illustrative examples of which are: 2-,3- or 4-aminophenylalanine, 2-,3- or 4-chlorophenylalanine, 2-,3- or 4-methylphenylalanine, 2-,3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2,3, or 4-biphenylalanine, 2',-3',- or 4'-methyl-2, 3 or 4-biphenylalanine, and 2- or 3-pyridylalanine.

Substitution of amino acids containing basic functions: including arginine, lysine, histidine, ornithine, 2,3-diaminopropionic acid, homoarginine, alkyl, alkenyl, or aryl-substituted (from $C_1$-$C_{10}$ branched, linear, or cyclic) derivatives of the previous amino acids, whether the sub stituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha methyl arginine, alpha methyl 2,3-diaminopropionic acid, alpha methyl histidine, alpha methyl ornithine where alkyl group occupies the pro-R position of the alpha carbon. Also included are the amides formed from alkyl, aromatic, heteroaromatic (where the heteroaromatic group has one or more nitrogens, oxygens, or sulfur atoms singly or in combination) carboxylic acids or any of the many well-known activated derivatives such as acid chlorides, active esters, active azolides and related derivatives) and lysine, ornithine, or 2,3-diaminopropionic acid.

Substitution of acidic amino acids: including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids.

Substitution of side chain amide residues: including asparagine, glutamine, and alkyl or aromatic substituted derivatives of asparagine or glutamine.

Substitution of hydroxyl containing amino acids: including serine, threonine, homoserine, 2,3-diaminopropionic acid, and alkyl or aromatic substituted derivatives of serine or threonine. It is also understood that the amino acids within each of the categories listed above can be substituted for another of the same group.

For example, the hydropathic index of amino acids may be considered (Kyte & Doolittle, 1982, J. Mol. Biol., 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within +/−2 is preferred, within +/−1 are more preferred, and within +/−0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL Rockefeller University website). For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded peptide sequence are well known and a matter of routine experimentation for the skilled artisan, for example by the technique of site-directed mutagenesis or by synthesis and assembly of oligonucleotides encoding an amino acid substitution and splicing into an expression vector construct.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

The present invention also provides for analogs of proteins. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. To that end, 10 or more conservative amino acid changes typically have no effect on peptide function.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides or antibody fragments which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, Guide to Protein Purification, Harcourt Brace Jovanovich, San Diego).

In another embodiment disclosed herein, peptide longevity is enhanced by the addition of adducts such as sucrose or polyethylene glycol, production of peptide-IgG chimeras, or the peptides can be cyclized via cysteine-cysteine linkages, which is a modification known to enhance the biological activities of a variety of peptides.

In one aspect a polyethylene glycol adduct is (2-aminoethyl)-O'—(N-diglycolyl-2-aminoethyl)-hexaethyleneglycol. In another aspect of the invention, a polyethylene glycol adduct is in the form of GK[(2-aminoethyl)-O'—(N-diglycolyl-2-aminoethyl)-hexaethyleneglycol]GG. The dipeptide GK increases peptide solubility. The dipeptide GG is present as a spacer between the solid support and peptide chain to improve the ease of peptide synthesis.

The present disclosure also contemplates any of the peptides derivatized with functional groups and/or linked to other molecules to facilitate their delivery to specific sites of action, to potentiate their activity, or complexed covalently or non-covalently to other pharmaceuticals, bioactive agents, or other molecules. Such derivatizations must be accomplished so as to not significantly interfere with the properties of the peptides. Carriers and derivatizations must also be designed or chosen so as not to exert toxic or undesirable activities on animals or humans treated with these formulations. Functional groups which may be covalently linked to the peptides may include, but not be limited to, amines, alcohols, or ethers. Functional groups to be covalently linked to the peptides to increase their in vivo half-lives may include, but not be limited to, polyethylene glycols, small carbohydrates such as sucrose, or peptides and proteins. The peptides may also be synthesized by recombinant DNA techniques with expression vectors for use in biological systems, such as bacteria, yeast, insect, or mammalian cells.

Generally, the amount of peptide administered depends upon the degree of immune response that is desired. Those skilled in the art may derive appropriate dosages and schedules of administration to suit the specific circumstances and needs of the patient. Typically, dosages of peptide are between about 0.001 mg/kg and about 100 mg/kg body weight. In some embodiments dosages are between about 0.01 mg/kg and about 60 mg/kg body weight. In other embodiments, dosages are between about 0.05 mg/kg and about 5 mg/kg body weight.

In general, the schedule or timing of administration of a peptide of the invention is according to the accepted practice for the procedure being performed.

When used in vivo, the peptides of the invention are preferably administered as a pharmaceutical composition. The invention thus provides pharmaceutical compositions comprising a peptide, or a pharmaceutically acceptable salt thereof, and a pharmaceutically acceptable carrier. The peptide of the invention may be present in a pharmaceutical composition in an amount from 0.001 to 99.9 wt %, and more preferably from about 0.1 to 99.0 wt %. To achieve good plasma concentrations, a peptide or a combination of peptides, may be administered, for example, by intravenous injection, as a solution comprising 0.1 to 1.0% of the active agent.

The compositions of the present invention may comprise at least one active peptide, one or more acceptable carriers, and optionally other peptides or therapeutic agents.

For in vivo applications, the peptides of the present invention may comprise a pharmaceutically acceptable salt. Suitable acids which are capable of forming such salts with the compounds of the present invention include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, anthranilic acid, cinnamic acid, naphthalene sulfonic acid, sulfanilic acid and the like.

Pharmaceutically acceptable carriers include physiologically tolerable or acceptable diluents, excipients, solvents or adjuvants. The compositions are preferably sterile and non-pyrogenic. Examples of suitable carriers include, but are not limited to, water, normal saline, dextrose, mannitol, lactose or other sugars, lecithin, albumin, sodium glutamate, cysteine hydrochloride, ethanol, polyols (propylene glycol, polyethylene glycol, glycerol, and the like), vegetable oils (such as olive oil), injectable organic esters such as ethyl oleate, ethoxylated isostearyl alcohols, polyoxyethylene sorbitol and sorbitan esters, microcrystalline cellulose, aluminum methahydroxide, bentonite, kaolin, agar-agar and tragacanth, or mixtures of these substances, and the like.

The pharmaceutical compositions may also contain minor amounts of nontoxic auxiliary pharmaceutical substances or excipients and/or additives, such as wetting agents, emulsifying agents, pH buffering agents, antibacterial and antifungal agents (such as parabens, chlorobutanol, phenol, sorbic acid, and the like). Suitable additives include, but are not limited to, physiologically biocompatible buffers (e.g., tromethamine hydrochloride), additions (e.g., 0.01 to 10 mole percent) of chelants (such as, for example, DTPA or DTPA-bisamide) or calcium chelate complexes (as for example calcium DTPA or CaNaDTPA-bisamide), or, optionally, additions (e.g. 1 to 50 mole percent) of calcium or sodium salts (for example, calcium chloride, calcium ascorbate, calcium gluconate or calcium lactate). If desired, absorption enhancing or delaying agents (such as liposomes, aluminum monostearate, or gelatin) may be used. The compositions can be prepared in conventional forms, either as liquid solutions or suspensions, solid forms suitable for solution or suspension in liquid prior to injection, or as emulsions. Pharmaceutical compositions according to the present invention can be prepared in a manner fully within the skill of the art.

The peptides of the invention, pharmaceutically acceptable salts thereof, or pharmaceutical compositions comprising these compounds may be administered so that the compounds may have a physiological effect. Administration may occur enterally or parenterally; for example orally, rectally, intracisternally, intravaginally, intraperitoneally, locally (e.g., with powders, ointments or drops), or as a buccal or nasal spray or aerosol. Parenteral administration is preferred. Particularly preferred parenteral administration methods include intravascular administration (e.g. intravenous bolus injection, intravenous infusion, intra-arterial bolus injection, intra-arterial infusion and catheter instillation into the vasculature), peri- and intra-target tissue injection (e.g. peri-tumoral and intra-tumoral injection), subcutaneous injection or deposition including subcutaneous infusion (such as by osmotic pumps), intramuscular injection, and direct application to the target area, for example by a catheter or other placement device.

Where the administration of the peptide is by injection or direct application, the injection or direct application may be in a single dose or in multiple doses. Where the administration of the compound is by infusion, the infusion may be a single sustained dose over a prolonged period of time or multiple infusions.

A composition of the invention may comprise additional ingredients. As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

The pharmaceutical composition may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the condition or disease being treated, the type and age of the animal, etc.

The invention also includes a kit comprising the composition of the invention and an instructional material which describes adventitially administering the composition to a cell or a tissue of a subject. In another embodiment, this kit comprises a (preferably sterile) solvent suitable for dissolving or suspending the composition of the invention prior to administering the compound to the subject.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of using the compositions for diagnostic or identification purposes or of alleviation the diseases or disorders in a cell or a tissue of a mammal. The instructional material of the kit of the invention may, for example, be affixed to a container which contains the multimeric peptide of the invention or be shipped together with a container which contains the peptide. Alternatively, the instructional material may be shipped separately from the container with the intention that the instructional material and the compound be used cooperatively by the recipient.

In other embodiments, therapeutic agents, including, but not limited to, cytotoxic agents, anti-angiogenic agents, pro-apoptotic agents, antibiotics, hormones, hormone antagonists, chemokines, drugs, prodrugs, toxins, enzymes or other agents may be used as adjunct therapies.

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double-stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, OLIGONUCLEOTIDE SYNTHESIS: A PRACTICAL APPROACH (IRL Press, Oxford, England)). RNAs may be produce in high yield via in vitro transcription using plasmids such as SP65 (Promega Corporation, Madison, Wis.).

The invention further provides a kit comprising one or more peptides or expression vectors of the invention, an applicator, an instructional material for the use thereof.

Other embodiments of the invention will be apparent to those skilled in the art based on the disclosure and embodiments of the invention described herein. It is intended that the specification and examples be considered as exemplary only, with a true scope and spirit of the invention being indicated by the following claims. While some representative experiments have been performed in test animals, similar results are expected in humans. The exact parameters to be used for injections in humans can be easily determined by a person skilled in the art.

The invention is now described with reference to the following Examples and Embodiments. Without further description, it is believed that one of ordinary skill in the art can, using the preceding description and the following illustrative examples, make and utilize the present invention and practice the claimed methods. The following working examples therefore, are provided for the purpose of illustration only and specifically point out the preferred embodiments of the present invention, and are not to be construed as limiting in any way the remainder of the disclosure. Therefore, the examples should be construed to encompass any and all variations which become evident as a result of the teaching provided herein.

Example 1

Provided is a novel single-component magnetogenetic actuator engineered by fusing the cation channel, transient receptor potential vanilloid 4 (TRPV4) (13-14; human mRNA Accession numbers: NM_001177428; NM_001177431; NM_001177433; NM_021625; NM_147204; human protein accession numbers: NP_001170899.1; NP_001170902.1; NP_001170904.1; NP_067638.3; and NP_671737.1; mouse accession numbers: NM_022017 and NP_071300.2; which sequences are herewith incorporated by reference) with the paramagnetic iron storage protein, ferritin (15; NM_000146; NM_002032 which sequences are herewith incorporated by reference). This actuator has been successfully applied to the nervous system and validated it using in vitro calcium imaging, brain slice electrophysiology, in vivo electrophysiology, and acute modulation of behavior in freely moving zebrafish and mice.

Figure 6A:
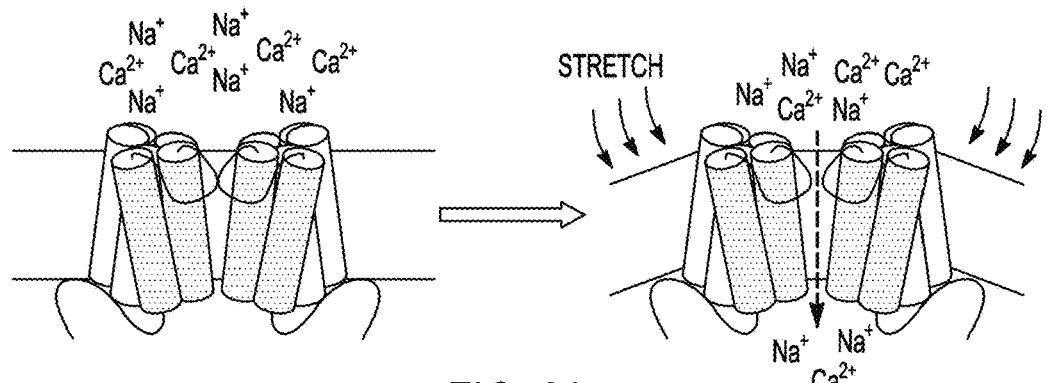
FIGS. 6A-B: Model of magnetic activation via Magneto. (a) The stretch-sensing cation channel, TRPV4, is gated by pressure to depolarize cells. For simplicity, only two of the four homomeric subunits are shown. (b) Coupling ferritin to the TRPV4 C-terminus converts TRPV4 to a magnetic field detector. Gating properties were extrapolated from published descriptions of TRPV1 and TRPA1 gating mechanisms (1-2; Supplementary References).
Figure 6B:
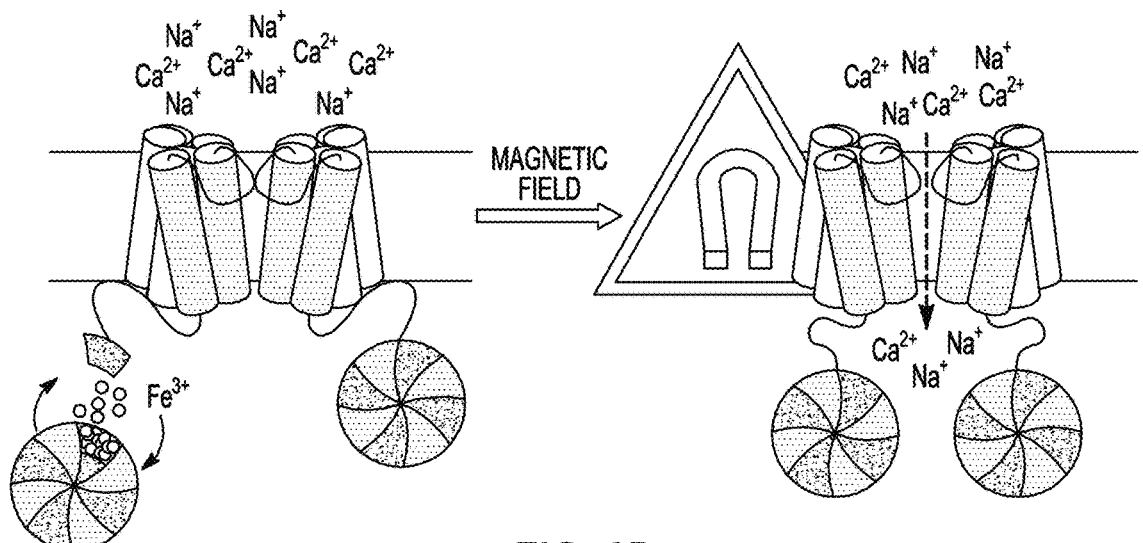
Figure 9A:
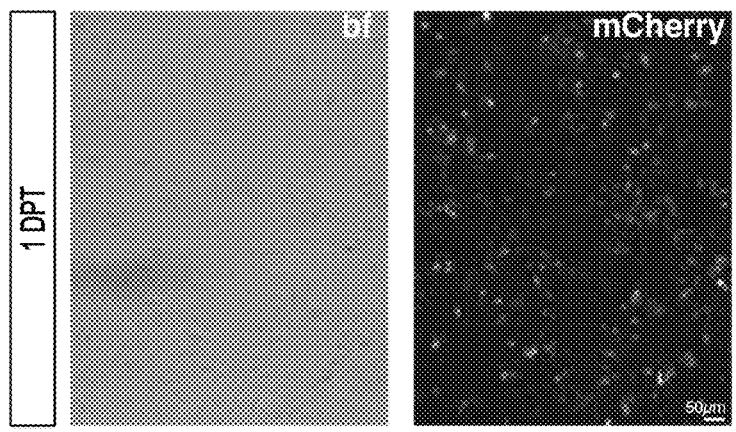
FIGS. 9A-D: Viability of Magneto2.0 transfected mammalian cells. (a-d) Viability of Magneto2.0 transfected HEK293 cells several days post transfection (DPT). Images show brightfield and mCherry fluorescence. Zoom increased in (c-d) due to cell division. images are representative of n>100 cells examined.
Figure 9B:
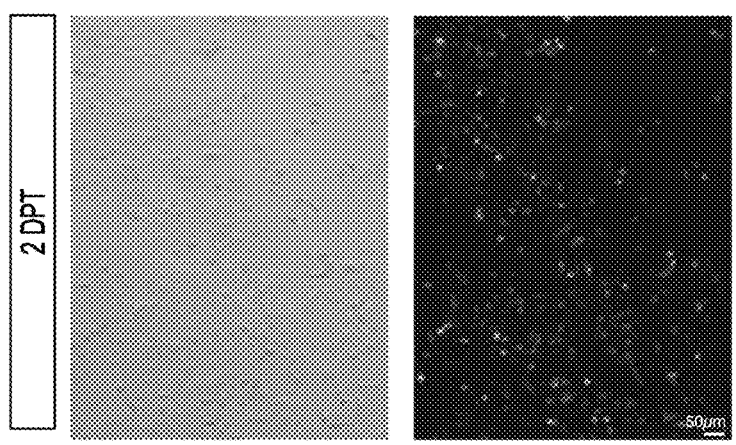
Figure 9C:
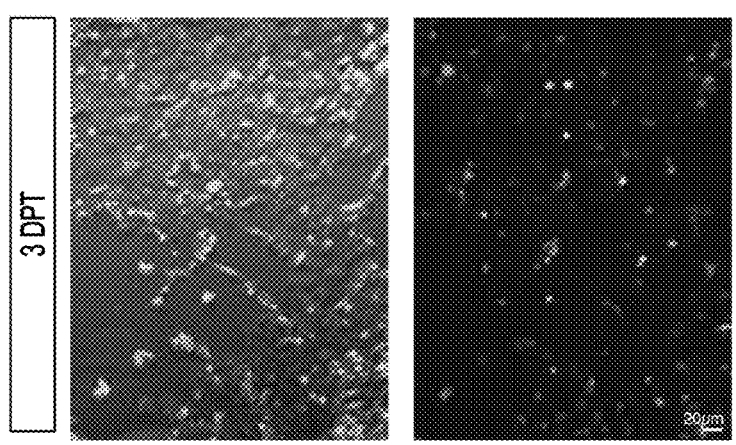
Figure 9D:
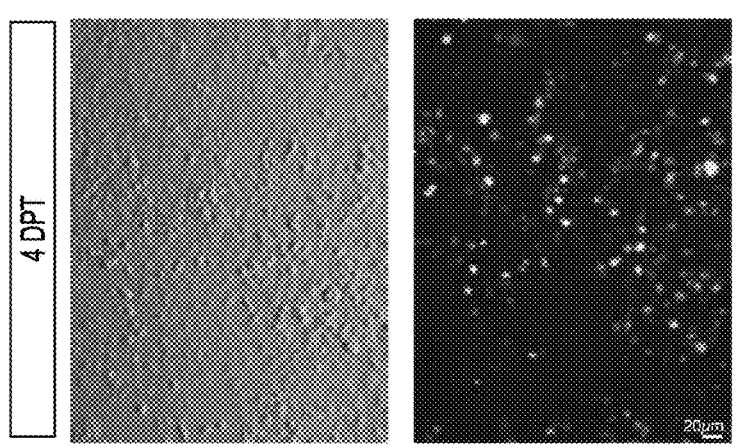

To design a novel magnetogenetic actuator, a library was developed of 21 proteins consisting of TRPV4 fused to a gene encoding two subunits of the paramagnetic ferritin protein (Table 1) (16). Human embryonic kidney (HEK) 293 cells did not express 18 of the 21 generated chimeric proteins following transient transfection, presumably due to cytotoxicity of the chimeric channels. For the three channels that did express in HEK293 cells, in vitro calcium imaging was performed to determine whether the fusion proteins responded to magnetic fields. Using the fluorescent calcium-binding dye Fluo-4, calcium transients were measured in response to a 40-50 mT magnetic field delivered by an electromagnet (FIG. 1). Of the three candidate proteins, detectable calcium transients in response to magnetic stimulation was observed with one fusion protein, consisting of ferritin tethered to a truncated TRPV4 carboxyl-terminus (Δ760-871) (FIGS. 6-7).

TABLE 1

Description of TRPV4-ferritin fusion proteins tested.

| Ferritin coupling location | Other features | Survival | Calcium imaging |
|---|---|---|---|
| C-terminus (Δ760-871) | N/A | Yes | Yes |
| N-terminus (Δ1-201) | N/A | Yes | No |
| C-terminus (full channel) | N/A | Yes | No |
| S4/5 loop: YFTRGLKLTG ... ferritin ... YSIMIQKILF | "Arg" linker 1X | No | |
| | "Gly" linker 1X | No | |
| | "Arg" linker 2X | No | |
| | "Gly" linker 2X | No | |
| | "Arg" linker 3X | No | |
| | "Gly" linker 3X | No | |
| | "Arg" linker 4X | No | |
| | "Gly" linker 4X | No | |
| | "Arg" linker 5X | No | |
| | "Gly" linker 5X | No | |
| | "Arg" linker 6X | No | |
| | "Gly" linker 6X | No | |
| | "Arg" linker 7X | No | |
| | "Gly" linker 7X | No | |
| | "Arg" linker 8X | No | |
| | "Gly" linker 8X | No | |
| | "Arg" linker 9X | No | |
| | "Gly" linker 9X | No | |

Arg linker: TRPV4-RRRLLSGCP ... ferritin ... RPRERRRRLRR-TRPV4
Gly linker: TRPV4-RRRLLSGCP ... ferritin .... RGGGGGSGGY-TRPV4

For insertions into the TRPV4 S4-S5 intracellular loop, the amino acid sequence of TRPV4 precedes and succeeds the intervening ferritin protein in the "ferritin coupling location" column. "Arg" and "Gly" are separate linkers used to expand the S4/S5 intracellular loop where ferritin was inserted and refer to the predominant amino acids expressed on the C-terminus of ferritin reconnecting to the S5 transmembrane domain of TRPV4. Specific amino acid sequences for the linkers used to expand the S4-S5 intracellular loop are shown at the bottom, which were sequentially inserted (e.g. 1×, 2×, 3×, etc.). The "Survival" column indicates whether cells survived following transfection as measured by expression of the mCherry gene under control of an IRES cassette. The "Calcium imaging" column refers to whether calcium transients were detectable following stimulation with magnetic fields.

Because the ~20% increase in magnetically evoked calcium transients were smaller than expected TRPV4 responses (FIG. 7h), it was hypothesized that cellular trafficking to the cell membrane was disrupted (14,17), resulting in blunted calcium signaling. To address this issue, the chimeric channel's plasma membrane localization was optimized using a strategy employed for optogenetic actuators (18-19). Ultimately, it was determined that the addition of a membrane trafficking signal enhanced the prototype channel's membrane expression (FIG. 8), and this improved channel was termed "Magneto2.0." Initially, it was confirmed that HEK293 cells were viable after Magneto2.0 transfection (FIG. 9). Next, magnetic field dependent calcium transients produced by Magneto2.0 were measured using the paradigm described in FIG. 7. It was observed that cells transfected with Magneto2.0 (58% mCherry+ cells, n=6 coverslips, n=539 cells) exhibited robust calcium transients approximately 3-fold higher than baseline after 50 mT magnetic stimulation with no change in any of the control conditions. Controls included: (1) cells expressing non-fused TRPV4 and ferritin moieties, (2) unstimulated Magneto2.0 expressing cells, (3) Magneto2.0 expressing cells exposed to the TRP pore blocker ruthenium red (RR), and (4) Magneto2.0 expressing cells in $Ca^{2+}$ free extracellular media (FIG. 1a-e, g). Universally, maximal calcium fluorescence was observed minutes after magnetic field application in magnetic field stimulated Magneto2.0 expressing cells. However, a small influx of calcium was also observed during magnetic field application in Magneto2.0 expressing cells (FIG. 1h) followed by the aforementioned delay in maximal calcium signaling, which was hypothesized as calcium-induced calcium release (CICR) caused by the initial influx of calcium observed during magnetic stimulation.

Figure 10A:
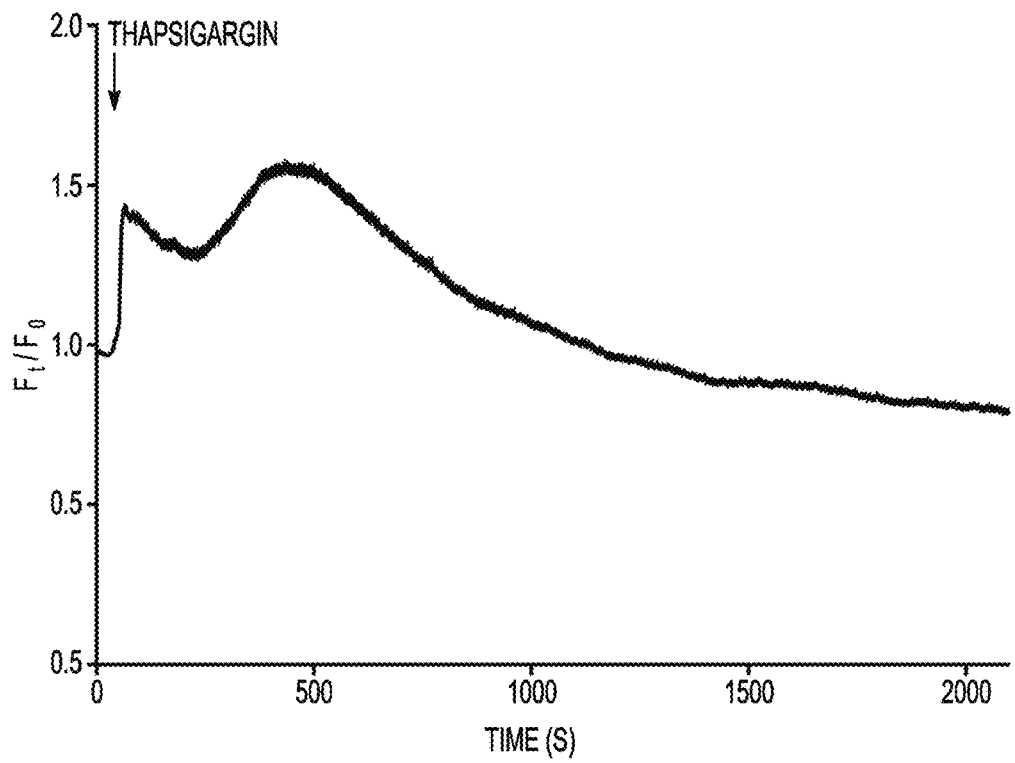
FIGS. 10A-B: Controls for calcium signaling mediated via Magneto2.0. (a) Application of thapsigargin to Magneto2.0-transfected HEK293 cells shown as a time course over 45 minutes. Calcium signaling returns near baseline around 30 minutes. (b) Quantification of maximal calcium fluorescence during magnetic field application in mCherry+ Magneto2.0-p2A-mCherry transfected HEK293 cells. Shown as mean±SEM.
Figure 10B:
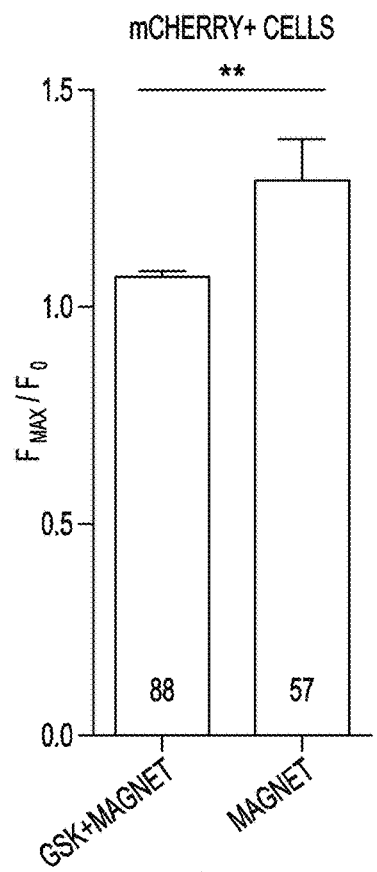

To test this hypothesis more directly, cells were treated with the calcium pump inhibitor, thapsigargin, which releases calcium from intracellular stores and prevents intracellular calcium reuptake (FIG. 10). In the presence of thapsigargin, stimulated Magneto2.0-expressing cells still responded to the application of magnetic fields, but indeed no longer exhibited prolonged calcium waves afterwards, suggesting that the sustained calcium waves observed are due to CICR (FIG. 1f-h).

Next, the change in calcium signaling resulting from magnetic stimulation in was measured in a more direct way, rather than by measurements of maximal calcium fluorescence. Therefore, the change in calcium fluorescence of mCherry+ Magneto2.0-p2A-mCherry transfected cells during magnetic field application was quantified both in the presence and absence of the specific TRPV4 inhibitor GSK205. An approximately 30% increase in calcium fluorescence was observed in response to magnetic stimulation of conductive mCherry+ cells compared to only a 4% increase in the fluorescence of GSK205-treated cells (FIG. 1i), and it was found that approximately 70% of mCherry+ cells produced calcium transients >4%, which is the average maximal response of mCherry+ cells in the GSK205-treated control group (n=3 coverslips, n=58 cells). All observed changes in calcium fluorescence were significantly improved over the poorly trafficked prototype channel (FIGS. 7, 8a). These data demonstrate that Magneto2.0 is a magnetically sensitive, genetically encoded actuator that can manipulate cellular activity in vitro.

These experiments prompted the precise determination of the temporal kinetics of Magneto2.0 activation. To this end, an adeno-associated virus (AAV) was generated to express Magneto2.0 in mammalian cells under control of the cytomegalovirus (CMV) promoter using the double-floxed inverse open reading frame (DIO) approach (CMV::DIO-Magneto2.0). This strategy enables permanent Cre-dependent expression of a reversed lox site-flanked gene through Cre-lox mediated recombination (see FIG. 23). The hippocampi of WT mice were co-injected with AAVs containing CMV::DIO-Magneto2.0 and calcium/calmodulin-dependent protein kinase II alpha (CamKIIa)::Cre-green fluorescent protein (GFP), which expresses Cre recombinase fused to GFP in excitatory neurons.

Figure 2A:
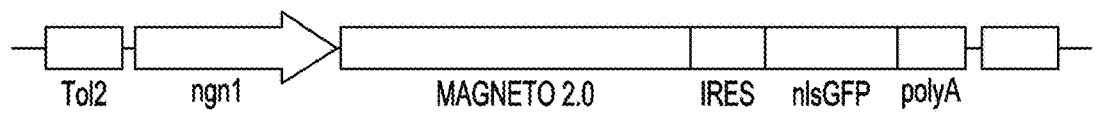
FIGS. 2A-G: Magnetic control over zebrafish tactile behavior in vivo (a) Schematic of construct used to generate transgenic zebrafish. Tol2: transposon site; ngn1: neurogenin-1 promoter; IRES: internal ribosomal entry site; nls: nuclear localization signal; EGFP: enhanced green fluorescent protein; polyA: polyadenylation signal. (b) Behavioral paradigm for zebrafish magnetic stimulation. (c) Coiling rate of 24-36 hpf ngn1::Magneto2.0 fish; unpaired two-tailed t-test, ($t_9$=6.152, p=0.0005). (d) Fold change in coiling of fish cohorts aged 24-36 hpf; one-way ANOVA, Bonferroni post-test ($F_{2,11}$=39.01, $p<0.0001$). (e) Schematic and (f-g) in vivo imaging of Rohon-Beard neuron projections into the skin, n>6 fish examined per genotype. Inset: Magneto2.0+ (yellow) and Magneto2.0- (red) neurons. Data pooled from 2 injections per genotype, shown as mean±SEM. n=17-27 fish per condition; *$p<0.001$.
Figure 2B:
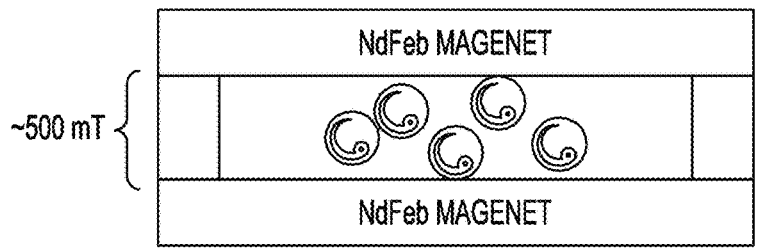
Figure 2C:
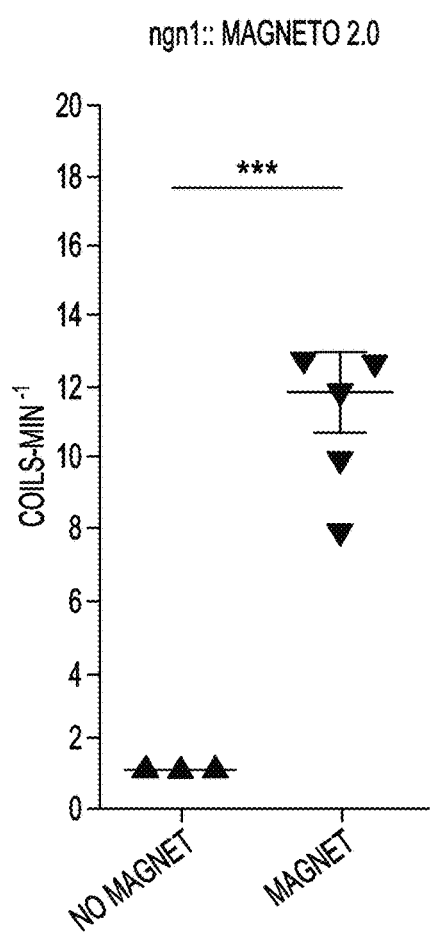
Figure 2D:
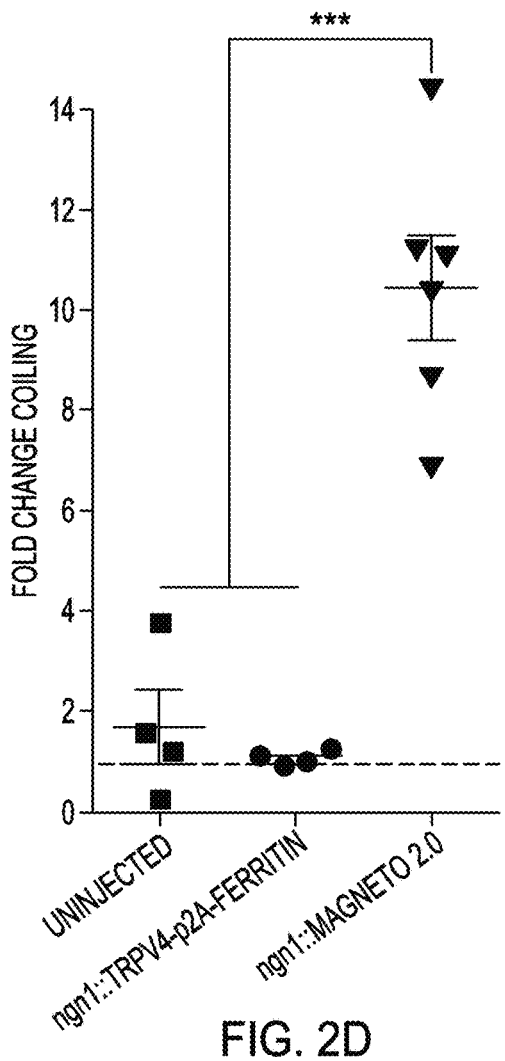
Figure 11A:
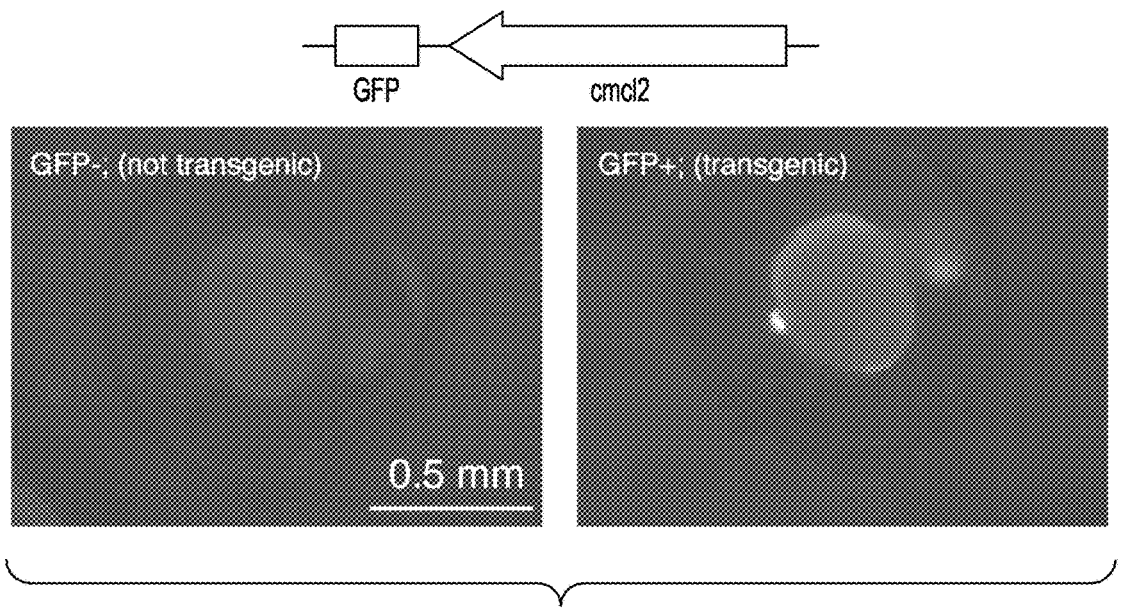
FIGS. 11A-D: Application of Magneto1.0 to zebrafish behavior in vivo. (a) Schematic of trans cardiac myosin light chain 2 (cmcl2)::GFP element and its expression in 24 hpf zebrafish embryos for positive transgenic selection. n>100 fish examined. (b) Schematic of Magneto1.0 construct used—Tol2: Tol2 transposon sites; β-Actin: promoter; IRES: internal ribosomal entry site; nls-EGFP: nuclear localized enhanced GFP. (c) Quantification of the number of coils in WT (uninjected) and β-actin::Magneto1.0 expressing 24 hpf zebrafish embryos. n=43 WT, n=25 β-actin.

Validation of Magneto2.0 function in vivo was begun by determining if one could remotely modulate simple behaviors using magnetic fields. First, Magneto2.0 was transiently expressed in sensory neurons of the zebrafish, Danio rerio (~4.5 Magneto2.0+ neurons per fish, n=10 fish), using regulatory sequences of the ngn1 promoter, which is expressed by touch-sensitive Rohon-Beard sensory neurons (20-21) (FIG. 2a). Mosaic zebrafish were identified expressing Magneto2.0 in Rohon-Beard neurons by selecting for animals that also expressed a co-injectable fluorescent marker in the heart (FIG. 11a). The behavior of ngn1::Magneto2.0 zebrafish was examined in the presence or absence of magnetic fields within a magnetized behavioral testing arena formed by spacing two NdFeB rare earth magnets 6 mm apart (FIG. 2b). It was hypothesized that even if only a few Rohon-Beard neurons were activated by Magneto2.0, the stereotypical escape response would nevertheless induce a coiling behavior, as demonstrated previously (21, Sagasti et al.). Indeed, in response to a 500 mT magnetic field, groups of 24 to 34 hours post fertilization (hpf) ngn1::Magneto2.0 expressing zebrafish larvae coiled more frequently compared to those not exposed to a field (FIG. 2c, movies available online in conjunction with the Nature Neuroscience, vol 19, No. 5 May 2016, Wheeler et al. paper; which entire paper is incorporated by reference herein). In contrast to ngn1::Magneto2.0 fish, which displayed an approximate ten-fold increase in coiling behavior upon magnetic field exposure, there was no observable change in this behavior for either control group—uninjected WT fish or ngn1::TRPV4-p2A-ferritin fish, which bicistronically express independent, unfused TRPV4 and ferritin moieties (FIG. 2d).

Figure 2E:
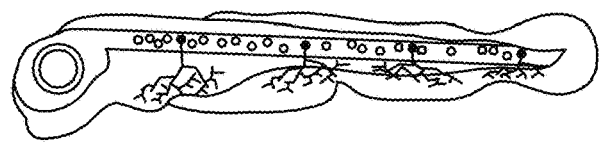
Figure 2F:
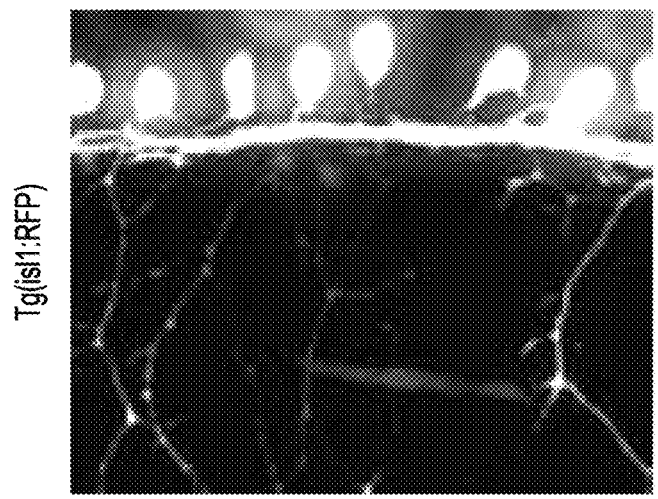
Figure 2G:
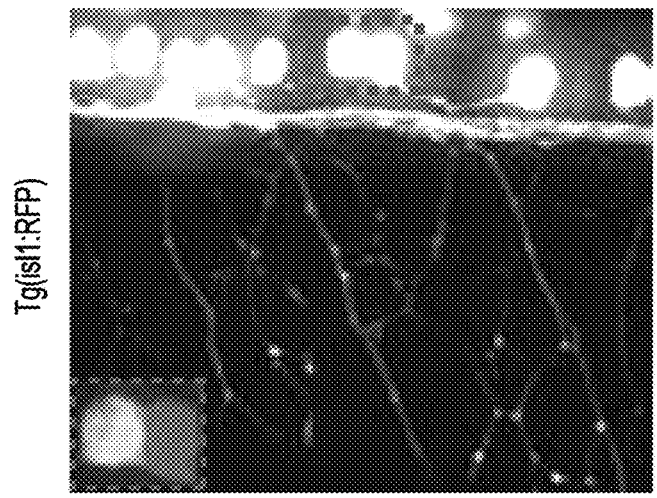

Consistent with in vitro findings, fish expressing the Magneto prototype channel under control of the β-actin promoter exhibited a response that was five-fold smaller than that of fish expressing Magneto 2.0 (FIG. 1b-d). It was confirmed that Magneto2.0 expression did not disrupt normal peripheral projections of Rohon-Beard neurons by examining red fluorescent protein (RFP) expression in sensory neurons of Tg(isl1::rfp) fish and Tg(isl1::rfp);ngn1::Magneto2.0-IRES-nlsegfp chimeric fish (FIG. 2e-g). Together, these results confirm that Magneto2.0 is a viable candidate for remotely controlling neuronal activity in vivo.

To determine if Magneto2.0 is capable of controlling mammalian neural activity, in vivo electrophysiology measurements in freely behaving mice transduced with an AAV1 carrying CMV::DIO-Magneto2.0 were performed, which will express Magneto2.0 in mammalian cells in a Cre-dependent manner. This will determine if Magneto2.0 is capable of activating a large nucleus deep within the brain. To this end, mice expressing Cre recombinase under control of the dopamine receptor 1 promoter (D1R::Cre) were used, which is expressed in approximately half of the medium spiny neurons (MSNs) of the striatum (24). Striatal neurons of D1R::Cre mice were transduced with an AAV1 carrying Magneto2.0 and two weeks post-viral injection extracellular single-unit recordings were performed with tetrode microdrives on Magneto2.0 expressing striatal cells in freely behaving mice and examined the effects of magnetic stimulation on neural firing (FIG. 3b). For this assay, a magnetized chamber was designed consisting of NdFeB magnets embedded in the chamber walls (FIG. 3c) and quantified the firing rates of striatal neurons under three conditions: (1) at baseline without magnetic stimulation, (2) during exposure to 50-250 mT magnetic fields within the chamber, and (3) post-magnetic field exposure.

Figure 3E:
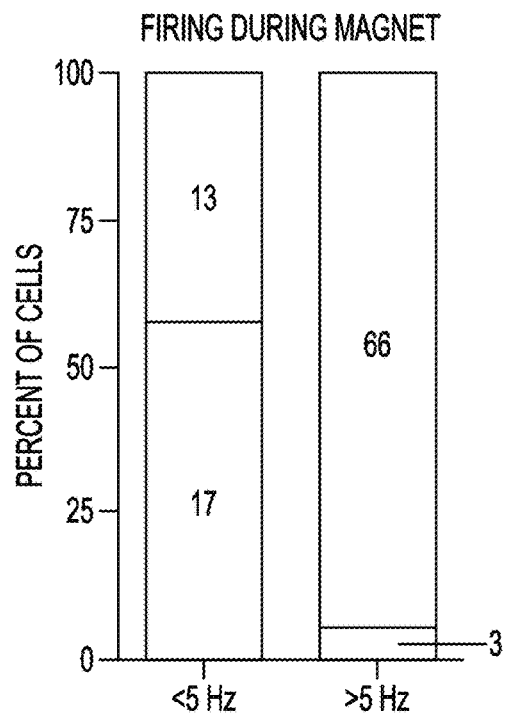
Figure 3G:
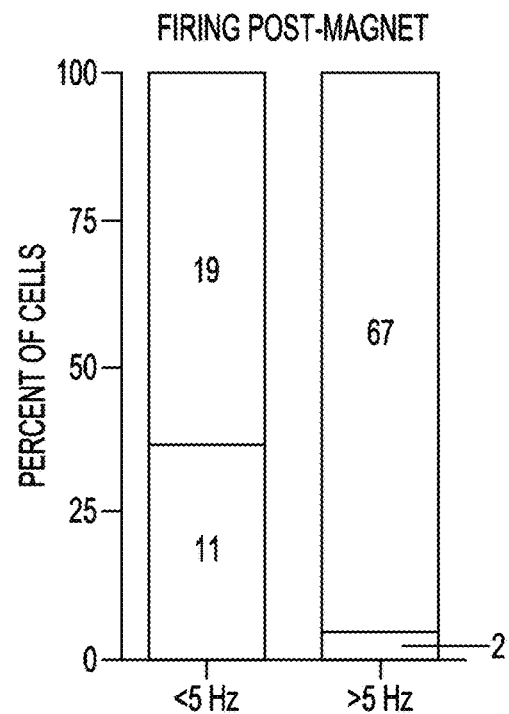
Figure 3F:
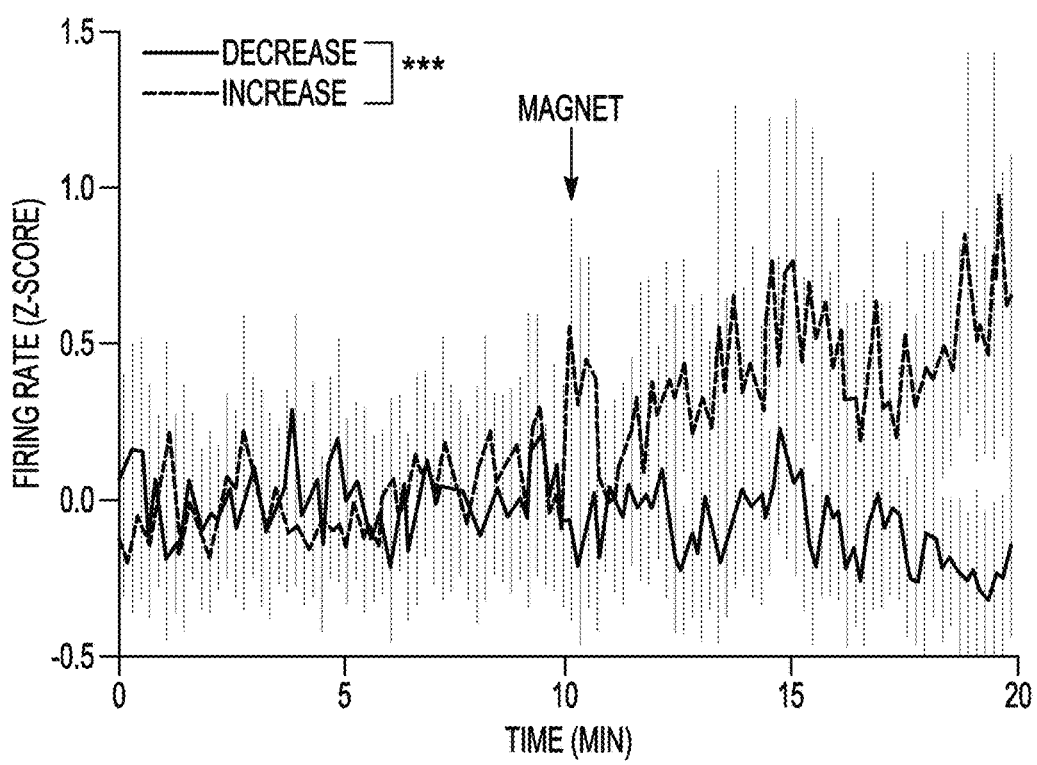

Recorded cells were classified into two main groups based on firing rate: slow-spiking (<5 Hz) and fast-spiking (>5 Hz) neurons with mean firing rates of 2.2±0.3 Hz and 6.9±0.1 Hz, previously described as putative MSNs and GABAergic interneurons, respectively (25). Exposure of these mice to magnetic fields produced an approximately 75% increase in the overall firing rate of slow-spiking putative MSNs. Of note, this population likely includes untransduced (i.e. Magneto2.0-negative) D1R− and D2R− expressing MSNs, which would dilute the magnitude of the population response (FIG. 3d-f). Importantly, the firing rate of putative GABAergic interneurons remained constant (FIG. 3d-e). Subsequent to magnetic stimulation, ~65% of putative MSNs returned to baseline firing rates, while the putative interneuron firing rate again remained at baseline (FIG. 3g). Finally, an increase in the firing rate of slow-spiking, but not fast-spiking, neurons of the striatum following systemic administration of the D1R agonist, SKF81297 was observed (FIG. 11a), suggesting that the D1R+ population responsive to magnetic fields are indeed slow-spiking neurons. Together, these data demonstrate that Magneto2.0 is capable of controlling neural firing in deep brain regions in response to magnetic fields.

Next, it was sought to determine whether Magneto2.0 dependent control of neural activity in vivo could translate to control over complex mammalian reward behaviors regulated by dopamine signaling (26). While optogenetic studies have implicated the dopaminergic signaling axis in causally mediating reward behavior (27), it is unclear whether activation of postsynaptic D1R+ neurons is sufficient for controlling this effect. For instance, optogenetic stimulation of one subset of striatal D1R+ neurons is not causally responsible for induction of conditioned place preference (CPP) (24). Conversely, studies using systemic pharmacological manipulations with D1R agonists confirm that activation of D1R+ neurons is sufficient to evoke CPP (28-29), suggesting that broadly activating D1R+ neurons may cause reinforcing behaviors. Optogenetic techniques are intrinsically limited in the number of neurons that can be activated simultaneously and pharmacological approaches lack genetic specificity. However, a magnetogenetic paradigm circumvents both obstacles simultaneously allowing resolution of this discrepancy with cell-type specificity and a real time behavioral output.

Figure 11B:
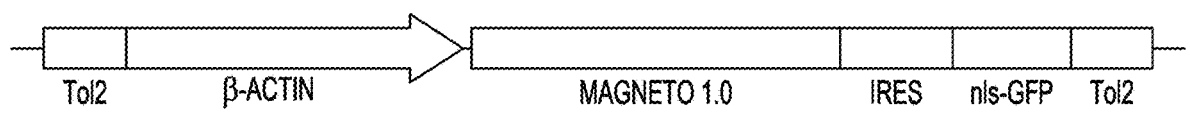
Figure 11C:
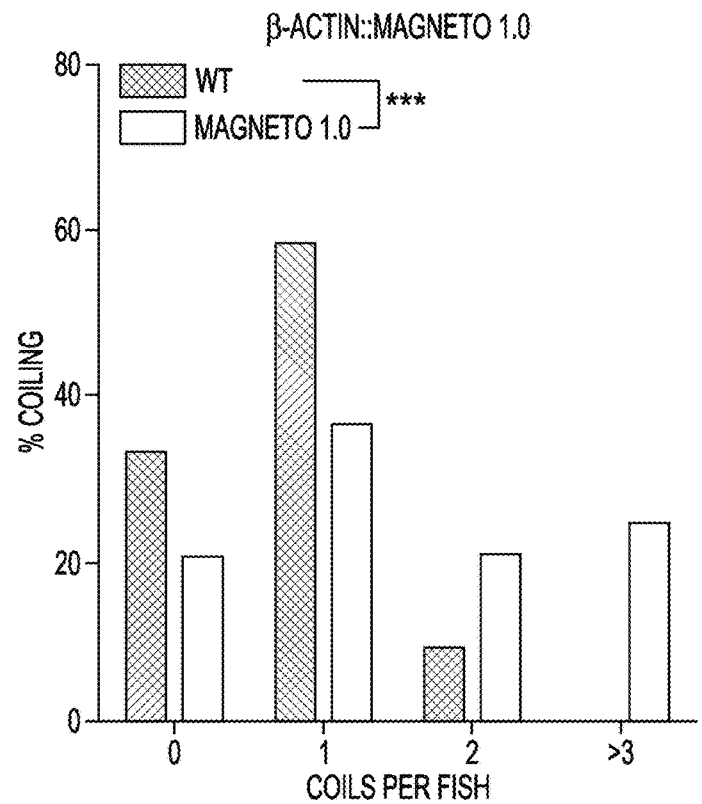
Figure 11D:
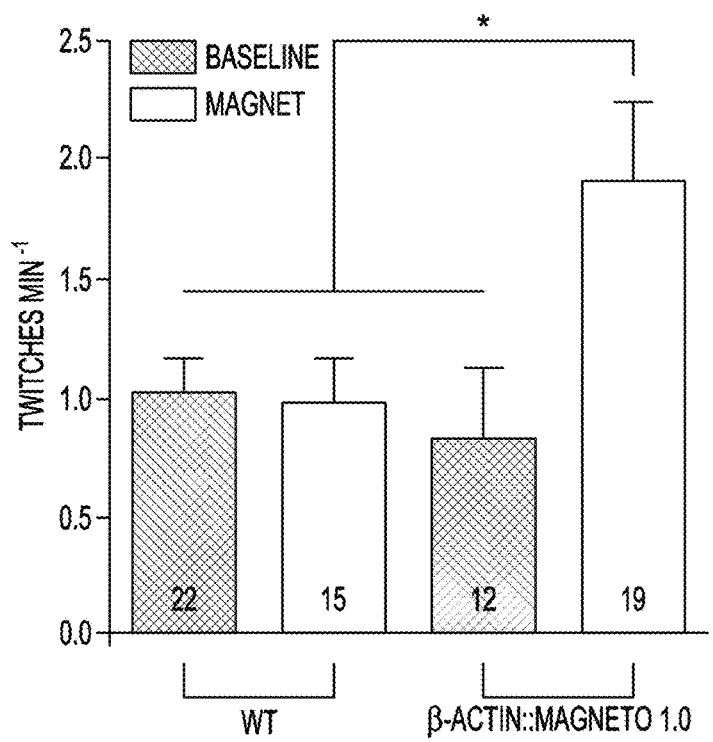

The sufficiency of D1R+ neurons in eliciting reward conditioning was tested by unilaterally injecting the striata of WT and D1R::Cre mice with an AAV1 carrying CMV::DIO-Magneto2.0 and subjecting the mice to a real time place preference (RTPP) assay where they could choose between a magnetized arm, lined with several permanent NdFeB magnets, and a non-magnetized arm (FIG. 4a). It was observed that Magneto2.0 expressing D1R::Cre mice showed preference for the magnetized arm of the RTPP chamber in contrast to WT mice (one-way ANOVA, p=0.0152), which exhibited no preference (FIG. 4b-d). Moreover, removal of the magnets from the chamber eliminated the preference of Magneto2.0 expressing D1R::Cre mice for either arm, a response identical to WT mice (FIG. 4b, bottom panel), demonstrating that RTPP is dependent on D1R stimulation. No differences were measured in overall locomotion between unilaterally injected WT and D1R::Cre mice using a modified open field assay (FIG. 11b-c). These data show: (1) that broad activation of D1R+ neurons of the striatum is sufficient to induce behavioral conditioning and (2) that Magneto2.0 can be used for remote control of complex mammalian behaviors mediated by deep brain nuclei in freely moving mice.

In total, provided herein is an engineered and optimized genetically encoded magnetogenetic actuator, Magneto2.0, and its application to the nervous system in freely behaving animals. This is the first demonstration of bona fide magnetic control of the nervous system using engineered actuators, which was confirmed electrophysiologically and behaviorally using both zebrafish and mice. While magnetogenetic control over insulin signaling using a parallel approach requires tens of minutes in anesthetized mice (11), it was shown that Magneto2.0 controls both neural firing rates and behavior on a rapid and physiologically relevant timescale (11). The single-component magnetogenetic system represents a significant advance in the ability to study neural circuits with relative ease as broad populations of genetically defined cells can be simultaneously activated remotely in freely behaving animals. Magneto2.0 was applied to the study of reward behaviors to directly measure the behavioral consequences involved in remotely modulating large populations of cells participating in specific neural circuits (30). The findings also shed light on the sufficiency of D1R+ neurons to control reinforcing behaviors. Magneto2.0 represents an important advancement for a novel class of magnetogenetic remote controlled actuators. This magnetogenetic actuator will position the field to better understand neural development, function, and pathology.

Example 1 Methods

Mice Information

All animal experiments were conducted in accordance with the University of Virginia IACUC. All mice were maintained on a C57Bl/6 background. Mice were housed in a vivarium on a 12-hour light/dark cycle. Mice were housed at between 1-3 mice per cage. Viral injection experiments using D1R::Cre mice were conducted starting at 8 weeks of age. All mice used in this study were injected between 8-10 weeks of age. Only male mice were used in this study.

Zebrafish Husbandry

All animal studies were approved by the University of Virginia IACUC. Zebrafish strains used in this study were: AB* and Tg (isl:rfp). Embryos were raised at 28.5° C. in egg water or embryo medium and staged according to hour post fertilization (hpf) or days post fertilization (dpf). Embryos of both sexes were used for experiments (3).

Molecular Biology

Molecular biology was performed using standard protocols. Plasmid DNA was purified using kits from Qiagen. Restriction enzymes were purchased from New England Biolabs. Amplification of template DNA was performed with Phusion Flash (Life Technologies, F-548) and sequenced by GeneWiz. For S4-S5 fusion proteins, site-directed mutagenesis using Quickchange II XL Site-Directed Mutagenesis (Agilent) was performed on TRPV4 to introduce a unique BamHI site, into which a successive series of DNA linkers was inserted to gradually expand the linker region flanking TRPV4 and ferritin.

Rat TRPV4 was obtained from Addgene vector: #45751, a gift from Robert Lefkowitz. To generate AAV expression vectors, the Addgene vector: #35507, a gift from Karl Deisseroth, was modified. A human ferritin H-L fusion gene was designed according to a previous study (4) and synthesized by IDT. Other than AAV vectors, mammalian expression vectors were maintained in the pcDNA3.0 backbone. Fish expression vectors were maintained in pDestTol2CG2 and all entry vector maps are freely available from a genetics website at the University of Utah. Relevant plasmids used in this study will be deposited in Addgene.

Magnets and Magnetic Field Strength Measurement

Electromagnets of varying sizes and strengths were purchased from Ebay (seller ID: pawnnew). Permanent N42 or N52 grade NdFeB magnets were purchased from CMS Magnetics on Amazon.com. Gaussmeters (AlphaLabs, Inc.) were used to determine the field strength of the electromagnets over distance for each experiment. For the in vivo zebrafish and mice behavioral experiments using permanent NdFeB magnets, an online magnetic field calculator (K&J Magnetics) or a Gaussmeter (AlphaLab, Inc.) was used.

Cell Transfection and Cell Culture

HEK293 cells were a gift from the University of Virginia tissue culture core. Cells used in this study were authenticated and checked for mycoplasma contamination. Cells were transfected using Lipofectamine 2000 (Invitrogen) according to standard protocols. Low passage (<40) HEK293 cells were transfected for 1-2 hours in well plates, trypsinized for 5 minutes using 10% trypsin, and replated onto glass coverslips in fresh DMEM:F12 media (Life Technologies) containing 1 mM non-essential amino acids (Gibco), 1 mM sodium pyruvate (Gibco), 10% FBS, and 1× penicillin/streptomycin (Gibco).

In Vitro Magnetic Calcium Imaging

Calcium imaging was performed largely as described previously (5). Briefly, transfected cells were plated onto glass coverslips, incubated overnight in a humidified incubator kept at 37° C. and 10% $CO_2$. Cells were washed 3× with calcium imaging buffer (CIB) solution (6) (105 mM NaCl, 3 mM KCl, 2.5 mM $CaCl_2$, 0.6 mM $MgCl_2$, 10 mM HEPES, 1.2 mM $NaHCO_3$, 100 mM mannitol, and 10 mM glucose, adjusted to pH 7.45 with NaOH) and loaded with 3 µM Fluo-4 diluted in CIB for 30 minutes at 37° C. Cells were then washed of the dye 3× with CIB and de-esterified for 30-60 minutes at 37° C. Coverslips were then loaded into customized imaging chambers and imaged at 10× magnification for analysis. Ruthenium red (RR), a TRP channel pore blocker, (Sigma) was used at a concentration of 10 µM and cells were incubated with RR for ~2-3 minutes in the imaging chambers before imaging. For calcium-free media experiments, calcium was replaced with 10 mM EGTA, and cells were washed and incubated with calcium-free media. The TRPV4 specific antagonist, GSK205, was purchased from Calbiochem (616522) and used at a concentration of 10 µM. Cells were incubated in GSK205 for 15 minutes at 37° C. before calcium imaging.

Figure 5:
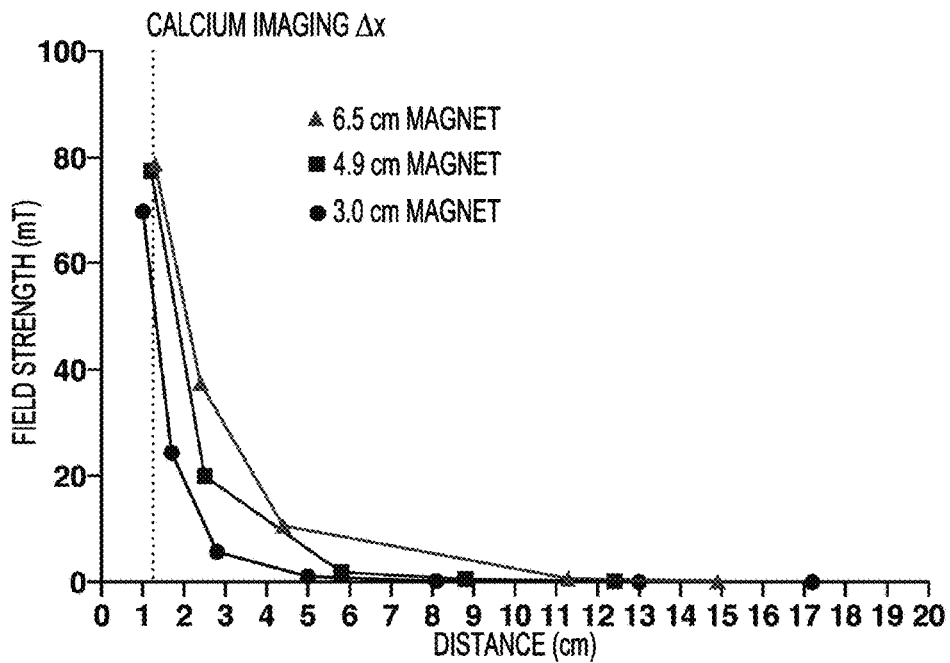
FIG. 5: Measurement of electromagnet strength over distance. Empirical determination of the strength of several electromagnets over distance. Dashed line represents distance between HEK cells and electromagnet during calcium imaging assays. A 3 cm diameter magnet was used for all calcium imaging assays. Δx represents distance between magnet and cells used in calcium imaging.

A magnetic stimulus was delivered using purchased 3 cm electromagnets (eBay, sellerID: pawnnew) ruled for continuous duty, 12 VDC, 5 W, and 10 kg of pull-force. We situated the magnet directly above the imaging chamber during imaging. Using a Gaussmeter (AlphaLab Inc.), we calculated the magnetic field experienced by the cells (~1.25 cm away from the magnet) to be roughly 40-50 mT (FIG. 5).

Imaging was performed by recording 30 seconds of baseline fluorescence and then turning on the magnet for 3 pulses of 10 seconds each or 6 pulses of 10 seconds (0.1 Hz, total time of 30-60 seconds, 90% duty cycle), using a standard DC powered delivery system. Coverslips were not analyzed if they significantly shifted during imaging.

Cells were randomly selected from an image field. Quantification was performed by averaging 30 seconds of baseline fluorescence measurements with no applied magnetic field followed by quantification of the largest three fluorescence values following magnetic stimulation. The three peak values were normalized to the average baseline fluorescence before magnetic stimulation to compute a relative fold change for each cell. Fold change was normalized to background by respectively scaling all values by the average fold change in the background (if applicable) during magnetic stimulation.

Thapsigargin Calcium Imaging

HEK cells were prepared for calcium imaging as above. Thapsigargin was purchased from Sigma (T9033) and used at a working concentration of 1 µM, diluted 1:1000 in CIB. A 30-second baseline of calcium fluorescence was recorded before direct application of 800 µL of thapsigargin into the calcium imaging chamber. Calcium fluorescence was recorded for 1 hour after thapsigargin addition.

Magneto-expressing cells were treated with thapsigargin and incubated at 37 C for 30 minutes before calcium imaging as thapsigargin-induced calcium release remained steady at 30 minutes after application. Cells were stimulated with magnetic fields as above: 10-second pulses of 50 mT field for 30 seconds of total field exposure.

Fish Injection

AB* or Tg(isl:rfp) embryos were injected at the one-cell stage with 1-2 nl of a working stock of 12.5 ng/ul for each construct. At 24 hpf, embryos were screened for cmcl2::egfp+ transgenics. Imaging of cmcl2::egfp expression was performed on every zebrafish embryo examined (n>30 fish).

In Vivo Zebrafish Imaging

Imaging was performed as described previously (7). Briefly, a Quorum WaveFX-XI spinning disc confocal system (Quorum Technologies Inc.) was used, equipped with a 40× water objective (NA=1.1) on a motorized Zeiss AxioObserver ZI microscope. Images were processed with Metamorph. N>10 fish imaged per genotype.

Zebrafish Whole Mount Immunostaining

Zebrafish were fixed and immunostained according to the protocol described previously (7). The antibody used was rabbit anti-GFP (Invitrogen, A-6455) at a dilution of 1:1000. The secondary antibody was donkey anti-rabbit Alexa 488 used at 1:600.

Microscopy

Imaging for calcium imaging and immunocytochemistry was performed on a Leica SP5 confocal with white light laser. Calcium imaging was performed using 10× magnification.

Immunocytochemistry

Cells plated on coverslips were washed 3× with 1×PBS, fixed in 4% PFA for 1 hour at RT, washed 3× with 1×PBS, and mounted on slides with Fluoromount-G with DAPI (Southern BioTech). Immunocytochemistry for each iteration of trafficking signals was performed on two independent populations of transfected HEK293 cells.

Zebrafish Behavioral Tests

Injected fish were maintained on an AB* background strain. Zebrafish embryos were behaviorally tested between 24-34 hours post fertilization (hpf). Two 2"×0.5"×0.25" N52 grade NdFeB permanent magnets were oriented such that one south and one north pole were oriented towards the fish over a fixed distance of ~1 cm. Fish were maintained in egg water during the course of behavioral testing and a 30 fps video was taken using an Axio Zoom.V16 fluorescent stereo zoom microscope. Fish were randomly selected from their groups for behavioral analysis. The videos were manually scored by counting the number of coils made by each fish over the length of the video and normalized as a rate of coiling by dividing the number of coils by the length of the video. Animals tested had no prior history of behavioral testing. Animals were tested once each. Exclusion criteria for analysis consisted of stereotypy such as continuous coiling during the recording of the movie. Two uninjected WT animals were excluded from the analysis given these criteria. Behavioral testing was performed during the day at consistent times (8 am-4 pm).

Viral Constructs and Stereotaxic Injection

Viral constructs were created using an AAV backbone obtained from Addgene (#35507, a gift from the Deisseroth lab). A CMV promoter was substituted and a small pA sequence was used (8) to minimize size of the vector. The AAV1-CMV-DIO-Magneto2.0-pA virus used in this study was produced in the University of Pennsylvania vector core. Four injections of 1 of ~5×10$^{12}$ titer AAV1 virus was injected unilaterally into the striatum of WT and C1R::Cre mice using a 30G Hamilton syringe, stereotaxic alignment system (Cartesian Research, Inc.), and automated delivery system (World Precision Instruments) while mice were under 2% isoflurane anesthesia on a heating pad. Unilateral injection was performed at (M/L: +1.6, A/P: +0.98) relative to Bregma and four 1 µL injections were performed at depths of −4.75, −3.75, −2.75, and −1.75 mm over 40 minutes at a rate of 100 nL/min. After the final injection, the syringe remained in the brain for 10 minutes, raised 0.5 mm where it remained for 5 minutes, then removed. Mice were administered 3 mg/kg ketoprofen post-injection and for 3 subsequent days and permitted to recover on a heating pad before being returned to their home cages. All animal surgery was consistent with the UVa IACUC guidelines.

Single Unit Recordings In Vivo in Freely Moving Mice

In vivo electrophysiology was performed largely as described previously (9). HS-16 four-tetrode microdrives (Neuralynx) were implanted in anaesthetized mice by using stereotaxic coordinates for the striatum described above except two injections of 1 µL each were made at depths of −4.75 mm and −4.25 mm within the brain; the head stage was installed at an initial depth of −4 mm. After 2 weeks of recovery, mice were connected to a digital Lynx (10S) acquisition system through an HS-16 headstage preamplifier (Neuralynx), and signals were amplified and filtered (600-6000 Hz). Data were acquired by using Cheetah acquisition software (Neuralynx). Baseline putative D1R neuron firing properties were recorded for 10 min in the non-magnetized arm of the custom-made place preference chamber, followed by 10 min in the magnetic arm of the chamber, and then 10 min of a second baseline recording period. Tetrodes were lowered 50 µm daily during scanning for distinct units. Offline Sorter software (Plexon) cluster analysis was used to isolate units. Clustered waveforms were subsequently analyzed with MATLAB (MathWorks). Baseline activity recordings (10 min) were used to identify putative D1R neurons that exhibited firing rates below 5 Hz. Behavioral testing was performed at consistent times daily (9 am-1 pm) for 3-4 weeks.

After the completion of these three recording sessions, the mice were injected with the D1R agonist SKF81297 (Cayman Chemical, diluted to 3 mg/kg in saline, i.p.). 15 minutes after the agonist had been administered, a final 10-minute recording period in the non-magnetized arm of the place preference chamber was completed. Drug injection experiments were performed only during a 5-day period following the triplicate recording procedure performed above (baseline, magnet, post-magnet). Data were not included in the triplicate analysis (FIG. 3) once a mouse had been injected with SKF81297. Data in Supplementary FIG. 7a using drug are from a single mouse.

Mouse Behavioral Testing

All testing was conducted was during the mouse light cycle at consistent times (9 am-5 pm).

Open Field

A custom-built open-field chamber was constructed by A. Spano and M. Wheeler (9"×9"), where four 10 cm magnets fit into the floor, and were covered with a 0.5 cm wooden platform on which the mouse could walk. Each magnet was connected to an independent power supply delivering roughly 2.5 A and 30V of power, and generating a magnetic field of roughly 150 mT. Mice were placed in the chamber for 5 minutes and baseline recordings of locomotion were measured. Magnets were turned on for 5 minutes to measure responses to the magnetic field. Each mouse was tested in the assay 1 time for a total of 10 minutes per mouse.

Real Time Place Preference (RTPP)

The two arms of the assay were custom-built by A. Spano and M. Wheeler (1.5" wide (internal diameter)×9" long). Five permanent NdFeB magnets (Four 2"×0.5"×0.25" magnets, one 1"×0.5"×0.25" magnet) were embedded into each wall of the magnetized arm, recessed at a depth of 1 cm. Each 2"×0.5"×0.25" magnet delivered roughly 250 mT and the magnetic field strength was roughly 50 mT in the center of the magnetized arm. The magnets were placed at a height of 0.44"-0.64" above the floor of the chamber to primarily expose the mice's heads to the field. Mice were placed into the chamber in the center of the two arms and permitted to explore for 2 minutes before recording began. The testing session lasted a total of 10 minutes. The two arms appeared identical except for the presence/absence of magnets.

For D1R::Cre mice experiments where the magnets were removed from the chamber, two cohorts of 3 mice each were used. In the first cohort, the mice were first exposed to the magnet on Day 1, then the magnets were removed and preference was assessed on Day 2. In the second cohort, D1R::Cre mice injected with AAV1 CMV::DIO-Magneto2.0 were trained in the chamber lacking magnets on Day 1, then tested with the magnetized chamber on Day 2. The magnetized/non-magnetized arms were transposed for each cohort to ensure that there was no preference for either side in the testing chamber.

Mouse Behavioral Data Analysis

Mouse behaviors were measured using Ethovision, which is an automated tracking, recording, and measurement software package. Following each testing session, linear velocity was measured (nose-point relative to center-point) with and without magnetic field for the open field assay. Place preference was calculated as the percent of time a mouse spent in the magnetized vs. non-magnetized arm. For RTPP experiments where mice were exposed to the chamber without any magnets installed, the "magnetic arm" was chosen as the side where the magnet was placed in the testing session and numerical values were then calculated.

Statistical Methods

Data were assumed to be normally distributed except in FIG. 3e, g and FIG. 10c. Specific statistical tests are explicitly stated in the Figure Legends. Sample sizes were taken as adequate for field standards. No blinding was performed for data analysis or behavioral testing but automated and randomized quantification was performed where applicable.

Example 2

Cellular networks in general, and neural networks in particular, exhibit dynamic properties that enable rapid transitions between multiple activity states. In order to recapitulate these dynamic activity states via artificial actuator technologies, development of actuators that can regulate activity in multiple directions is essential. Currently, opto- and chemogenetic toolboxes are equipped with both excitatory and inhibitory receptors that augment dynamic control over neuronal activity. However, because optogenetic technologies are invasive and chemogenetic technologies lack temporal precision, it is important to develop remotely controlled actuators to achieve non-invasive, temporally precise stimulation. Recently, remote control over neuronal activity by radiogenetic (Stanley, Chen) or magnetogenetic actuators (Wheeler, Stanley) allowed unprecedented control over the activity of genetically specified populations of cells, and even in freely behaving animals (Wheeler et al.). While magnetogenetics provides genetic and temporal precision comparable to optogenetics, the magnetogenetic toolkit lacks the breadth of opto- and chemogenetic actuators. In expanding the repertoire of magnetogenetic tools, it is important to engineer next-generation actuators sensitive to tissue penetrant magnetic fields that can exert broad control over a range of neural activity states. To this end, the first magnetogenetic inhibitory actuator was developed by tethering the mechanosensitive two-pore domain K+ channel, TWIK-related K+ 1 (TREK-1; human mRNa accession numbers: NM_001017424; NM_001017425; NM_014217; human protein accession numbers: NP_001017424.1; NP_001017425.2; NP_055032.1; mouse accession numbers: NM_001159850; NM_001281847; NM_001281848; NM_010607; NP_001153322.1; NP_034737.2; all which sequence are incorporated herein), to the paramagnetic protein, ferritin, generating a magnetically sensitive ion channel we term "Professor X" (ProfX). Disclosed herein is the function of this channel in vitro, electrophysiologically, and in vivo in both zebrafish and mice.

In order to engineer an inhibitory magnetically sensitive ion channel, we suspected that the mechanosensitive properties of K+ channels activated by stretch were exploited. While another study has generated K+ channels weakly sensitive to magnetic fields using exogenously applied nanoparticles directed at the TREK-1 S1-S2 extracellular loop (Hughes et al. 2008), it was believed that crystal structure information regarding mechanosensitive K+ channel function would enable a more directed construction of an inhibitory magnetogenetic actuator (MacKinnon(×2), Prozac). Given that previous studies indicate the dynamic gating properties of S4 and the carboxyl (C)-terminus of TREK-1 and other mechanosensitive K+ channels, it was hypothesized that coupling ferritin to the TREK-1 C-terminus would yield a highly sensitive inhibitory magnetogenetic actuator (FIG. 16).

Figures 14A, 14C, 14E:
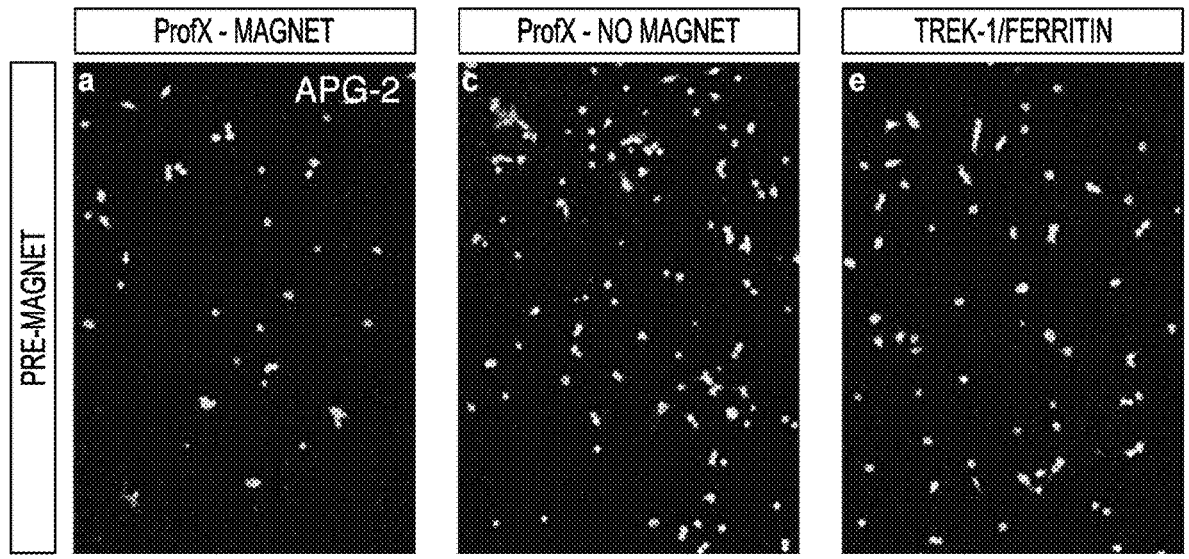
Figures 14B, 14D, 14F:
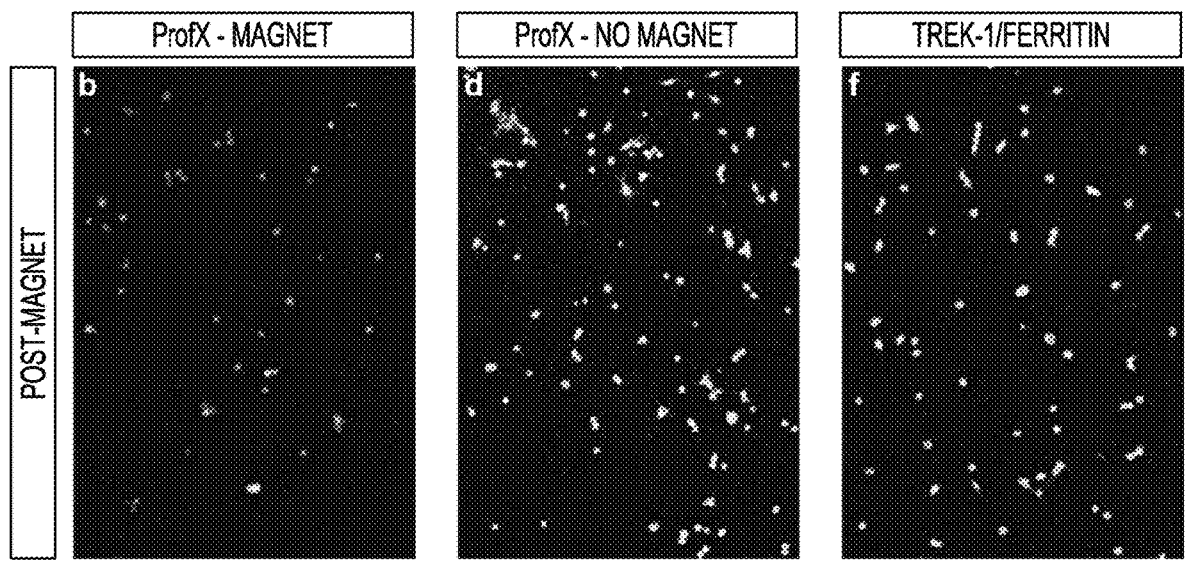
Figure 14G:
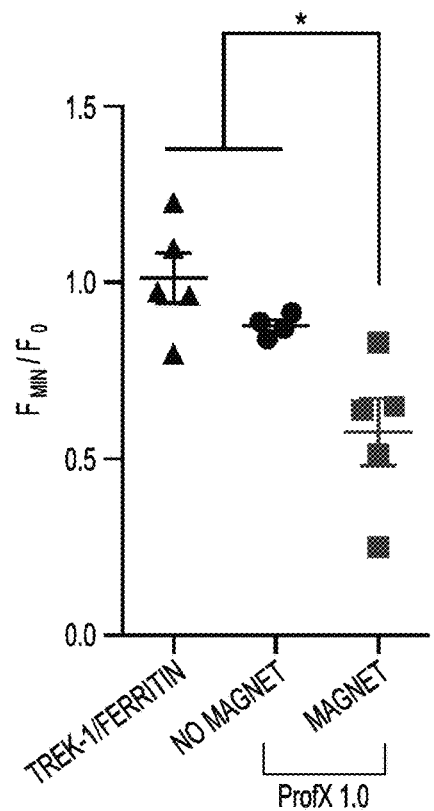
Figure 14H:
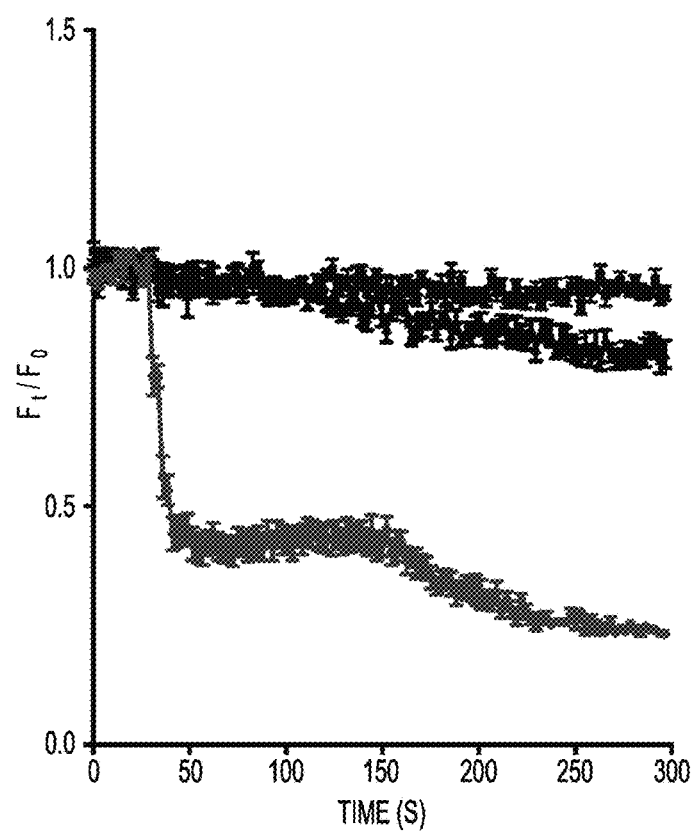

First, a TREK1-ferritin fusion protein was engineered, expressing a membrane trafficking signal (TS) on the ferritin fusion gene C-terminus (FIG. 17), which has been shown to improve the membrane expression of optogenetic and magnetogenetic actuators (Gradinaru, Wheeler). The TREK1-ferritin-TS was called "ProfX" and viability of mammalian cells transfected with ProfX was examined. It was determined that mammalian human embryonic kidney (HEK) 293 cells are stable for at least 5 days in vitro when transfected with ProfX (FIG. 18). The function of ProfX was examined using in vitro K+ imaging. HEK293 cells were loaded with the fluorescent potassium-binding dye, APG-2, and examined K+ fluorescence as a function of magneto-stimulation. HEK293 cells were stimulated with a 40-50 mT magnetic field delivered by an electromagnet. It was hypothesized that if ProfX responds to magnetic fields, a reduction in APG-2 fluorescence would be observed, signifying extracellular rectification of K+. Indeed, a rapid reduction in K+ fluorescence was observed only in magnet exposed ProfX-transfected cells (Example 2, FIG. 14A) but not control cells (Example 2, FIGS. 14C-F), which included unstimulated ProfX-expressing cells and magnetically stimulated cells expressing independent TREK-1 and ferritin genes (FIG. 14g-h). These data suggest that ProfX is a magnetically sensitive inhibitory ion channel capable of modulating cellular activity.

Figure 15A:
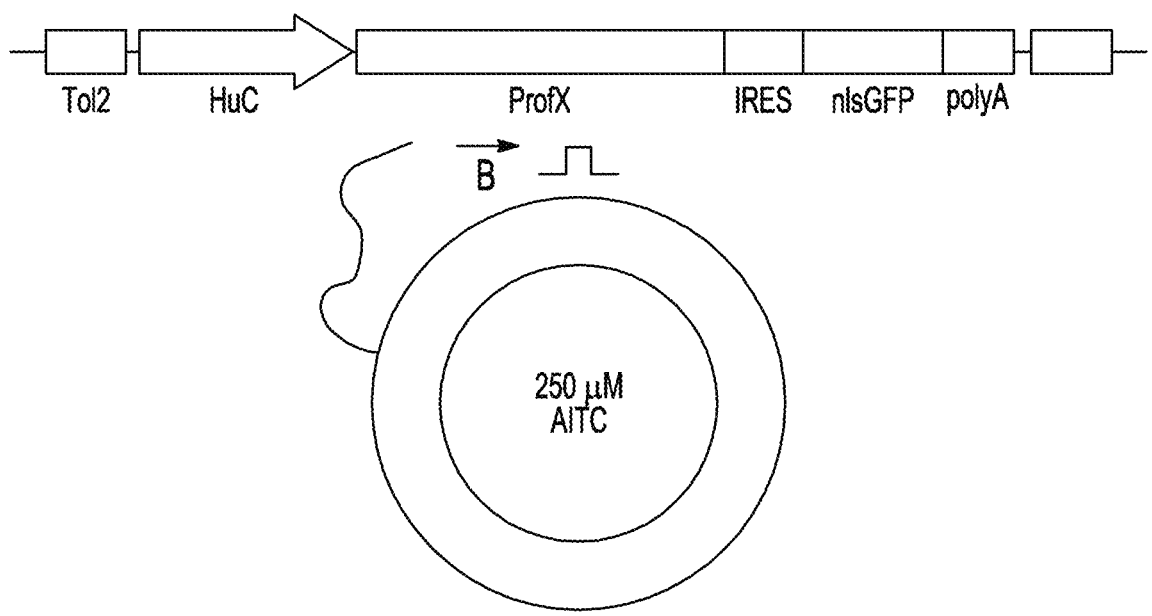
Figure 15B:
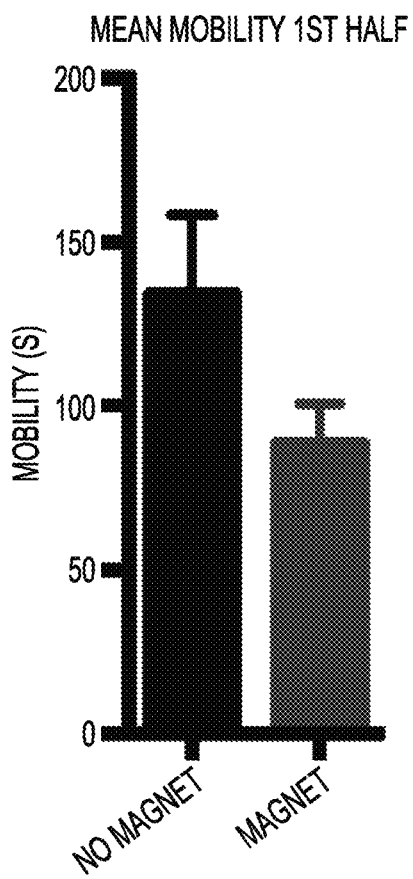

To become a valuable inhibitory actuator, ProfX must be capable of suppressing neuronal activity in vivo. To test whether ProfX can suppress neuronal activity in awake and behaving animals, a behavioral paradigm was developed that would induce swimming in 72-hour post-fertilization (hpf) zebrafish. Individual 72 hpf zebrafish were placed in a petri dish containing 250 μM mustard oil (MO), which has been shown to induce swimming behaviors (Prober et al. 2008), and the petri dish was placed on top of an electromagnet (FIG. 15a). The zebrafish expression construct, which was designed to express ProfX pan-neuronally under control of regulatory elements of the HuC promoter (FIG.

Figure 15C:
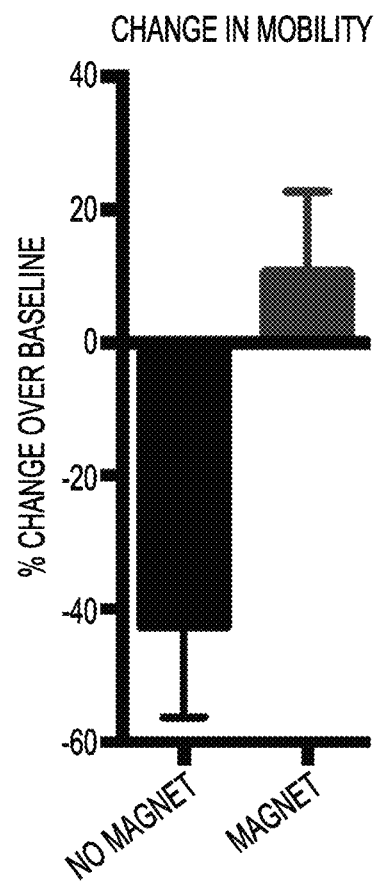
Figure 15D:
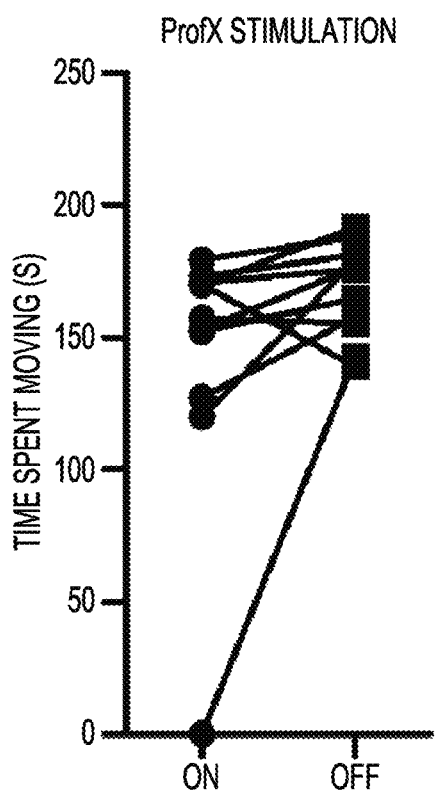
Figure 15E:
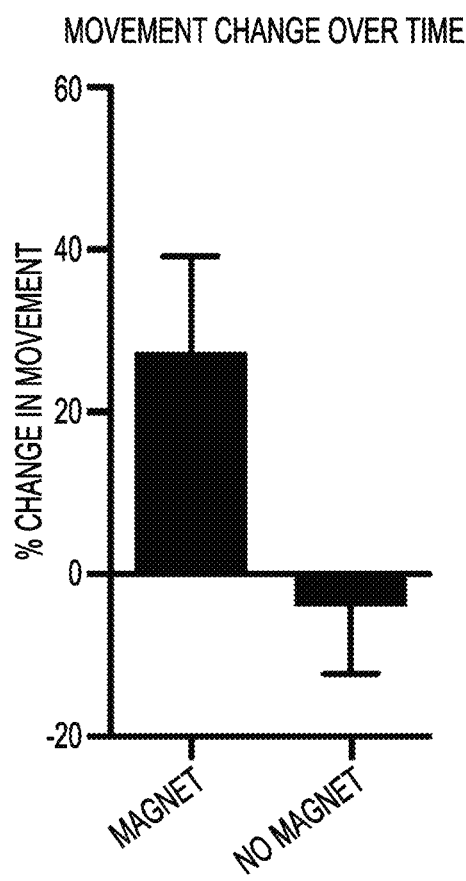

15b). It was hypothesized that if ProfX suppresses neural activity, a reduction in swimming behavior would only be observed in magnetic field exposed ProfX-expressing fish. Consistent with ProfX function in vitro, a reduction in locomotive behaviors in ProfX-expressing fish in response to magnetic field stimulation was observed when compared to untreated ProfX-expressing fish (FIG. 15c). Moreover, while non-magnetic field exposed fish did not change their activity in MO over time, ProfX-expressing magnetic field treated fish increased their activity once the electromagnet delivering the magnetic field was turned off, demonstrating that ProfX can suppress motor activity in response to magnetic fields (FIG. 15b-e). These data suggest that ProfX is a robust tool for remotely controlling neuronal activity in vivo.

Next it was tested whether ProfX functions analogously in the mammalian nervous system by utilizing an electrophysiological approach in mouse brain slices. First, a Cre-dependent adeno-associated virus (AAV) was generated by using the double inverted open reading frame (DIO) approach, where Cre recombination causes an inverted gene to flip into coding orientation (FIG. 3a). AAV1 vector was used to deliver ProfX under control of the ubiquitous cytomegalovirus (CMV) promoter with a 3' woodchuck hepatitis virus posttranscriptional response element (WPRE) and polyadenylation (pA) signal to stabilize ProfX expression in vivo. An AAV1 containing CMV-DIO-ProfX-WPRE-pA with an AAVXXX containing CaMKIIa::Cre-EGFP was delivered into the mouse hippocampus to induce ProfX expression in excitatory hippocampal neurons (not shown). Next, the membrane voltage of patch-clamped GFP+ hippocampal neurons was recorded, which presumably express ProfX. Normal baseline membrane voltage was observed, as well as a significant hyperpolarization of GFP+ neurons in response to magnetic field stimulation in co-injected neurons (Cre/ProfX), but not in slices singly injected with ProfX (FIG. 3b). Similarly, we recorded magnetic field dependent currents from neurons transduced with ProfX and Cre, but neurons transduced with ProfX alone. These data demonstrate ProfX controls mammalian neural activity with temporal precision in a magnetic field dependent manner.

ProfX was validated in the hippocampus (entorhinal cortex), which is a common brain region afflicted by seizures.

In sum, described herein is the design and validation of the first inhibitory magnetogenetic actuator both in vitro and in vivo. These data, together with previous work engineering Magneto, reinforce the power of transforming ion channels into magnetic field detectors. ProfX will be useful for studying neural circuits.

Methods

Zebrafish Husbandry

Embryos were raised at 28.5° C. in egg water or embryo medium and staged according to hpf or dpf. Embryos of both sexes were used for experiments.

Molecular Biology

Molecular biology was performed using standard protocols. Plasmid DNA was purified using kits from Qiagen. Restriction enzymes were purchased from New England Biolabs. Amplification of template DNA was performed with Phusion Flash (Life Technologies, F-548) and sequenced by GeneWiz. All expression vectors were maintained in the pcDNA3.0 backbone. Fish constructs were cloned using the LR clonase II Gateway system (Invitrogen). Fish constructs were obtained from others. Plasmids used in this study will be deposited in Addgene.

Magnets and Magnetic Field Strength Measurement

Electromagnets of varying sizes and strengths were purchased from Ebay (seller ID: pawnnew). Permanent N42 or N52 grade NdFeB magnets were purchased from CMS Magnetics. A gaussmeter (AlphaLabs, Inc.) was used to determine the field strength of the electromagnets over distance for each experiment. For the in vivo zebrafish behavioral experiments using permanent NdFeB magnets, an online magnetic field calculator (K&J Magnetics) or a guassmeter (AlphaLabs, Inc.) was used.

Cell Transfection and Cell Culture

Cells were transfected using Lipofectamine 2000 (Invitrogen) according to standard protocols. Low passage (<40) HEK293 cells were transfected for 1-2 hours in well plates, trypsinized for 5 minutes using 10% trypsin, and replated onto glass coverslips in fresh DMEM:F12 media (Life Technologies) containing 1× non-essential amino acids (Gibco), 1× sodium pyruvate (Gibco), 10% FBS, 1× penicillin/streptomycin (Gibco).

In Vitro Magnetic Potassium Imaging

Potassium imaging was performed largely the same as calcium imaging described previously (Wheeler et al. 2014). Briefly, transfected cells were plated onto glass coverslips, incubated overnight in a humidified incubator kept at 37° C. and 10% $CO_2$. Cells were washed 3× with calcium imaging buffer (CIB) solution (105 mM NaCl, 3 mM KCl, 2.5 mM $CaCl_2$, 0.6 mM $MgCl_2$, 10 mM HEPES, 1.2 mM $NaHCO_3$, 100 mM mannitol, and 10 mM glucose, adjusted to pH 7.45 with NaOH) (Oiler et al. 2002) and loaded with 3 µM APG-2 (Teflabs) diluted in CIB for 30 minutes at 37° C. Cells were then washed of the dye 3× with CIB and deesterified for 30-60 minutes at 37° C. Coverslips were then loaded into customized imaging chambers and imaged at 10× magnification for analysis.

A magnetic stimulus was delivered using purchased electromagnets (eBay, sellerID: pawnnew) ruled for continuous duty, 12 VDC, 5 W, and 10 kg of pull-force. We situated the magnet directly above the imaging chamber during imaging. Using a Gaussmeter (AlphaLab Inc.), we calculated the magnetic force experienced by the cells (~1.25 cm away from the magnet) to be roughly 40-50 mT (Extended Data 3).

Imaging was performed by recording 30 seconds of baseline fluorescence and then turning on the magnet for 6 or 12 pulses of 5 seconds (0.2 Hz, total time of 30-60 seconds, 90% duty cycle), using a standard DC powered delivery system. Coverslips were not analyzed if they significantly shifted during imaging.

Quantification of fluorescence was measured by averaging the smallest three values after baseline measurements, and normalizing those values to average baseline fluorescence before magnetic stimulation to yield a fluorescence fold change. Fold change was normalized to background by respectively scaling all values by the average fold change in the background (if applicable) during magnetic stimulation.

Fish Injection

In Vivo Zebrafish Imaging

Imaging was performed as described previously (Smith et al. 2014).

Microscopy

Imaging for calcium imaging and immunostaining was performed on a Leica SP5 confocal with white light laser. Calcium imaging was performed using 10× magnification.

Zebrafish Behavioral Tests

Injected fish were maintained on an AB* background strain. Zebrafish embryos were behaviorally tested between 24-34 hours post fertilization (hpf). Two 2"×0.5"×0.25" N52 grade NdFeB permanent magnets were oriented such that one south and one north pole was oriented towards the fish over a distance of ~1 cm. Fish were maintained in egg water during the course of behavioral testing and a 30 fps video was taken using an Axio Zoom.V16 fluorescent stereo zoom microscope. The videos were manually scored by counting the number of coils made by each fish over the length of the video and normalized as a rate of coiling by dividing the number of coils by the length of the video.

Example 3

Remote Suppression of Epileptic Seizures
Introduction

Epilepsy is the fourth most common neurological disorder with only migraine, stroke and Alzheimer's disease occurring more often. The NIH estimates that 3 million Americans live with epilepsy and costs the US over $17.6 billion each year. Although the molecular and cellular changes that transition a normal brain into one that suffers from spontaneous seizures vary, the end point is always an increase in neuronal excitability in a brain node that initiates these events. Patients with epilepsy are severely debilitated by the unexpected nature of seizure episodes, face paralysis and even death. Current treatment options are targeted to reduce the frequency and severity of seizures using pharmacology. Unfortunately, medical treatment of epilepsy fails in 35% of cases, leaving 375,000 refractory patients. For over 40 years, the only option left for these patients has been surgical resection of hyperexcitable tissue. Although surgery can be very effective in controlling seizures, the success rate is low, so there is a great desire to develop therapies that reduce the activity of these hyperexcitable neurons within the seizure onset zone. Recently, there has been unprecedented effort to develop tools that can precisely control neuronal activity to identify causes of and devise treatment strategies for brain diseases. However, as treatments, these tools are either slow or highly invasive. The "dream tool" for neural circuit control would be one that remotely manipulates specific cells with temporal resolution approaching normal neuronal activity rates. Herein is disclosed a strategy to engineer and use magnetically-controlled ion channels that can fulfill this dream. In contrast to current methods for circuit control, this approach is minimally invasive while operating at physiologically relevant time scales and allow manipulation of defined subsets of neurons. This magnetogenetic toolset will effectively remediate epilepsy by normalizing hyperexcitable neural networks of this brain disorder.

Relevance to Traumatic Brain Injury (TBI)

TBI can lead to the development of epilepsy and accounts for up to 20% of the acquired epilepsies and 6% of all causes for epilepsy[1,2]. Additionally, TBI epilepsy frequently does not respond to available treatments, imposing significant ill effects on quality of life and rehabilitation. Prior attempts to intervene and prevent epilepsy after injury have yet to succeed. Inhibition of seizures using magnetically-controlled ion channels will fulfill the void in the ability to control epilepsy during recovery from head trauma and allow for better treatment outcomes in high risk patients.

Inhibit seizures in a brain injury model of epilepsy by magnetically controlled actuators.

Increased activity of excitatory neurons leads to epileptic seizures. Reducing the activity of excitatory neurons using magnetically controlled actuators will suppress seizure activity in the mouse brain injury model of epilepsy. A virus will be used to deliver an inhibitory magnetically controlled ion channel to a subset of excitable neurons. Activation of this channel with magnetic field application will reduce neuronal excitability and inhibit seizure initiation and propagation.

Suppress seizures in a human genetic mouse model of epilepsy using magnetically controlled actuators.

A knock-in mouse model carrying a human sodium channel mutation exhibits many of the pathological phenotypes seen in patients, including spontaneous seizures and sudden death. It is hypothesize that magnetic inhibition of hyperexcitable neurons will suppress seizure activity in this model of human epilepsy.

Results and Discussion

Epilepsy is a debilitating and severe neurological disorder without a cure. Herein is proposed a paradigm-shift in the treatment strategy of this brain disorder by using magnetically controlled ion channels to remotely suppress neuronal hyperexcitability and thus, suppress seizures. This novel epilepsy treatment strategy will revolutionize the current clinical methods for the treatment of epilepsy and will be first in its class.

Epilepsy is a significant neurological disorder characterized by recurrent spontaneous seizures. In the US alone, approximately 200,000 new epilepsy cases are diagnosed while 25,000 patients die from epilepsy related causes each year. Without a cure, epilepsy is a major economic and personal burden for the American public. The causes of epilepsy vary from head trauma, brain malformations, brain tumors, viral infections to genetic mutations. However, a common end point is the existence of hyperexcitable neurons that continue to provide excessive and continuous excitatory drive into neuronal networks, initiating and propagating epileptic seizures'. Seizures are most commonly suppressed by the use of antiepileptic drugs. Unfortunately, these pharmaceutical interventions are ineffective in approximately a third of the patients and are associated with adverse side effects most likely since these drugs modulate the activity of all neurons indiscriminately. Herein a highly innovative and novel approach for suppressing epilepsy by remotely inhibiting the activity of seizure-causing neurons using magnetically controlled ion channels is proposed.

One of the fundamental scientific challenges of this time is to understand how the nervous system is assembled, functions and is dysregulated during disease[4,5]. It is finally possible to precisely delineate the neural correlates of physiology and behavior with the advent of opto- and chemogenetic tools to manipulate neural circuit activity[6,7]. While these have been important tools for research, they have not been useful for therapy. The problem is that optogenetics requires invasive surgery to implant light-delivering fiber optic lines deep into the brain as well as a requisite headpiece. Chemogenetic methods, similar to pharmacological agents, although free of physical tethering, exhibit a temporal resolution of minutes to hours well beyond the meaningful timeframe of fast-paced cellular processes such as those related to neuronal firing—bringing a sledgehammer approach to diseases that require a scalpel. The limitations of these existing technologies inspired the development of a minimally invasive toolset while allowing the manipulation of broad or restricted subsets of cells at millisecond timescales. Herein is provided a strategy to inhibit cell-specific neuronal function using magnetically-controlled molecular tools and apply it to epilepsy.

For the first magnetically gated actuator, an encoded paramagnetic nanoparticle, ferritin (a ubiquitous iron storage protein), was fused with a non-selective cation channel TRPV4[8-10]. In the presence of a magnetic field this synthetic channel (called Magneto) activates and increases the firing rate of neurons that express it. The utility of this channel has been validated in freely moving animals. Herein it is proposed that a similar fusion approach of ferritin with a potassium channel will allow remote inhibition of distinct neuronal populations, which will be particularly useful to treat epilepsy (FIG. 19A).

A two-pore domain potassium (K2P) channel, TREK-1 (KCNK2 gene), when activated lowers the neuronal resting membrane potential, hyperpolarizing neurons and inhibiting action potential generation[11,12]. Genetic ablation of TREK-1 increases seizure susceptibility[13] and expression of a constituently active form of TREK-1 silence hyperactive neurons in epileptic rats reducing the time spent in status epilepticus[14]. To attain remote temporal precision while silencing neuronal activity, which is required for clinical applications, TREK-1 was fused with a ferritin moiety. Complementing the prototype magnetically-controlled neuronal activator channel, Magneto, this next generation engineered channel, ProfX, when expressed in hippocampal excitatory neurons robustly inhibits induced action potentials upon introduction of a magnetic field (FIGS. 19b-c).

The strategy to engineer magnetically-controlled molecular tools to activate or inhibit cell-specific neuronal function is the cutting-edge of neuronal activity control and can be applied to brain disorders, such as epilepsy. This type of magnetogenetic neuronal intervention approach will be used both in discovering the etiology of other brain maladies and development of therapeutic strategies.

Upon exposure to magnetic fields, ProfX expressed in hippocampal neurons inhibits induced action potentials (FIGS. 19b-c). This magnetically controlled inhibitory activity of ProfX was able to block electrically induced seizures in kindled mice. In these animals, activation of ProfX in the hippocampus elevates the current intensity threshold necessary to induce a seizure (after discharge thresholds; ADT) (FIG. 20). These preliminary data that remote inhibition of hyperactive neurons is a tractable approach to control epilepsy.

Inhibit seizures in a brain injury model of epilepsy by magnetically controlled actuators.

Inhibition of increased excitatory neuron activity using magnetically controlled actuators will suppress seizure activity in the mouse brain injury model of epilepsy.

Brain injury leads to the development of hyperexcitable neurons and seizures. Tools that remotely silence select hyperactive neuronal networks will allow novel therapeutic interventions for many brain diseases, including epilepsy, with minimal off-target effects and maximal positive outcomes. The stretch-activated K+ channel, TREK-1, was fused to ferritin (FIG. 19a). This inhibitory magnetogenetic actuator (called ProfX) hyperpolarizes neurons, making them less hyperexcitable upon exposure to magnetic fields (FIG. 19b). In the kainic acid induced brain injury model of epilepsy ProfX will be expressed within the hippocampus—a key site for seizure initiation and propagation. Magnetic activation of ProfX will reduce neuronal excitability in this key brain region and inhibit spontaneous seizures.

The intrahippocampal kainic acid model of epilepsy is widely used within the epilepsy research community. This model produces robust spontaneous seizures as a result of brain injury approximately two weeks after the unilateral injection of kainic acid into the hippocampus. AAV vectors will be used to deliver ProfX, an inhibitory actuator, bilaterally to excitable neurons (CamKII promoter) within the hippocampus, targeting DG, CA3, CA1 and subiculum neurons. This will be performed 1 week after kainic acid injection. 24 hour Video/EEG will be used to monitor seizure activity in mice. Once a stable seizure frequency pattern is achieved (3-5 seizures per day over a period of 5 days), mice will be placed in a magnetic field box (generating >50 mT) to activate ProfX. Effects on seizure frequency and intensity will be monitored. On completion of these experiments, brain slice experiments will be performed to confirm functional expression of ProfX using patch clamp electrophysiology. As controls, viruses expressing ProfX with a pore mutation that makes the channel non-functional will be injected.

Suppress seizures in a human genetic mouse model of epilepsy using magnetically controlled actuators.

Magnetic activation of ProfX will reduce neuronal hyperexcitability and suppress spontaneous seizures in a human mutation mouse model of epilepsy.

Mutations in sodium channels give rise to epilepsy in humans. Approximately 30% of these patients are refractory to current treatment options. A knock-in mouse model carrying a mutation in the sodium channel isoform Nav1.6 gene (Scn8a; N1768D) which exhibits spontaneous seizures and sudden death as observed in human patients will be utilized. The excitatory neurons within the hippocampus and subiculum of the Scn8a N1768D+/− mice are hyperexcitable compared to their WT littermates. It is hypothesized that magnetic activation of ProfX in excitatory neurons will reduce neuronal hyperexcitability and suppress seizure activity in this mouse model of human epilepsy demonstrating the power of magnetogenetic intervention for brain disorders.

Scn8a N1768D+/− mice begin spontaneously seizing at 8 weeks of age. Hippocampus and subiculum have been heavily implicated with seizure initiation and propagation[15]. It has been demonstrated that Scn8a N1768D+/− hippocampus and subiculum contain hyperexcitable neurons (data not shown). Therefore, viral vectors will be used to express ProfX within these two regions at 6 weeks of age. A separate cohort of mice will be injected with the control virus. At 7 weeks of age, mice will be implanted with recording headsets and 24 hour Video/EEG will be initiated at 8 weeks of age. Mice with stable seizure frequencies (3-5 seizures per day over a period of 5 days) will be placed in a magnetic field box (generating >50 mT) and monitored for suppression of seizures. Follow up electrophysiology experiments will establish functional expression of ProfX and inhibition of neuronal firing my magnetic fields.

The preliminary data in kindled model of seizures (FIG. 20) is demonstrates that magnetic activation of ProfX is a tractable approach to reduce the frequency and intensity of seizures in epilepsy. Therefore, it is beleived that activation of ProfX using magnetic fields will suppress seizure initiation and propagation in both injury induced and genetic models of epilepsy.

The ability to remotely control broad neural networks with millisecond and micrometer precision is critical for translational therapies that require the repair of dysfunctional neural activity. The magnetogenetic tools that are compact, easily activated, and noninvasively controlled are extremely useful for the scientific community and therapeutics will be impact millions worldwide. The application of this magnetogenetic toolset in a clinical setting promises to replace the need for implantation of instruments or replenishment of co-factors. Vectors expressing synthetic genes in humans encoding magnetogenetic tools will allow the rescue of ill-firing neural networks to remediate heretofore intractable diseases. For example, epilepsy patients, infused with a vector that expresses magnetogenetic tools, will be able to receive temporally precise closed-loop neuronal inhibition therapy using a focal magnetic field generator hidden in, for example, their eyeglasses alleviating the severe symptoms of the disease. This strategy will provide a striking quality of life improvement for patients suffering from this debilitating brain disorder that currently lack a cure.

Example 4—Magnetogenetic Approach for the Treatment of Nervous System Injury

Nervous system injury represents a significant and growing health problem both in the U.S. and worldwide. Whether such injury is caused by the severing of nerves or trauma to the brain, the course of treatment often involves a "wait and see" approach. The Christopher and Dana Reeve foundation reports that 1 in 50 people suffer from some form of paralysis, while the Center for Disease Control and Prevention, estimates that traumatic brain injury is a contributing factor in a third of all injury-related deaths (1). Despite the magnitude of this problem and the enormous healthcare costs related to it (over $400 billion/year) there are no effective treatments for this class of injuries, leaving millions of people paralyzed or with long-term symptoms such as paralysis, postconcusive and posttraumatic stress syndromes. Provided herein are tools and methods to promote nerve regeneration using a novel remote nerve cell stimulation paradigm.

In order to effectively treat nervous system injury regeneration of injured neurons must be promoted by allowing them to not only survive but also ignore repulsive cues associated with an injury. Disclosed herein is an approach using magnetogentic technologies to promote nerve regeneration after injury with a series of tools capable of remotely controlling the pathways underlying nerve regeneration. Indeed, the efficacy of such a tool has been demonstrated (Wheeler et al 2016). These magnetically inducible tools will allow for non-invasive therapy, which is an important feature since nerve regeneration can take weeks, months or even years. This approach will provide an avenue to a noninvasive treatment for nerve damage and spinal cord injury.

The current standard of care for nerve damage is to create conduits surgically and allow the axons to regrow toward their target. However, this process is incredibly inefficient and rarely results in full functional recovery. Using the novel remote actuator technology will promote regeneration resulting in full functional recovery.

Developing a proactive means of treating nervous system injury can provide significant physical, emotional, and financial relief for countless patients and their families. There are currently no good treatments for nerve damage, therefore this invention is timely and important for millions of people. Novel, remote controlled actuators will be introduced into damaged nerves such that one can produce neuronal firing and/or pro-growth signaling via pulsing with magnetic field. This technology was validated for the control of neuronal circuits and mouse behavior (Wheeler et al, 2016). A paramagnetic, genetically encoded nanoparticle ferritin was fused with mechanically gated receptors to allow remote control of distinct signaling cascades. These are referred to as actuators—Magneto and Storm to control neuronal firing and cAMP production, respectively. Indeed, activity and cAMP production have already been shown to promote axon regrowth (Neumann et al 2002; Chung et al, 2016). However, an efficient tool to endow an injured neuron with these properties has yet to be described.

The tools described herein offer many advantages, including by not limited, to, the ability to deliver them to a damaged nerve via a single viral injection eliminating the need for invasive surgeries; 2) as these actuators are controlled via remote magnetic stimulation, there is no need to redeliver co-factors every few days or weeks; and 3) the ability to target magnetic fields to the regrowing axonal tracks, with focused stimulation toward areas that have yet to recover (i.e., extremities).

Nerve injury repair remains a pressing unresolved problem in the current medical environment. The actuators described herein will provide a treatment regimen for nerve injury, in particular the devastating injuries effecting movement. This represents a novel bioengineering product that can be applied as a molecular repair kit for damaged nerves. The compositions and methods described herein apply to numerous patients, including but not limited to, those suffering from nerve damage as a result of automobile, work-related, and sports injuries, as well as medical treatment of war fighters. Currently there is a desperate need for such compositions and methods.

Several other technical advances are apparent including, including but not limited to: 1) continued development of novel remote actuators which can be used for applications beyond axon regeneration, 2) production of electromagnetic arenas to promote regeneration, 3) wearable magnetic devices to promote nerve regeneration in a targeted manner, 4) optimized magnetic treatment paradigms to promote nerve regrowth. The economic impacts of a nerve damage treatment are manifold. Nervous system injury represents billions in health care costs, lost income/productivity for the victims, and an incalculable effect on family members.

Pre-Clinical Model for Nerve Regeneration

As a model for nerve injury, crushed sciatic nerve will be used. This is an excellent model, since it contains both sensory axons from the peripheral nervous system and motor neurons from the central nervous system. The crush surgeries will be performed on Sprague-Dawley rats as described previously (Bauder et al., 2005). After the nerve crush, virus expressing Magneto and/or Storm will be injected at the site of injury and allow the animal to recover for several weeks. Functional recovery will be tested for by using a variety of behavioral assays including measuring gait, as well as assessing sensitivity to touch and heat. Anatomical recovery will then be examined on crosssections of sciatic nerve by staining for laminin and by performing electron microscopy to visualize axon bundles. Whole-mount staining of muscles will also be performed to examine denervation of the neuromuscular junction as well as re-establishment of these connections.

Functional Recovery

Figure 21D:
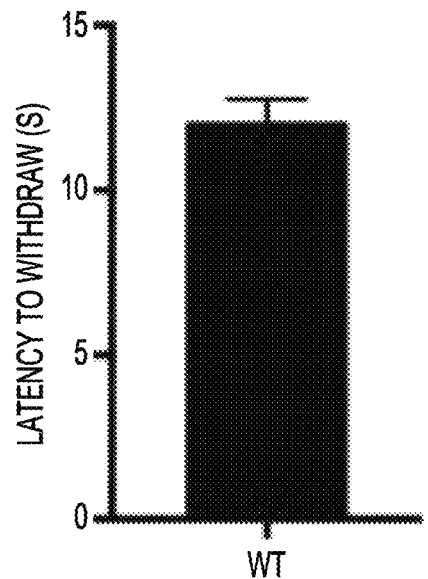
Figure 21E:
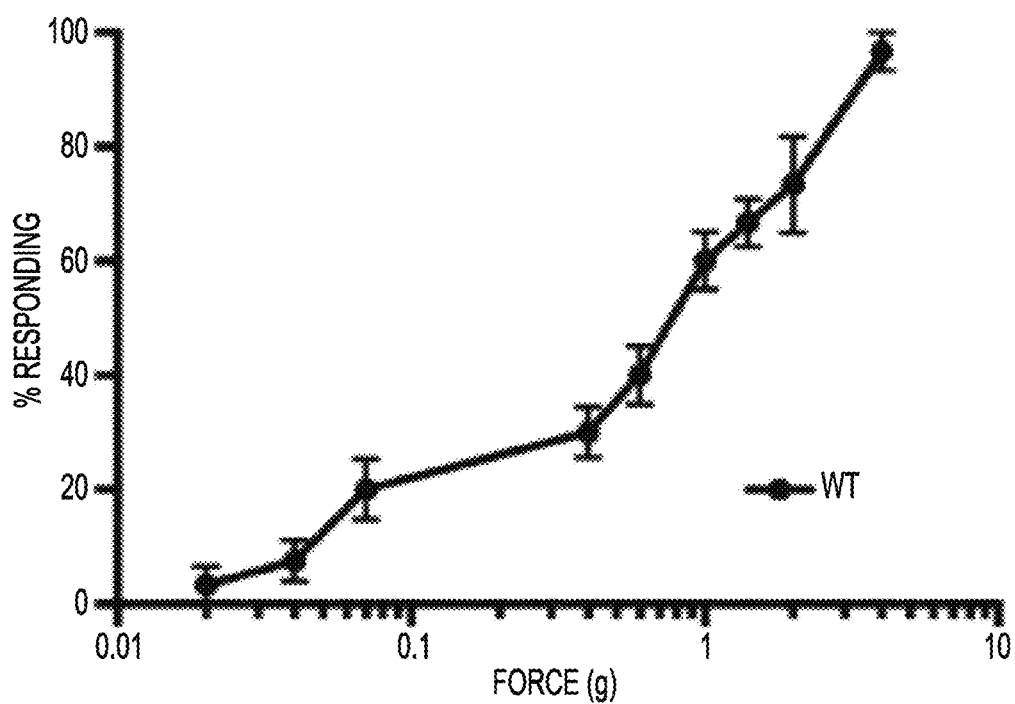

Rats lose motor function and nociception in the effected limb immediately after transection, however, these functions partially return within 10 weeks using conduits containing collagen and laminin hydrogels (Cao et al., 2011). Increased or decreased rates of recovery directly correlate with rates of axon regeneration. Therefore, functional recovery assays will be performed weekly starting at one week after surgery and viral infection. To assess functional recovery of motor neurons, walking track analysis will be used, as previously described (Varejão et al., 2001). Briefly, rats will be allowed 2-3 trials to explore a narrow corridor with a shelter at the end. For the test trial, hind paws are painted with non-irritant, water-soluble paint and mice will be allowed to walk through the corridor lined with paper toward the shelter (FIG. 21b). The walking tracks of pre- and post-injury mice will be analyzed by an experienced blinded investigator to calculate sciatic function index (SFI) and assess functional recovery (Dijksra et al., 1999) (FIG. 21c). Functional recovery of nociceptive axons will be measured as follows: 1) the Radiant heat/Hargreaves's test assesses temperature sensitivity in the absence of tactile information. This assay measures how quickly a noxious thermal stimulus is sensed and avoided through applying an infrared beam to the injured or uninjured mouse hind-paw. The intensity of the IR beam is calibrated such that WT uninjured animals withdrawal their paw at roughly 10 seconds (FIG. 21d); and 2) mechanical nociception using the von Frey assay will also be used. Briefly, rats will be placed on a thin mesh screen and restrained within slightly opaque red containers, which obscures mouse visualization of the incoming probe. Injured and sham hindpaws will be prodded with von Frey filaments of varying diameters to determine the threshold detection sensitivity of a mechanical force (Liu et al. 2009). Each data point is recorded as the percent response of paw lifting per 5 trials per 9 filaments of logarithmically increasing force (FIG. 21e). As controls for both assays, the mechanical and thermal pain thresholds of injured limbs will be compared with contralateral sham surgery limbs.

Remote Neural Activity is Sufficient to Promote Regeneration of Injured Neurons

A two-part biological system to convert magnetic energy to electrical energy at the cellular level has been validated (Wheeler et al., 2016). The first component is a metal-bound peptide that is attracted by magnets and therefore is paramagnetic. The second component is an ion channel that responds to mechanical perturbations. This change in ionic balance can be harnessed to manipulate all electrically active cells, most notably neurons. Therefore, when a magnetic field is introduced, forces generated on the magnetic domain will mimic a mechanical stimulus allowing direct magnetic gating of the channel (FIG. 22).

Remote cAMP Activity is Sufficient to Promote Regeneration of Injured Neurons

Remote actuators to control other signaling pathways, relevant to nerve regeneration, are provided herein as well. Actuators that transduce G-protein signals upon exposure to magnetic fields have been created. Because these second-messenger signaling cascades are components of axon regrowth regeneration, their remote control will provide an opportunity produce long-term, non-invasive stimulation of nerve regeneration. By fusing the stretch-sensing G-protein coupled receptor (GPCR) angiotensin II receptor 1 (AT1R) (Zou et al., 2004) to ferritin, a Gq-coupled magnetogenetic actuator (Quicksilver) was generated. When activated by a magnetic field, this receptor is able to initiate the phospholipase C (PLC) signaling cascade and activate ERK (FIG. 23a, d-e), a downstream target of AT1R signaling (Zou et al., 2004). Perhaps most relevant to regeneration, is the generation of magnetically-activated actuators that bi-directionally manipulate an adenylate cyclase (AC) signaling cascade by substituting intracellular domains of Quicksilver with ones from either $G_s$- or $G_i$-coupled GPCRs dubbed Storm and Iceman, respectively (FIG. 23b-d) (Airan et al., 2009; Yin et al., 2004; Frielle et al., 1988). These chimeric receptors have been successfully used to diversify the portfolio of other actuator systems including light-gated receptors (OptoXRs) (Airan et al., 2009). These two new actuators upon exposure to a magnetic field will be able to modulate AC activity by monitoring levels of cAMP. It is expected to show an increase or decrease in cAMP levels and subsequent signaling with Storm and Iceman, respectively. To demonstrate their utility in vivo, these tools will be applied to the injured nerves.

After the ability of these actuators to promote regeneration have been tested individually, they will then be tested in combination.

Example 5

In the pancreas, insulin secretory cells can become insensitive to glucose, but still produce insulin (just not secret it with normal signals). However, this can be modified by the actuators described herein. Pancreatic cells can be transduced with a composition described herein. When glucose is determined to be to be high, through monitoring (in for example in a diabetic subject), exposure to a magnet can cause the actuator/channel to open, allowing ions to pass and endogenous insulin to be secreted out of the cell (e.g., TRPV-4/ferritin channel expressed in beta cells; calcium goes through channel into cell and insulin is released when channel is exposed to a magnet/"turned on").

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY—EXAMPLE 1

1. Zemelman et al., *Neuron* 33, 15-22 (2002).
2. Boyden et al., *Nat. Neurosci.* 8, 1263-1268 (2005).
3. Gradinaru et al., *Science* 324, 354-359 (2009).
4. Sternson et al., *Annu. Rev. Neurosci.* 37, 387-407 (2014).
5. Alexander et al., *Neuron* 63, 27-39 (2009).
6. Güler et al., *Nat. Commun.* 3, (2012).
7. Bernstein et al., *Curr. Opin. Neurobiol.* 22, 61-71 (2012).
8. Hughes et al., J. R. *Soc. Interface* 5, 855-863 (2008).
9. Huang et al., *Nat. Nanotechnol.* 5, 602-606 (2010).
10. Stanley et al., *Science* 336, 604-608 (2012).
11. Stanley et al., *Nat. Med.* 21, 92-98 (2015).
12. Chen et al., *Science* (2015).
13. Liedtke et al., *Cell* 103, 525-535 (2000).
14. Güler et al., *J. Neurosci.* 22, 6408-6414 (2002).
15. Stanley *Curr. Opin. Biotechnol.* 28, 69-74 (2014).
16. Iordanova et al., *J. Biol. Inorg. Chem.* 15, 957-965 (2010).
17. Lei et al., *J Biol. Chem.* 288, 10427-10439 (2013).
18. Hofherr et al., *J Cell Sci* 118, 1935-1943 (2005).
19. Gradinaru et al., *Cell* 141, 154-165 (2010).
20. Andermann et al., *Dev. Biol.* 251, 45-58 (2002).
21. Douglass et al., *Curr. Biol.* 18, 1133-1137 (2008).
22. Fisher et al., *Nat. Prot.* 1, 1297-1305 (2006).
23. Sohal et al., *Nature* 459, 698-702 (2009).
24. Lobo et al., *Science* 330, 385-390 (2010).
25. Berke et al., *Neuron* 43, 883-896 (2004).
26. Wise *Nat. Rev. Neurosci* 5, 483-494 (2004).
27. Tsai et al., *Science* 324, 1080-1084 (2009).
28. Gore et al., *J Neurosci.* 33, 8640-8649 (2013).
29. Zengin-Toktas et al., *Neuropharmacology* 70, 74-82 (2013).
30. Stuber et al., *Biol. Psychiat.* 71, 1061-1067 (2012).

SUPPLEMENTARY
BIBLIOGRAPHY—EXAMPLE 1

1. Cao E, et al., *Nature* 504, 113-118 (2013).
2. Paulsen C E, et al., *Nature* 520, 511-517 (2015).

3. Kimmel C B, et al., *Dev. Dyn.* 203, 253-310 (1995).
4. Iordanova B, et al., *J Biol. Inorg. Chem.* 15, 957-965 (2010).
5. Wheeler M A, et al., *Neuron* 82, 587-602 (2014).
6. Oiler A D, et al., *J Neurosci.* 22, 6408-6414 (2002).
7. Smith C J, et al., *PLoS Biol.* 12, e1001961 (2014).
8. McFarland T J, et al., *Plasmid* 56, 62-67 (2006).
9. Güler A D, et al., *Nat. Commun.* 3, (2012).

BIBLIOGRAPHY—EXAMPLE 2

1. M. A. Wheeler, D. L. Heffner, S. Kim, S. M. Espy, A. J. Spano, C. L. Cleland, C. D. Deppmann, *Neuron* 82, 587-602 (2014).
2. A. D. Güler, H. Lee, T. Iida, I. Shimizu, M. Tominaga, M. Caterina, *J Neurosci.* 22, 6408-6414 (2002).
3. C. J. Smith, A. D. Morris, T. G. Welsh, S. Kucenas, *PLoS Biol.* 12, e1001961 (2014).

BIBLIOGRAPHY—EXAMPLE 3

1 Agrawal, A., et al. *Clin Neurol Neurosurg* 108, 433-439, doi:10.1016/j.clineuro.2005.09.001 (2006).
2 Lowenstein, D. H. *Epilepsia* 50 Suppl 2, 4-9, doi:10.1111/j.1528-1167.2008.02004.x (2009).
3 Jiruska, P. et al. *J Physiol* 591, 787-797, doi:10.1113/jphysiol.2012.239590 (2013).
4 Guler, A. D. et al. *Nature* 453, 102-105, doi:10.1038/nature06829 (2008).
5 Guler, A. D. et al. *Nat Commun* 3, 746, doi:10.1038/ncomms1749 (2012).
6 Fenno, L., Yizhar, O. & Deisseroth, K. *Annu Rev Neurosci* 34, 389-412, doi:10.1146/annurev-neuro-061010-113817 (2011).
7 Sternson, S. M. & Roth, B. L. *Annu Rev Neurosci* 37, 387-407, doi:10.1146/annurev-neuro-071013-014048 (2014).
8 Guler, A. D. et al. *J Neurosci* 22, 6408-6414, doi:20026679 (2002).
9 Stanley, S. *Curr Opin Biotechnol* 28, 69-74, doi:10.1016/j.copbio.2013.11.014 (2014).
10 Wheeler, M. A. et al. *Nat Neurosci* 19, 756-761, doi: 10.1038/nn.4265 (2016).
11 Honore, E. *Nat Rev Neurosci* 8, 251-261, doi:10.1038/nrn2117 (2007).
12 Nilius, B. & Honore, E. *Trends Neurosci* 35, 477-486, doi:10.1016/j.tins.2012.04.002 (2012).
13 Heurteaux, C. et al. *EMBO J* 23, 2684-2695, doi:10.1038/sj.emboj.7600234 (2004).
14 Dey, D. et al. *Epilepsia* 55, 203-213, doi:10.1111/epi.12472 (2014).
15 Fujita, S., et al. J Neurosci 34, 16671-16687,doi:10.1523/JNEUROSCI.0584-14.2014 (2014).

BIBLIOGRAPHY—EXAMPLE 4

1. Airan, R. D., et al. Nature 458, 1025-1029 (2009).
2. Bauder A R, & Ferguson T A. J Vis. Exp. (60). pii: 3606.
3. Chung, Samuel H., et al. Proceedings of the National Academy of Sciences (2016): 201600564.
4. Frielle, T., et al. Proc. Natl. Acad. Sci. U.S.A. 85, 9494-9498 (1988).
5. Neumann, et al. Neuron 34, no. 6 (2002): 885-893.
6. Wheeler, Michael A., et al. Nature neuroscience (2016).
7. Yin, D., et al. Mol. Pharmacol. 65, 1323-1332 (2004).
8. Zou, Y. et al. Nat. Cell Biol. 6, 499-506 (2004).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A composition comprising a fusion protein, wherein the fusion protein comprises:
   a channel component or a G-protein coupled receptor (GPCR);
   a ferritin component; and
   a membrane trafficking signal (TS).

2. A composition comprising a nucleic acid coding for a fusion protein, wherein the fusion protein comprises:
   a channel component or a G-protein coupled receptor (GPCR);
   a ferritin component; and
   a membrane trafficking signal (TS).

3. The composition of claim 2, wherein the fusion protein is a single-component magnetogenetic actuator/a genetically encoded actuator.

4. The composition of claim 2, wherein the channel component is a transient receptor potential vanilloid 4 (TRPV4) or a potassium (K) channel.

5. The composition of claim 4, wherein the potassium (K) channel is TREK-1.

6. The composition of claim 2, wherein the ferritin component comprises at least two subunits of ferritin.

7. The composition of claim 2, wherein the membrane trafficking signal (TS) is located on the C-terminus of the ferritin component.

8. The composition of claim 2, wherein the fusion protein further comprises an endoplasmic reticulum (ER) export signal.

9. The composition of claim 2, wherein the fusion protein is magnetically sensitive/responds to a magnet.

10. The composition of claim 2 further comprising a pharmaceutically acceptable carrier.

11. A host cell comprising the nucleic acid of claim 2 or the fusion protein of claim 1.

12. A method to manipulate cellular activity comprising contacting a cell with the composition of claim 2 and exposing the cell to a magnet/magnetic field.

13. The method of claim 12, wherein the cellular activity membrane protein activity.

14. The method of claim 12, wherein the cellular activity ion channel activity.

15. The method of claim 12, wherein the cell is a neural/nerve cell.

16. The method of claim 15, wherein the magnetic field causes an increase or decrease/inhibition in neural firing.

17. The method of claim 16, wherein the composition transduces neural cells.

18. A method to treat a neural injury or disease comprising administering to a subject in need thereof a composition of claim 2 or 1 and exposing said subject to a magnet/magnetic field.

19. The method of claim 18, wherein the neural injury or disease is schizophrenia, autism, Parkinson's disease (PD) Huntington's disease (HD), epilepsy, Amyotrophic lateral sclerosis (ALS), catalepsy, bipolar disorder, attention deficit/hyperactivity disorder (ADHD), locked-in syndrome, migraine, multiple sclerosis (MS), physical or infectious neuron/brain trauma, neuron degeneration, stroke, basal ganglia disease, dyskinesia, tremor, restless legs, cerebral palsy, coma, concussion, dementia, ataxia, locked-in syndrome (LiS), narcolepsy, Prader-Willi Syndrome, sleep disorders, Asperger Syndrome, pain, Creutzfeldt-Jakob Disease, cumulative trauma disorders, Cushing's Syndrome, diabetic neuropathy, diffuse sclerosis, seizures, or spinal cord injury.

\* \* \* \* \*